United States Patent
Andoh et al.

(10) Patent No.: US 9,907,778 B2
(45) Date of Patent: Mar. 6, 2018

(54) ANTICANCER AGENT COMPRISING AMINOACETONITRILE COMPOUND AS ACTIVE INGREDIENT

(71) Applicant: PITNEY PHARMACEUTICALS PTY LIMITED, Claremont, Western Australia (AU)

(72) Inventors: Nobuharu Andoh, Kawachinagano (JP); Osamu Sanpei, Kawachinagano (JP); Tetsuo Toga, Kawachinagano (JP); David Lawson Morris, Lugarno (AU); Roger Aston, Manly (AU); Koji Tanaka, Kawachinagano (JP); Tomokazu Hino, Kawachinagano (JP)

(73) Assignee: Pitney Pharmaceuticals Pty Limited, Claremont (AU)

( * ) Notice: Subject to any disclaimer, the term of this patent is extended or adjusted under 35 U.S.C. 154(b) by 0 days.

(21) Appl. No.: 14/917,724

(22) PCT Filed: Sep. 12, 2014

(86) PCT No.: PCT/JP2014/074764
§ 371 (c)(1),
(2) Date: Mar. 9, 2016

(87) PCT Pub. No.: WO2015/037747
PCT Pub. Date: Mar. 19, 2015

(65) Prior Publication Data
US 2016/0213640 A1    Jul. 28, 2016

(30) Foreign Application Priority Data
Sep. 13, 2013   (JP) .................................. 2013-190509

(51) Int. Cl.
*A61K 31/341*   (2006.01)
*A61K 31/4245*   (2006.01)
(Continued)

(52) U.S. Cl.
CPC .......... *A61K 31/277* (2013.01); *A61K 31/341* (2013.01); *A61K 31/381* (2013.01); *A61K 31/415* (2013.01); *A61K 31/4196* (2013.01); *A61K 31/42* (2013.01); *A61K 31/421* (2013.01); *A61K 31/426* (2013.01); *A61K 31/4245* (2013.01); *A61K 31/433* (2013.01); *A61K 31/437* (2013.01); *A61K 31/44* (2013.01); *A61K 31/4965* (2013.01); *A61K 31/505* (2013.01); *A61K 31/5377* (2013.01); *A61K 31/5383* (2013.01)

(58) Field of Classification Search
CPC .............. A61K 31/341; A61K 31/4245; A61K 31/5383; A61K 31/4196; A61K 31/437; A61K 31/381; A61K 31/5377; A61K 31/415

See application file for complete search history.

(56) References Cited

U.S. PATENT DOCUMENTS

| 6,239,077 | B1 | 5/2001 | Andoh et al. |
| 6,812,237 | B2 | 11/2004 | Cowen et al. |
| 7,052,707 | B2 | 5/2006 | Ducray et al. |
| 7,063,856 | B2 | 6/2006 | Ducray et al. |

(Continued)

FOREIGN PATENT DOCUMENTS

| JP | 2000-026392 A1 | 1/2000 |
| WO | WO 2000/049007 A1 | 8/2000 |
| WO | WO 2002/060257 A1 | 8/2002 |
| WO | 2003004474 | * 1/2003 |
| WO | WO 2005/044784 A1 | 5/2005 |
| WO | WO 2006/043654 A1 | 4/2006 |
| WO | 2002/060257 | * 8/2007 |

OTHER PUBLICATIONS

European Patent Office, International Search Report in International Application No. PCT/JP2014/074764 (dated Jan. 20, 2015).

*Primary Examiner* — Alexander R Pagano
*Assistant Examiner* — Ebenezer O Sackey
(74) *Attorney, Agent, or Firm* — Leydig, Voit & Mayer, Ltd.

(57) ABSTRACT

The present invention relates to an anticancer agent having a high safety and a superior anticancer activity, and an anticancer agent containing, as an active ingredient, an aminoacetonitrile compound represented by the formula (I) wherein $R^1$ is a hydrogen atom, an alkyl group and the like, $R^2$, $R^3$, and $R^4$ are the same or different and each is a hydrogen atom, an alkyl group and the like, $R^5$ and $R^6$ are the same or different and each is a hydrogen atom, a halogen atom and the like, m is 0 or 1, R is a halogen atom, a cyano group, a nitro group, a phenyl group optionally substituted by an alkyl group and the like, an alkyl group and the like, $Ar^1$ is a phenyl group, a naphthyl group, a pyridyl group, a pyrazolyl group, or the like, each of which is optionally substituted by a halogen atom, a cyano group, a nitro group, alkyl group and the like, and W is —O—, —S—, —$SO_2$—, or —N($R^7$)— wherein $R^7$ is a hydrogen atom, a ($C_1$-$C_6$)alkyl group and the like, or a pharmacologically acceptable salt thereof.

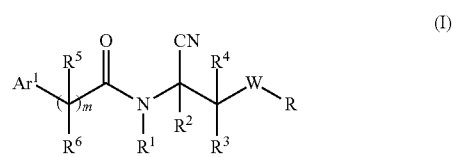

(I)

12 Claims, No Drawings

(51) Int. Cl.
| | |
|---|---|
| *A61K 31/5383* | (2006.01) |
| *A61K 31/4196* | (2006.01) |
| *A61K 31/437* | (2006.01) |
| *A61K 31/381* | (2006.01) |
| *A61K 31/5377* | (2006.01) |
| *A61K 31/415* | (2006.01) |
| *A61K 31/277* | (2006.01) |
| *A61K 31/42* | (2006.01) |
| *A61K 31/421* | (2006.01) |
| *A61K 31/426* | (2006.01) |
| *A61K 31/433* | (2006.01) |
| *A61K 31/44* | (2006.01) |
| *A61K 31/4965* | (2006.01) |
| *A61K 31/505* | (2006.01) |

(56) References Cited

U.S. PATENT DOCUMENTS

| | | |
|---|---|---|
| 7,494,956 B2 | 2/2009 | Gauvry et al. |
| 7,964,635 B2 | 6/2011 | Gauvry et al. |
| 2003/0158256 A1 | 8/2003 | Cowen et al. |
| 2004/0044074 A1 | 3/2004 | Ducray et al. |
| 2004/0063766 A1 | 4/2004 | Ducray et al. |
| 2007/0072944 A1 | 3/2007 | Gauvry et al. |
| 2009/0176868 A1 | 7/2009 | Gauvry et al. |

\* cited by examiner

ANTICANCER AGENT COMPRISING AMINOACETONITRILE COMPOUND AS ACTIVE INGREDIENT

CROSS-REFERENCE TO RELATED APPLICATIONS

This patent application is the U.S. national phase of International Patent Application No. PCT/JP2014/074764, filed Sep. 12, 2014, which claims the benefit of Japanese Patent Application No. 2013-190509, filed on Sep. 13, 2013, which are incorporated by reference in their entireties herein.

TECHNICAL FIELD OF THE INVENTION

The present invention relates to an anticancer agent containing an aminoacetonitrile compound or a pharmacologically acceptable salt thereof as an active ingredient, a treatment method of cancer using an aminoacetonitrile compound or a pharmacologically acceptable salt thereof and the like.

BACKGROUND OF THE INVENTION

Patent documents 1 and 2 describe that a certain kind of aminoacetonitrile compound is useful as an agri-horticultural insecticide and an ectoparasiticide, respectively, but no prior art documents suggest or disclose anything relating to an anticancer action thereof.

DOCUMENT LIST

Patent Document

[patent document 1] JP-A-2000-026392
[patent document 2] WO 2005/044784

SUMMARY OF THE INVENTION

Problems to be Solved by the Invention

Cancer (malignant tumor) is a cell group that deviates from the normal biological mechanism and continues to grow in a living body to lead the host to the demise. The treatment method of cancer generally includes surgical operation, radiation therapy, hormone therapy, chemical therapy, and combined use thereof. Of these, the chemical therapy using a medicament is not the main treatment method, because a medicament having a clinically effective anticancer activity but free of severe side effects does not exist. Therefore, creation of an anticancer agent having a high safety and a superior anticancer activity has been demanded.

Means of Solving the Problems

The present inventors have screened pharmacological actions of various compounds and found that a certain kind of aminoacetonitrile compound has a cell growth inhibitory action and an anticancer activity, and completed the present invention.

Accordingly, the present invention relates to
[1] an anticancer agent comprising, as an active ingredient, an aminoacetonitrile compound represented by the formula (I)

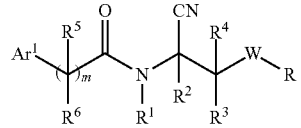

wherein
$R^1$ is
(a1) a hydrogen atom,
(a2) a $(C_1\text{-}C_6)$alkyl group,
(a3) a $(C_2\text{-}C_6)$alkenyl group,
(a4) a $(C_2\text{-}C_6)$alkynyl group, or
(a5) a $(C_3\text{-}C_6)$cycloalkyl group;
$R^2$, $R^3$, and $R^4$ are the same or different and each is
(b1) a hydrogen atom,
(b2) a $(C_1\text{-}C_6)$alkyl group, or
(b3) a $(C_3\text{-}C_6)$cycloalkyl group, or
(b4) $R^2$ and $R^3$ are optionally bonded to form a $(C_1\text{-}C_6)$ alkylene group wherein the $(C_1\text{-}C_6)$alkylene group optionally has the same or different one or more substituents selected from a halogen atom, a $(C_1\text{-}C_6)$alkyl group, and a $(C_1\text{-}C_6)$alkoxy group on the chain;
$R^5$ and $R^6$ are the same or different and each is
(c1) a hydrogen atom,
(c2) a halogen atom,
(c3) a $(C_1\text{-}C_6)$alkyl group,
(c4) a $(C_3\text{-}C_6)$cycloalkyl group, or
(c5) a $(C_1\text{-}C_6)$alkoxy group, or
(c6) $R^5$ and $R^6$ are optionally bonded to form a $(C_1\text{-}C_6)$ alkylene group;
m is 0 or 1;
R is
(d1) a phenyl group,
(d2) a phenyl group having, on the ring, the same or different 1 to 5 substituents selected from
 (a) a halogen atom,
 (b) a cyano group,
 (c) a nitro group,
 (d) a $(C_1\text{-}C_6)$alkyl group,
 (e) a halo$(C_1\text{-}C_6)$alkyl group,
 (f) a $(C_2\text{-}C_6)$alkenyl group,
 (g) a $(C_2\text{-}C_6)$alkynyl group,
 (h) a $(C_1\text{-}C_6)$alkoxy group,
 (i) a halo$(C_1\text{-}C_6)$alkoxy group,
 (j) a halo$(C_2\text{-}C_6)$alkenyloxy group,
 (k) a halo$(C_2\text{-}C_6)$alkynyloxy group,
 (l) a $(C_1\text{-}C_6)$alkylthio group,
 (l1) a $(C_1\text{-}C_6)$alkylsulfinyl group,
 (m) a $(C_1\text{-}C_6)$alkylsulfonyl group,
 (n) a halo$(C_1\text{-}C_6)$alkylthio group,
 (n1) a halo$(C_1\text{-}C_6)$alkylsulfinyl group,
 (n2) a halo$(C_1\text{-}C_6)$alkylsulfonyl group,
 (o) a phenyl$(C_2\text{-}C_6)$alkynyl group,
 (o1) a phenyl group,
 (o2) a phenyl group having, on the ring, the same or different 1 to 5 substituents selected from
  (i) a halogen atom,
  (ii) a cyano group,
  (iii) a nitro group,
  (iv) a $(C_1\text{-}C_6)$alkyl group, and
  (v) a halo$(C_1\text{-}C_6)$alkyl group;
 (p) a phenoxy group,
 (q) a pyridyloxy group having, on the ring, the same or different 1 to 4 substituents selected from
  (i) a halogen atom, and
  (ii) a halo$(C_1\text{-}C_6)$alkyl group;

(r) a pyridyl($C_2$-$C_6$)alkynyl group,
(s) a ($C_1$-$C_6$)alkylcarbonyl group,
(t) a ($C_1$-$C_6$)alkoxycarbonyl group,
(u) an aminocarbonyl group,
(v) a ($C_1$-$C_6$)alkylcarbonylamino group,
(w) a ($C_1$-$C_6$)alkoxycarbonylamino group,
(x) a di($C_1$-$C_6$)alkylamino group (the alkyl groups are the same or different), and
(y) a ($C_1$-$C_6$)alkylaminocarbonylamino group,
(d3) a naphthyl group,
(d4) a naphthyl group having, on the ring, the same or different 1 to 7 substituents selected from
  (a) a halogen atom,
  (b) a cyano group,
  (c) a nitro group,
  (d) a ($C_1$-$C_6$)alkyl group, and
  (e) a halo($C_1$-$C_6$)alkyl group,
(d5) a ($C_1$-$C_{12}$)alkyl group,
(d6) a pyridyl group,
(d7) a pyridyl group having, on the ring, the same or different 1 to 4 substituents selected from
  (a) a halogen atom,
  (b) a cyano group,
  (c) a nitro group,
  (d) a ($C_1$-$C_6$)alkyl group, and
  (e) a halo($C_1$-$C_6$)alkyl group,
(d8) a pyrazinyl group,
(d9) a pyrazinyl group having, on the ring, the same or different 1 to 3 substituents selected from
  (a) a halogen atom,
  (b) a cyano group,
  (c) a nitro group,
  (d) a ($C_1$-$C_6$)alkyl group, and
  (e) a halo($C_1$-$C_6$)alkyl group,
(d10) a thiazolyl group,
(d11) a thiazolyl group having, on the ring, the same or different 1 to 2 substituents selected from
  (a) a halogen atom,
  (b) a cyano group,
  (c) a nitro group,
  (d) a ($C_1$-$C_6$)alkyl group, and
  (e) a halo($C_1$-$C_6$)alkyl group,
(d12) a pyrazolyl group, or
(d13) a pyrazolyl group having, on the ring, the same or different 1 to 3 substituents selected from
  (a) a halogen atom,
  (b) a cyano group,
  (c) a nitro group,
  (d) a ($C_1$-$C_6$)alkyl group, and
  (e) a halo($C_1$-$C_6$)alkyl group;
$Ar^1$ is
(e1) a phenyl group,
(e2) a phenyl group having, on the ring, the same or different 1 to 5 substituents selected from
  (a) a halogen atom,
  (b) a cyano group,
  (c) a nitro group,
  (d) a ($C_1$-$C_6$)alkyl group,
  (e) a halo($C_1$-$C_6$)alkyl group,
  (f) a ($C_2$-$C_6$)alkenyl group,
  (g) a ($C_2$-$C_6$)alkynyl group,
  (h) a ($C_1$-$C_6$)alkoxy group,
  (i) a halo($C_1$-$C_6$)alkoxy group,
  (j) a halo($C_2$-$C_6$)alkenyloxy group,
  (k) a halo($C_2$-$C_6$)alkynyloxy group,
  (l) a ($C_1$-$C_6$)alkylthio group,
  (m) a ($C_1$-$C_6$)alkylsulfonyl group,
  (n) a halo($C_1$-$C_6$)alkylthio group,
  (o) a phenyl($C_2$-$C_6$)alkynyl group,
  (p) a phenoxy group,
  (q) a pyridyloxy group having, on the ring, the same or different 1 to 4 substituents selected from
    (i) a halogen atom, and
    (ii) a halo($C_1$-$C_6$)alkyl group,
  (r) a hydroxyl group,
  (s) a phenyl group, and
  (t) a halo($C_1$-$C_6$)alkylsulfonylamino group,
(e3) a naphthyl group,
(e4) a naphthyl group having, on the ring, the same or different 1 to 7 substituents selected from
  (a) a halogen atom,
  (b) a cyano group,
  (c) a nitro group,
  (d) a ($C_1$-$C_6$)alkyl group, and
  (e) a halo($C_1$-$C_6$)alkyl group,
(e5) a pyridyl group,
(e6) a pyridyl group having, on the ring, the same or different 1 to 4 substituents selected from
  (a) a halogen atom,
  (b) a ($C_1$-$C_6$)alkyl group,
  (c) a halo($C_1$-$C_6$)alkyl group,
  (d) a ($C_1$-$C_6$)alkylthio group,
  (e) a ($C_1$-$C_6$)alkylsulfonyl group,
  (f) a halo($C_1$-$C_6$)alkylthio group, and
  (g) a ($C_1$-$C_6$)alkoxy group,
(e7) a pyrazolyl group, or
(e8) a pyrazolyl group having, on the ring, the same or different 1 to 3 substituents selected from
  (a) a halogen atom,
  (b) a ($C_1$-$C_6$)alkyl group,
  (c) a halo($C_1$-$C_6$)alkyl group,
  (d) a ($C_1$-$C_6$)alkylthio group,
  (e) a ($C_1$-$C_6$)alkylsulfonyl group,
  (f) a ($C_1$-$C_6$)alkoxycarbonyl group,
  (g) a ($C_1$-$C_6$)alkoxy group,
  (h) a halo($C_1$-$C_6$)alkoxy group,
  (i) a ($C_1$-$C_6$)alkoxy($C_1$-$C_6$)alkoxy group,
  (j) a cyclo($C_3$-$C_6$)alkyl group,
  (k) a phenoxy group, and
  (l) a phenyl group, or
(e9) a heterocyclic group selected from following Q-1 to Q-17,

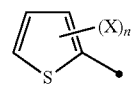
Q-1

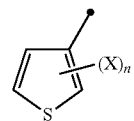
Q-2

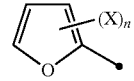
Q-3

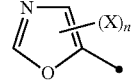
Q-4

Q-5 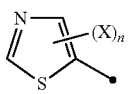

Q-6 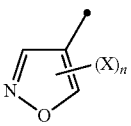

Q-7 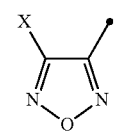

Q-8 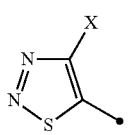

Q-9 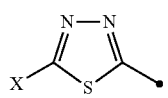

Q-10 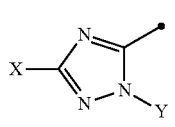

Q-11 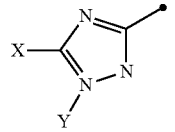

Q-12 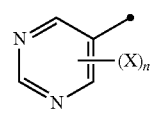

Q-13 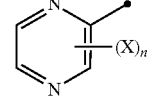

Q-14 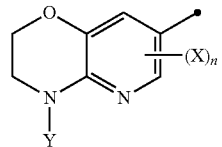

Q-15 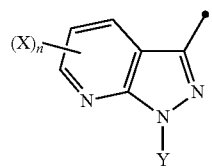

Q-16 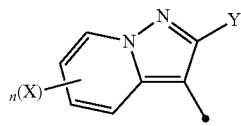

Q-17 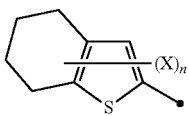

wherein X and Y are the same or different and each is
- (a) a halogen atom,
- (b) a cyano group,
- (c) a nitro group,
- (d) a ($C_1$-$C_6$)alkyl group,
- (e) a cyclo($C_3$-$C_6$)alkyl group,
- (f) a halo($C_1$-$C_6$)alkyl group,
- (g) a ($C_1$-$C_6$)alkoxy group,
- (h) a halo($C_1$-$C_6$)alkoxy group,
- (i) a ($C_1$-$C_6$)alkylthio group,
- (j) a phenyl group,
- (n) a phenyl group having, on the ring, the same or different 1 to 4 substituents selected from
  - (i) a halogen atom,
  - (ii) a ($C_1$-$C_6$)alkyl group,
  - (iii) a halo($C_1$-$C_6$)alkyl group, and
  - (iv) a ($C_1$-$C_6$)alkoxy group,
- (m) a pyridyl group,
- (o) a ($C_1$-$C_6$)alkylcarbonyl group,
- (p) a ($C_1$-$C_6$)alkoxycarbonyl group,
- (q) a mono($C_1$-$C_6$)alkylamino group,
- (r) a ($C_1$-$C_6$)alkoxy($C_1$-$C_6$)alkylamino group,
- (s) a di($C_1$-$C_6$)alkylamino group (the alkyl groups are the same or different),
- (t) a ($C_1$-$C_6$)alkoxycarbonylamino group,
- (u) a monophenylamino group,
- (v) a morpholino group, or
- (w) a piperidino group,

• is a binding position, n is an integer of 0 to 3; and

W is —O—, —S—, —$SO_2$—, or —N($R^7$)— wherein $R^7$ is a hydrogen atom, a ($C_1$-$C_6$)alkyl group or a ($C_3$-$C_6$)cycloalkyl group;

(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide,
N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide,
N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide,
N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide),
or a pharmacologically acceptable salt thereof;

[2] an anticancer agent comprising, as an active ingredient, an aminoacetonitrile compound represented by the formula (I)

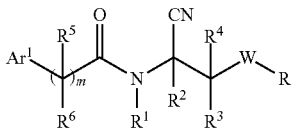

wherein
$R^1$ is
(a1) a hydrogen atom,
(a2) a $(C_1-C_6)$alkyl group,
(a3) a $(C_2-C_6)$alkenyl group,
(a4) a $(C_2-C_6)$alkynyl group, or
(a5) a $(C_3-C_6)$cycloalkyl group;
$R^2$, $R^3$, and $R^4$ are the same or different and each is
(b1) a hydrogen atom,
(b2) a $(C_1-C_6)$alkyl group, or
(b3) a $(C_3-C_6)$cycloalkyl group, or
(b4) $R^2$ and $R^3$ are optionally bonded to form a $(C_1-C_6)$ alkylene group wherein the $(C_1-C_6)$alkylene group optionally has the same or different one or more substituents selected from a halogen atom, a $(C_1-C_6)$alkyl group, and a $(C_1-C_6)$alkoxy group on the chain;
$R^5$ and $R^6$ are the same or different and each is
(c1) a hydrogen atom,
(c2) a halogen atom,
(c3) a $(C_1-C_6)$alkyl group, or
(c4) a $(C_3-C_6)$cycloalkyl group, or
(c6) $R^5$ and $R^6$ are optionally bonded to form a $(C_1-C_6)$ alkylene group;
m is 0 or 1;
R is
(d1) a phenyl group,
(d2) a phenyl group having, on the ring, the same or different 1 to 5 substituents selected from
 (a) a halogen atom,
 (b) a cyano group,
 (c) a nitro group,
 (d) a $(C_1-C_6)$alkyl group,
 (e) a halo$(C_1-C_6)$alkyl group,
 (f) a $(C_2-C_6)$alkenyl group,
 (g) a $(C_2-C_6)$alkynyl group,
 (h) a $(C_1-C_6)$alkoxy group,
 (i) a halo$(C_1-C_6)$alkoxy group,
 (j) a halo$(C_2-C_6)$alkenyloxy group,
 (k) a halo$(C_2-C_5)$alkynyloxy group,
 (l) a $(C_1-C_6)$alkylthio group,
 (m) a $(C_1-C_6)$alkylsulfonyl group,
 (n) a halo$(C_1-C_6)$alkylthio group,
 (o) a phenyl$(C_2-C_6)$alkynyl group,
 (p) a phenoxy group, and
 (q) a pyridyloxy group having, on the ring, the same or different 1 to 4 substituents selected from
  (i) a halogen atom, and
  (ii) a halo$(C_1-C_6)$alkyl group;
(d3) a naphthyl group,
(d4) a naphthyl group having, on the ring, the same or different 1 to 7 substituents selected from
 (a) a halogen atom,
 (b) a cyano group,
 (c) a nitro group,
 (d) a $(C_1-C_6)$alkyl group, and
 (e) a halo$(C_1-C_6)$alkyl group, or
(d5) a $(C_1-C_{12})$alkyl group;
$Ar^1$ is
(e1) a phenyl group,
(e2) a phenyl group having, on the ring, the same or different 1 to 5 substituents selected from
 (a) a halogen atom,
 (b) a cyano group,
 (c) a nitro group,
 (d) a $(C_1-C_6)$alkyl group,
 (e) a halo$(C_1-C_6)$alkyl group,
 (f) a $(C_2-C_6)$alkenyl group,
 (g) a $(C_2-C_6)$alkynyl group,
 (h) a $(C_1-C_6)$alkoxy group,
 (i) a halo$(C_1-C_6)$alkoxy group,
 (j) a halo$(C_2-C_6)$alkenyloxy group,
 (k) a halo$(C_2-C_6)$alkynyloxy group,
 (l) a $(C_1-C_6)$alkylthio group,
 (m) a $(C_1-C_6)$alkylsulfonyl group,
 (n) a halo$(C_1-C_6)$alkylthio group,
 (o) a phenyl$(C_2-C_6)$alkynyl group,
 (p) a phenoxy group,
 (q) a pyridyloxy group having, on the ring, the same or different 1 to 4 substituents selected from
  (i) a halogen atom, and
  (ii) a halo$(C_1-C_6)$alkyl group,
 (r) a hydroxyl group,
 (s) a phenyl group, and
 (t) a halo$(C_1-C_6)$alkylsulfonylamino group,
(e3) a naphthyl group,
(e4) a naphthyl group having, on the ring, the same or different 1 to 7 substituents selected from
 (a) a halogen atom,
 (b) a cyano group,
 (c) a nitro group,
 (d) a $(C_1-C_6)$alkyl group, and
 (e) a halo$(C_1-C_6)$alkyl group,
(e5) a pyridyl group,
(e6) a pyridyl group having, on the ring, the same or different 1 to 4 substituents selected from
 (a) a halogen atom,
 (b) a $(C_1-C_6)$alkyl group,
 (c) a halo$(C_1-C_6)$alkyl group,
 (d) a $(C_1-C_6)$alkylthio group,
 (e) a $(C_1-C_6)$alkylsulfonyl group, and
 (f) a halo$(C_1-C_6)$alkylthio group,
(e7) a pyrazolyl group, or
(e8) a pyrazolyl group having, on the ring, the same or different 1 to 3 substituents selected from
 (a) a halogen atom,
 (b) a $(C_1-C_6)$alkyl group,
 (c) a halo$(C_1-C_6)$alkyl group,
 (d) a $(C_1-C_6)$alkylthio group,
 (e) a $(C_1-C_6)$alkylsulfonyl group, and
 (f) a $(C_1-C_6)$alkoxycarbonyl group; and
W is —O—, —S—, —SO$_2$—, or —N(R$^7$)— wherein $R^7$ is a hydrogen atom, a $(C_1-C_6)$alkyl group or a $(C_3-C_6)$cycloalkyl group;
(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide,
N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide, N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide,
N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide),
or a pharmacologically acceptable salt thereof;
[3] the anticancer agent according to the above-mentioned [1], wherein
$R^1$ is
(a1) a hydrogen atom,
(a2) a $(C_1-C_6)$alkyl group, or
(a4) a $(C_2-C_6)$alkynyl group;
$R^2$, $R^3$, and $R^4$ are the same or different and each is
(b1) a hydrogen atom;
(b2) a $(C_1-C_6)$alkyl group, or
(b3) a $(C_3-C_6)$cycloalkyl group, or
(b4) $R^2$ and $R^3$ are optionally bonded to form a $(C_1-C_6)$alkylene group wherein the $(C_1-C_6)$alkylene group optionally has the same or different one or more substituents selected from a halogen atom, a $(C_1-C_6)$alkyl group, and a $(C_1-C_6)$alkoxy group on the chain;
$R^5$ and $R^6$ are the same or different and each is
(c1) a hydrogen atom,
(c2) a halogen atom, or
(c5) a $(C_1-C_6)$alkoxy group, or
(c6) $R^5$ and $R^6$ are optionally bonded to form a $(C_1-C_6)$alkylene group;
R is
(d1) a phenyl group,
(d2) a phenyl group having, on the ring, the same or different 1 to 5 substituents selected from
  (a) a halogen atom,
  (b) a cyano group,
  (c) a nitro group,
  (d) a $(C_1-C_6)$alkyl group,
  (e) a halo$(C_1-C_6)$alkyl group,
  (g) a $(C_2-C_6)$alkynyl group,
  (h) a $(C_1-C_6)$alkoxy group,
  (i) a halo$(C_1-C_6)$alkoxy group,
  (j) a halo$(C_2-C_6)$alkenyloxy group,
  (l) a $(C_1-C_6)$alkylthio group,
  (l1) a $(C_1-C_6)$alkylsulfinyl group,
  (m) a $(C_1-C_6)$alkylsulfonyl group,
  (n) a halo$(C_1-C_6)$alkylthio group,
  (n1) a halo$(C_1-C_6)$alkylsulfinyl group,
  (n2) a halo$(C_1-C_6)$alkylsulfonyl group,
  (o) a phenyl$(C_2-C_6)$alkynyl group,
  (o1) a phenyl group,
  (o2) a phenyl group having, on the ring, the same or different 1 to 5 substituents selected from
    (i) a halogen atom,
    (ii) a cyano group,
    (iii) a nitro group,
    (iv) a $(C_1-C_6)$alkyl group, and
    (v) a halo$(C_1-C_6)$alkyl group,
  (p) a phenoxy group,
  (q) a pyridyloxy group having, on the ring, the same or different 1 to 4 substituents selected from
    (i) a halogen atom, and
    (ii) a halo$(C_1-C_6)$alkyl group,
  (r) a pyridyl$(C_2-C_6)$alkynyl group,
  (s) a $(C_1-C_6)$alkylcarbonyl group,
  (t) a $(C_1-C_6)$alkoxycarbonyl group,
  (u) an aminocarbonyl group,
  (v) a $(C_1-C_6)$alkylcarbonylamino group,
  (w) a $(C_1-C_6)$alkoxycarbonylamino group,
  (x) a di$(C_1-C_6)$alkylamino group (the alkyl groups are the same or different), and
  (y) a $(C_1-C_6)$alkylaminocarbonylamino group,
(d3) a naphthyl group,
(d6) a pyridyl group,
(d7) a pyridyl group having, on the ring, the same or different 1 to 4 substituents selected from
  (a) a halogen atom,
  (b) a cyano group,
  (c) a nitro group,
  (d) a $(C_1-C_6)$alkyl group, and
  (e) a halo$(C_1-C_6)$alkyl group;
(d9) a pyrazinyl group having, on the ring, the same or different 1 to 3 substituents selected from
  (a) a halogen atom,
  (b) a cyano group,
  (c) a nitro group,
  (d) a $(C_1-C_6)$alkyl group, and
  (e) a halo$(C_1-C_6)$alkyl group,
(d11) a thiazolyl group having, on the ring, the same or different 1 to 2 substituents selected from
  (a) a halogen atom,
  (b) a cyano group,
  (c) a nitro group,
  (d) a $(C_1-C_6)$alkyl group, and
  (e) a halo$(C_1-C_6)$alkyl group, or
(d13) a pyrazolyl group having, on the ring, the same or different 1 to 3 substituents selected from
  (a) a halogen atom,
  (b) a cyano group,
  (c) a nitro group,
  (d) a $(C_1-C_6)$alkyl group, and
  (e) a halo$(C_1-C_6)$alkyl group;
$Ar^1$ is
(e1) a phenyl group,
(e2) a phenyl group having, on the ring, the same or different 1 to 5 substituents selected from
  (a) a halogen atom,
  (b) a cyano group,
  (c) a nitro group,
  (d) a $(C_1-C_6)$alkyl group,
  (e) a halo$(C_1-C_6)$alkyl group,
  (f) a $(C_2-C_6)$alkenyl group,
  (g) a $(C_2-C_6)$alkynyl group,
  (h) a $(C_1-C_6)$alkoxy group,
  (i) a halo$(C_1-C_6)$alkoxy group,
  (j) a halo$(C_2-C_6)$alkenyloxy group,
  (k) a halo$(C_2-C_6)$alkynyloxy group,
  (l) a $(C_1-C_6)$alkylthio group,
  (m) a $(C_1-C_6)$alkylsulfonyl group,
  (n) a halo$(C_1-C_6)$alkylthio group,
  (o) a phenyl$(C_2-C_6)$alkynyl group,
  (p) a phenoxy group,
  (q) a pyridyloxy group having, on the ring, the same or different 1 to 4 substituents selected from
    (i) a halogen atom, and
    (ii) a halo$(C_1-C_6)$alkyl group,
  (r) a hydroxyl group,
  (s) a phenyl group, and
  (t) a halo$(C_1-C_6)$alkylsulfonylamino group, (e3) a naphthyl group,
(e5) a pyridyl group,
(e6) a pyridyl group having, on the ring, the same or different 1 to 4 substituents selected from
  (a) a halogen atom,
  (b) a ($C_1$-$C_6$)alkyl group,
  (c) a halo($C_1$-$C_6$)alkyl group,
  (d) a ($C_1$-$C_6$)alkylthio group,
  (e) a ($C_1$-$C_6$)alkylsulfonyl group,
  (f) a halo($C_1$-$C_6$)alkylthio group, and
  (g) a ($C_1$-$C_6$)alkoxy group,
(e8) a pyrazolyl group having, on the ring, the same or different 1 to 3 substituents selected from
  (a) a halogen atom,
  (b) a ($C_1$-$C_6$)alkyl group,
  (c) a halo($C_1$-$C_6$)alkyl group,
  (d) a ($C_1$-$C_6$)alkylthio group,
  (e) a ($C_1$-$C_6$)alkylsulfonyl group,
  (f) a ($C_1$-$C_6$)alkoxycarbonyl group
  (g) a ($C_1$-$C_6$)alkoxy group,
  (h) a halo($C_1$-$C_5$)alkoxy group,
  (i) a ($C_1$-$C_6$)alkoxy($C_1$-$C_6$)alkoxy group,
  (j) a cyclo($C_3$-$C_6$)alkyl group,
  (k) a phenoxy group, and
  (l) a phenyl group, or
(e9) a heterocyclic group selected from following Q-1 to Q-17,

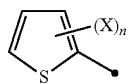
Q-1

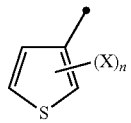
Q-2

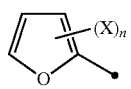
Q-3

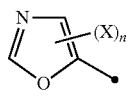
Q-4

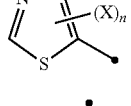
Q-5

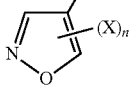
Q-6

-continued

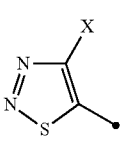
Q-7

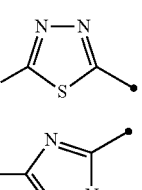
Q-8

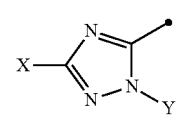
Q-9

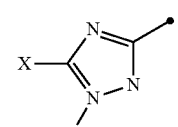
Q-10

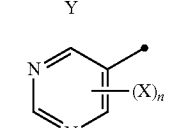
Q-11

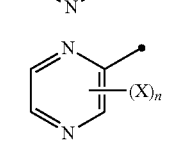
Q-12

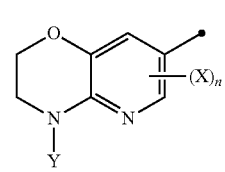
Q-13

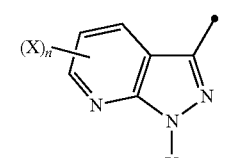
Q-14

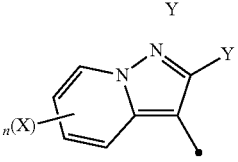
Q-15

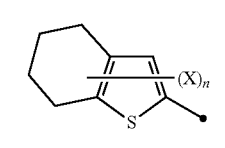
Q-16

Q-17 wherein X and Y are the same or different and each is
  (a) a halogen atom,
  (b) a cyano group,
  (c) a nitro group,
  (d) a ($C_1$-$C_6$)alkyl group,
  (e) a cyclo($C_3$-$C_6$)alkyl group,
  (f) a halo($C_1$-$C_6$)alkyl group,
  (g) a ($C_1$-$C_6$)alkoxy group,
  (h) a halo($C_1$-$C_6$)alkoxy group,
  (i) a ($C_1$-$C_6$)alkylthio group,
  (j) a phenyl group, (n) a phenyl group having, on the ring, the same or different 1 to 4 substituents selected from
  (i) a halogen atom,
  (ii) a $(C_1\text{-}C_6)$alkyl group,
  (iii) a halo$(C_1\text{-}C_6)$alkyl group, and
  (iv) a $(C_1\text{-}C_6)$alkoxy group,
(m) a pyridyl group,
(o) a $(C_1\text{-}C_6)$alkylcarbonyl group,
(p) a $(C_1\text{-}C_6)$alkoxycarbonyl group,
(q) a mono$(C_1\text{-}C_6)$alkylamino group,
(r) a $(C_1\text{-}C_6)$alkoxy$(C_1\text{-}C_6)$alkylamino group,
(s) a di$(C_1\text{-}C_6)$alkylamino group (the alkyl groups are the same or different),
(t) a $(C_1\text{-}C_6)$alkoxycarbonylamino group,
(u) a monophenylamino group,
(v) a morpholino group, or
(w) a piperidino group,
• is a binding position,
n is an integer of 0 to 3; and
W is —O—, —S—, —SO$_2$—, or —N(R$^7$)— wherein R$^7$ is a $(C_1\text{-}C_6)$alkyl group;
[4] the anticancer agent according to the above-mentioned [1] or [2], wherein m is 1;
[5] the anticancer agent according to the above-mentioned [1] or [2], wherein when m is 0, then Ar$^1$ is
(e2) a phenyl group having, on the ring, the same or different 1 to 5 substituents selected from
  (c) a nitro group,
  (e') a halo$(C_2\text{-}C_6)$alkyl group,
  (f) a $(C_2\text{-}C_6)$alkenyl group,
  (g) a $(C_2\text{-}C_6)$alkynyl group,
  (i') a halo$(C_2\text{-}C_6)$alkoxy group,
  (j) a halo$(C_2\text{-}C_6)$alkenyloxy group,
  (k) a halo$(C_2\text{-}C_6)$alkynyloxy group,
  (l) a $(C_1\text{-}C_6)$alkylthio group,
  (m) a $(C_1\text{-}C_6)$alkylsulfonyl group,
  (n') a halo$(C_2\text{-}C_6)$alkylthio group,
  (o) a phenyl$(C_2\text{-}C_6)$alkynyl group,
  (p) a phenoxy group,
  (q) a pyridyloxy group having, on the ring, the same or different 1 to 4 substituents selected from
    (i) a halogen atom, and
    (ii) a halo$(C_1\text{-}C_6)$alkyl group,
  (r) a hydroxyl group,
  (s) a phenyl group, and
  (t) a halo$(C_1\text{-}C_6)$alkylsulfonylamino group,
(e3) a naphthyl group,
(e4) a naphthyl group having, on the ring, the same or different 1 to 7 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group,
(e5) a pyridyl group,
(e6) a pyridyl group having, on the ring, the same or different 1 to 4 substituents selected from
  (a) a halogen atom,
  (b) a $(C_1\text{-}C_6)$alkyl group,
  (c) a halo$(C_1\text{-}C_6)$alkyl group,
  (d) a $(C_1\text{-}C_6)$alkylthio group,
  (e) a $(C_1\text{-}C_6)$alkylsulfonyl group, and
  (f) a halo$(C_1\text{-}C_6)$alkylthio group,
(e7) a pyrazolyl group, or
(e8) a pyrazolyl group having, on the ring, the same or different 1 to 3 substituents selected from
  (a) a halogen atom,
  (b) a $(C_1\text{-}C_6)$alkyl group,
  (c) a halo$(C_1\text{-}C_6)$alkyl group,
  (d) a $(C_1\text{-}C_6)$alkylthio group,
  (e) a $(C_1\text{-}C_6)$alkylsulfonyl group, and
  (f) a $(C_1\text{-}C_6)$alkoxycarbonyl group;
[6] the anticancer agent according to the above-mentioned [1] or [2], wherein when m is 0, then R is
(d2) a phenyl group having, on the ring, the same or different 1 to 5 substituents selected from
  (c) a nitro group,
  (e') a halo$(C_2\text{-}C_6)$alkyl group,
  (f) a $(C_2\text{-}C_6)$alkenyl group,
  (g) a $(C_2\text{-}C_6)$alkynyl group,
  (h) a $(C_1\text{-}C_6)$alkoxy group,
  (i) a halo$(C_1\text{-}C_6)$alkoxy group,
  (j) a halo$(C_2\text{-}C_6)$alkenyloxy group,
  (k) a halo$(C_2\text{-}C_6)$alkynyloxy group,
  (l) a $(C_1\text{-}C_6)$alkylthio group,
  (m) a $(C_1\text{-}C_6)$alkylsulfonyl group,
  (n) a halo$(C_1\text{-}C_6)$alkylthio group,
  (o) a phenyl$(C_2\text{-}C_6)$alkynyl group,
  (p) a phenoxy group, and
  (q) a pyridyloxy group having, on the ring, the same or different 1 to 4 substituents selected from
    (i) a halogen atom, and
    (ii) a halo$(C_1\text{-}C_6)$alkyl group,
(d3) a naphthyl group,
(d4) a naphthyl group having, on the ring, the same or different 1 to 7 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group, or
(d5) a $(C_1\text{-}C_{12})$alkyl group;
[7] the anticancer agent according to the above-mentioned [1] or [2], wherein when m is 0, then R$^1$ is
(a2) a $(C_1\text{-}C_6)$alkyl group,
(a3) a $(C_2\text{-}C_6)$alkenyl group,
(a4) a $(C_2\text{-}C_6)$alkynyl group, or
(a5) a $(C_3\text{-}C_6)$cycloalkyl group;
[8] the anticancer agent according to the above-mentioned [1] or [2], wherein when m is 0, then R$^3$ is
(b2) a $(C_1\text{-}C_6)$alkyl group, or
(b3) a $(C_3\text{-}C_6)$cycloalkyl group, or
(b4) R$^2$ and R$^3$ are bonded to form a $(C_1\text{-}C_6)$alkylene group;
[9] the anticancer agent according to the above-mentioned [1] or [2], wherein
R$^1$ is
(a1) a hydrogen atom, or
(a4) a $(C_2\text{-}C_6)$alkynyl group;
R$^2$, R$^3$, and R$^4$ are the same or different and each is
(b1) a hydrogen atom, or
(b2) a $(C_1\text{-}C_6)$alkyl group, or
(b4) R$^2$ and R$^3$ are optionally bonded to form a $(C_1\text{-}C_6)$ alkylene group;
R$^5$ and R$^6$ are the same or different and each is
(c1) a hydrogen atom, or
(c6) R$^5$ and R$^6$ are optionally bonded to form a $(C_1\text{-}C_6)$ alkylene group;
R is
(d1) a phenyl group,
(d2) a phenyl group having, on the ring, the same or different 1 to 5 substituents selected from
  (a) a halogen atom,
  (b) a cyano group, (c) a nitro group,
(d) a $(C_1-C_6)$alkyl group,
(e) a halo$(C_1-C_6)$alkyl group,
(g) a $(C_2-C_6)$alkynyl group,
(i) a halo$(C_1-C_6)$alkoxy group,
(j) a halo$(C_2-C_6)$alkenyloxy group,
(l) a $(C_1-C_6)$alkylthio group,
(m) a $(C_1-C_6)$alkylsulfonyl group,
(n) a halo$(C_1-C_6)$alkylthio group,
(o) a phenyl$(C_2-C_6)$alkynyl group,
(p) a phenoxy group, and
(q) a pyridyloxy group having, on the ring, the same or different 1 to 4 substituents selected from
   (i) a halogen atom, and
   (ii) a halo$(C_1-C_6)$alkyl group,
(d3) a naphthyl group, or
(d5) a $(C_1-C_{12})$alkyl group;
$Ar^1$ is
(e1) a phenyl group,
(e2) a phenyl group having, on the ring, the same or different 1 to 5 substituents selected from
   (a) a halogen atom,
   (b) a cyano group,
   (c) a nitro group,
   (d) a $(C_1-C_6)$alkyl group,
   (e) a halo$(C_1-C_6)$alkyl group,
   (h) a $(C_1-C_6)$alkoxy group,
   (i) a halo$(C_1-C_6)$alkoxy group,
   (n) a halo$(C_1-C_6)$alkylthio group,
   (q) a pyridyloxy group having, on the ring, the same or different 1 to 4 substituents selected from
      (i) a halogen atom, and
      (ii) a halo$(C_1-C_6)$alkyl group,
   (r) a hydroxyl group,
   (s) a phenyl group, and
   (t) a halo$(C_1-C_6)$alkylsulfonylamino group,
(e3) a naphthyl group,
(e5) a pyridyl group,
(e6) a pyridyl group having, on the ring, the same or different 1 to 4 substituents selected from
   (a) a halogen atom,
   (b) a $(C_1-C_6)$alkyl group,
   (c) a halo$(C_1-C_6)$alkyl group,
   (d) a $(C_1-C_6)$alkylthio group,
   (e) a $(C_1-C_6)$alkylsulfonyl group, and
   (f) a halo$(C_1-C_6)$alkylthio group, or
(e8) a pyrazolyl group having, on the ring, the same or different 1 to 3 substituents selected from
   (a) a halogen atom,
   (b) a $(C_1-C_6)$alkyl group,
   (c) a halo$(C_1-C_6)$alkyl group,
   (d) a $(C_1-C_6)$alkylthio group,
   (e) a $(C_1-C_6)$alkylsulfonyl group, and
   (f) a $(C_1-C_6)$alkoxycarbonyl group; and
W is —O—;

[10] the anticancer agent according to any one of the above-mentioned [1] to [9], wherein the cancer is selected from colon cancer, lung cancer, mesothelioma, pancreatic cancer, stomach cancer, breast cancer, ovarian cancer, prostate cancer, liver cancer, thyroid cancer, renal cancer, uterine cancer, brain tumor, melanoma, sarcoma, urinary bladder cancer, blood cancer, head and neck cancer, cervix cancer, esophageal cancer, gallbladder cancer, splenic cancer, testicular cancer, peripheral nerve cancer, and skin cancer;

[11] the anticancer agent according to any one of the above-mentioned [1] to [9], wherein the cancer is selected from brain tumor, peripheral nerve cancer, and ovarian cancer;

[12] a method for the treatment of cancer, comprising administering an effective amount of the aminoacetonitrile compound represented by the formula (I) of the above-mentioned [1] or [2]
(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide,
N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide,
N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide,
N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide), or a pharmacologically acceptable salt thereof to a mammal;

[13] use of the aminoacetonitrile compound represented by the formula (I) of the above-mentioned [1] or [2]
(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide,
N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide,
N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide,
N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide), or a pharmacologically acceptable salt thereof, for the production of an anticancer agent;

[14] the aminoacetonitrile compound represented by the formula (I) of the above-mentioned [1] or [2]
(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide, N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide,
N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide,
N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide), or a pharmacologically acceptable salt thereof, for use in the treatment of cancer;
and the like.

Effect of the Invention

According to the present invention, such aminoacetonitrile compound or a pharmacologically acceptable salt thereof can provide a cell growth inhibitor or an anticancer agent containing the same as an active ingredient.

DESCRIPTION OF EMBODIMENTS

In definition of the aminoacetonitrile compound (I) of the present invention, "halo" means a "halogen atom", and shows a fluorine atom, a chlorine atom, a bromine atom, or an iodine atom.

The "$(C_1-C_6)$alkyl group" is, for example, a straight or branched chain alkyl group having a carbon number of 1 to 6, such as a methyl group, an ethyl group, a normal propyl group, an isopropyl group, a normal butyl group, an isobutyl group, a secondary butyl group, a tertiary butyl group, a normal pentyl group, an isopentyl group, a normal hexyl group and the like, the "$(C_2-C_6)$alkyl group" is, for example, a straight or branched chain alkyl group having a carbon number of 2 to 6, such as an ethyl group, a normal propyl group, an isopropyl group, a normal butyl group, an isobutyl group, a secondary butyl group, a tertiary butyl group, a normal pentyl group, an isopentyl group, a normal hexyl group and the like, the "$(C_1-C_{12})$alkyl group" is, for example, a straight or branched chain alkyl group having a carbon number of 1 to 12 such as a methyl group, an ethyl group, a normal propyl group, a normal pentyl group, a normal hexyl group, a normal octyl group, a normal dodecanyl group and the like, the "$(C_2-C_6)$alkenyl group" is, for example, a straight or branched chain alkenyl group having a carbon number of 2 to 6 such as a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group and the like, and the "$(C_2-C_6)$alkynyl group" is, for example, a straight or branched chain alkynyl group having a carbon number of 2 to 6 such as an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3,3-dimethyl-1-butynyl group and the like.

The "$(C_3-C_6)$cycloalkyl group" is, for example, a cyclic alkyl group having a carbon number of 3 to 6, such as a cyclopropyl group, a cyclobutyl group, a cyclopentyl group, a cyclohexyl group and the like, the "$(C_1-C_6)$alkoxy group" is, for example, a straight or branched chain alkoxy group having a carbon number of 1 to 6, such as a methoxy group, an ethoxy group, a normal propoxy group, an isopropoxy group, a normal butoxy group, a secondary butoxy group, a tertiary butoxy group, a normal pentyloxy group, a isopentyloxy group, a tertiary pentyloxy group, a neopentyloxy group, a 2,3-dimethylpropyloxy group, a 1-ethylpropyloxy group, a 1-methylbutyloxy group, a normal hexyloxy group and the like, the "$(C_2-C_6)$alkoxy group" is, for example, a straight or branched chain alkoxy group having a carbon number of 2 to 6, such as an ethoxy group, a normal propoxy group, an isopropoxy group, a normal butoxy group, a secondary butoxy group, a tertiary butoxy group, a normal pentyloxy group, an isopentyloxy group, a tertiary pentyloxy group, a neopentyloxy group, a 2,3-dimethylpropyloxy group, a 1-ethylpropyloxy group, a 1-methylbutyloxy group, a normal hexyloxy group and the like, the "$(C_2-C_6)$alkenyloxy group" is, for example, a straight or branched chain alkenyloxy group having a carbon number of 2 to 6, such as a propenyloxy group, a butenyloxy group, a pentenyloxy group, a hexenyloxy group and the like, and the "$(C_2-C_6)$alkynyloxy group" is, for example, a straight or branched chain alkynyloxy group having a carbon number of 2 to 6, such as a propynyloxy group, a butynyloxy group, a pentynyloxy group, a hexynyloxy group and the like.

The "$(C_1-C_6)$alkylthio group" is, for example, a straight or branched chain alkylthio group having a carbon number of 1 to 6, such as a methylthio group, an ethylthio group, a normal propylthio group, an isopropylthio group, a normal butylthio group, a secondary butylthio group, a tertiary butylthio group, a normal pentylthio group, an isopentylthio group, a normal hexylthio group and the like, the "$(C_2-C_6)$alkylthio group" is, for example, a straight or branched chain alkylthio group having a carbon number of 2 to 6, such as an ethylthio group, a normal propylthio group, an isopropylthio group, a normal butylthio group, a secondary butylthio group, a tertiary butylthio group, a normal pentylthio group, an isopentylthio group, a normal hexylthio group and the like, the "$(C_1-C_6)$alkylsulfinyl group" is, for example, a straight or branched chain alkylsulfinyl group having a carbon number of 1 to 6, such as a methylsulfinyl group, an ethylsulfinyl group, a normal propylsulfinyl group, an isopropylsulfinyl group, a normal butylsulfinyl group, a secondary butylsulfinyl group, a tertiary butylsulfinyl group, a normal pentylsulfinyl group, a normal hexylsulfinyl group and the like, and the "$(C_1-C_6)$alkylsulfonyl group" is, for example, a straight or branched chain alkylsulfonyl group having a carbon number of 1 to 6, such as a methylsulfonyl group, an ethylsulfonyl group, a normal propylsulfonyl group, an isopropylsulfonyl group, a normal butylsulfonyl group, a tertiary butylsulfonyl group, a normal pentylsulfonyl group, an isopentylsulfonyl group, a tertiary pentylsulfonyl group, a neopentylsulfonyl group, a normal hexylsulfonyl group and the like.

The "$(C_2-C_6)$alkenylthio group" is, for example, a straight or branched chain alkenylthio group having a carbon number of 2 to 6, such as a propenylthio group, a butenylthio group, a pentenylthio group, a hexenylthio group and the like, and the "$(C_2\text{-}C_6)$alkynylthio group" is, for example, a straight or branched chain alkynylthio group having a carbon number of 2 to 6, such as a propynylthio group, a butynylthio group, a pentynylthio group, a hexynylthio group and the like.

The "$(C_2\text{-}C_6)$alkenylsulfinyl group" is, for example, a straight or branched chain alkenylsulfinyl group having a carbon number of 2 to 6, such as a propenylsulfinyl group, a butenylsulfinyl group, a pentenylsulfinyl group, a hexenylsulfinyl group and the like, and the "$(C_2\text{-}C_6)$alkynylsulfinyl group" is, for example, a straight or branched chain alkynylsulfinyl group having a carbon number of 2 to 6, such as a propynylsulfinyl group, a butynylsulfinyl group, a pentynylsulfinyl group, a hexynylsulfinyl group and the like.

The "$(C_2\text{-}C_6)$alkenylsulfonyl group" is, for example, a straight or branched chain alkenylsulfonyl group having a carbon number of 2 to 6, such as a propenylsulfonyl group, a butenylsulfonyl group, a pentenylsulfonyl group, a hexenylsulfonyl group and the like, and the "$(C_2\text{-}C_6)$alkynylsulfonyl group" is, for example, a straight or branched chain alkynylsulfonyl group having a carbon number of 2 to 6, such as a propynylsulfonyl group, a butynylsulfonyl group, a pentynylsulfonyl group, a hexynylsulfonyl group and the like.

The above-mentioned "$(C_1\text{-}C_6)$alkyl group", "$(C_2\text{-}C_6)$alkyl group", "$(C_1\text{-}C_{12})$alkyl group", "$(C_2\text{-}C_6)$alkenyl group", "$(C_2\text{-}C_6)$alkynyl group", "$(C_3\text{-}C_6)$cycloalkyl group", "$(C_1\text{-}C_6)$alkoxy group", "$(C_2\text{-}C_6)$alkoxy group", "$(C_2\text{-}C_6)$alkenyloxy group", "$(C_2\text{-}C_6)$alkynyloxy group", "$(C_1\text{-}C_6)$alkylthio group", "$(C_2\text{-}C_6)$alkylthio group", "$(C_1\text{-}C_6)$alkylsulfinyl group", "$(C_1\text{-}C_6)$alkylsulfonyl group", "$(C_2\text{-}C_6)$alkenylthio group", "$(C_2\text{-}C_6)$alkynylthio group", "$(C_2\text{-}C_6)$alkenylsulfinyl group", "$(C_2\text{-}C_6)$alkynylsulfinyl group", "$(C_2\text{-}C_6)$alkenylsulfonyl group" and "$(C_2\text{-}C_6)$alkynylsulfonyl group" may be substituted by one or more halogen atoms at substitutable position(s). When substituted by two or more halogen atoms, the halogen atoms may be the same or different.

They are each indicated as "halo$(C_1\text{-}C_6)$alkyl group", "halo$(C_2\text{-}C_6)$alkyl group", "halo$(C_1\text{-}C_{12})$alkyl group", "halo$(C_2\text{-}C_6)$alkenyl group", "halo$(C_2\text{-}C_6)$alkynyl group", "halo$(C_3\text{-}C_6)$cycloalkyl group", "halo$(C_1\text{-}C_6)$alkoxy group", "halo$(C_2\text{-}C_6)$alkoxy group", "halo$(C_2\text{-}C_6)$alkenyloxy group", "halo$(C_2\text{-}C_6)$alkynyloxy group", "halo$(C_1\text{-}C_6)$alkylthio group", "halo$(C_2\text{-}C_6)$alkylthio group", "halo$(C_1\text{-}C_6)$alkylsulfinyl group", "halo$(C_1\text{-}C_6)$alkylsulfonyl group", "halo$(C_2\text{-}C_6)$alkenylthio group", "halo$(C_2\text{-}C_6)$alkynylthio group", "halo$(C_2\text{-}C_6)$alkenylsulfinyl group", "halo$(C_2\text{-}C_6)$alkynylsulfinyl group", "halo$(C_2\text{-}C_6)$alkenylsulfonyl group" and "halo$(C_2\text{-}C_6)$alkynylsulfonyl group".

In addition, the expressions such as "$(C_1\text{-}C_6)$", "$(C_2\text{-}C_6)$", "$(C_3\text{-}C_6)$" and the like show the range of the carbon numbers of various substituents.

Furthermore, the above-mentioned definition applies to groups bonded to the above-mentioned substituents. For example, a phenyl$(C_2\text{-}C_6)$alkynyl group is a group wherein a phenyl group is bound to any position of a $(C_2\text{-}C_6)$alkynyl group.

The "$(C_1\text{-}C_6)$alkylene group" is a group formed by two adjacent substituents in conjunction and, for example, a methylene group, an ethylene group, a propylene group, a butylene group, a pentylene group, a hexylene group and the like can be mentioned.

Examples of "heterocyclic group" include a monocyclic aromatic heterocyclic group such as furyl, thienyl, pyridyl, pyrimidinyl, pyrazinyl, pyrazolyl, thiazolyl, oxazolyl, isoxazolyl, oxadiazolyl, thiadiazolyl, triazolyl and the like; a fused heterocyclic group such as 3,4-dihydropyrido[3,2-b][1,4]oxazine, pyrazolo[3,4-b]pyridine, pyrazolo[1,5-a]pyridine, 4,5,6,7-tetrahydrobenzo[b]thiophene and the like, and the like.

The aminoacetonitrile compound represented by the formula (I), which is the active ingredient of the anticancer agent of the present invention, does not include the following compounds.

N-[(1S)-1-cyano-2-(5-cyano-2-trifluoromethylphenoxy)-1-methyl-ethyl]-4-trifluoromethylsulfanylbenzamide, N-[(1R)-1-cyano-2-(5-cyano-2-trifluoromethylphenoxy)-1-methyl-ethyl]-4-trifluoromethylsulfanylbenzamide, N-[1-cyano-2-(5-cyano-2-trifluoromethylphenoxy)-1-methyl-ethyl]-4-trifluoromethylsulfanylbenzamide, N-[2-(2-chlorophenoxy)-1-cyano-1-methyl-ethyl]-4-trifluoromethylbenzamide, N-[1-cyano-2-(2-trifluoromethylphenoxy)-1-methyl-ethyl]-4-trifluoromethylbenzamide, N-[1-cyano-2-(2-trifluoromethylphenoxy)-1-methyl-ethyl]-4-trifluoromethoxybenzamide, N-[1-cyano-2-(2,5-dichlorophenoxy)-1-methyl-ethyl]-4-trifluoromethoxybenzamide, N-[2-(2-chloro-5-fluorophenoxy)-1-cyano-1-methyl-ethyl]-4-trifluoromethoxybenzamide, N-[2-(2-chloro-4-fluorophenoxy)-1-cyano-1-methyl-ethyl]-4-trifluoromethoxybenzamide, N-[2-(2-bromo-4,5-difluorophenoxy)-1-cyano-1-methyl-ethyl]-4-trifluoromethoxybenzamide, and N-[1-cyano-2-(4,5-difluoro-2-trifluoromethylphenoxy)-1-methyl-ethyl]-4-trifluoromethoxybenzamide.

One preferable embodiment of the aminoacetonitrile compound represented by the formula (I), which is the active ingredient of the anticancer agent of the present invention, is a compound wherein $R^1$ is (a1) a hydrogen atom, (a2) a $(C_1\text{-}C_6)$alkyl group, or (a4) a $(C_2\text{-}C_6)$alkynyl group;

$R^2$, $R^3$ and $R^4$ are the same or different and each is (b1) a hydrogen atom;

(b2) a $(C_1\text{-}C_6)$alkyl group, or (b3) a $(C_3\text{-}C_6)$cycloalkyl group, or (b4) $R^2$ and $R^3$ are optionally bonded to form a $(C_1\text{-}C_6)$alkylene group wherein the $(C_1\text{-}C_6)$alkylene group optionally has the same or different one or more substituents selected from a halogen atom, a $(C_1\text{-}C_6)$alkyl group, and a $(C_1\text{-}C_6)$alkoxy group on the chain;

$R^5$ and $R^6$ are the same or different and each is (c1) a hydrogen atom, (c2) a halogen atom, or (c5) a $(C_1\text{-}C_6)$alkoxy group, or (c6) $R^5$ and $R^6$ are optionally bonded to form a $(C_1\text{-}C_6)$alkylene group;

R is (d1) a phenyl group, (d2) a phenyl group having, on the ring, the same or different 1 to 5 substituents selected from (a) a halogen atom, (b) a cyano group, (c) a nitro group, (d) a $(C_1\text{-}C_6)$alkyl group, (e) a halo$(C_1\text{-}C_6)$alkyl group, (g) a $(C_2\text{-}C_6)$alkynyl group, (h) a $(C_1$-$C_6)$alkoxy group,
(i) a halo$(C_1$-$C_6)$alkoxy group,
(j) a halo$(C_2$-$C_6)$alkenyloxy group,
(l) a $(C_1$-$C_6)$alkylthio group,
(l1) a $(C_1$-$C_6)$alkylsulfinyl group,
(m) a $(C_1$-$C_6)$alkylsulfonyl group,
(n) a halo$(C_1$-$C_6)$alkylthio group,
(n1) a halo$(C_1$-$C_6)$alkylsulfinyl group,
(n2) a halo$(C_1$-$C_6)$alkylsulfonyl group,
(o) a phenyl$(C_2$-$C_6)$alkynyl group,
(o1) a phenyl group,
(o2) a phenyl group having, on the ring, the same or different 1 to 5 substituents selected from
  (i) a halogen atom,
  (ii) a cyano group,
  (iii) a nitro group,
  (iv) a $(C_1$-$C_6)$alkyl group, and
  (v) a halo$(C_1$-$C_6)$alkyl group,
(p) a phenoxy group,
(q) a pyridyloxy group having, on the ring, the same or different 1 to 4 substituents selected from
  (i) a halogen atom, and
  (ii) a halo$(C_1$-$C_6)$alkyl group,
(r) a pyridyl$(C_2$-$C_6)$alkynyl group,
(s) a $(C_1$-$C_6)$alkylcarbonyl group,
(t) a $(C_1$-$C_6)$alkoxycarbonyl group,
(u) an aminocarbonyl group,
(v) a $(C_1$-$C_6)$alkylcarbonylamino group,
(w) a $(C_1$-$C_6)$alkoxycarbonylamino group,
(x) a di$(C_1$-$C_6)$alkylamino group (the alkyl groups are the same or different), and
(y) a $(C_1$-$C_6)$alkylaminocarbonylamino group,
(d3) a naphthyl group,
(d6) a pyridyl group,
(d7) a pyridyl group having, on the ring, the same or different 1 to 4 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group;
(d9) a pyrazinyl group having, on the ring, the same or different 1 to 3 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group,
(d11) a thiazolyl group having, on the ring, the same or different 1 to 2 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group, or
(d13) a pyrazolyl group having, on the ring, the same or different 1 to 3 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group;
$Ar^1$ is
(e1) a phenyl group,
(e2) a phenyl group having, on the ring, the same or different 1 to 5 substituents selected from
  (a) a halogen atom,
  (b) a cyano group,
  (c) a nitro group,
  (d) a $(C_1$-$C_6)$alkyl group,
  (e) a halo$(C_1$-$C_6)$alkyl group,
  (f) a $(C_2$-$C_6)$alkenyl group,
  (g) a $(C_2$-$C_6)$alkynyl group,
  (h) a $(C_1$-$C_6)$alkoxy group,
  (i) a halo$(C_1$-$C_6)$alkoxy group,
  (j) a halo$(C_2$-$C_6)$alkenyloxy group,
  (k) a halo$(C_2$-$C_6)$alkynyloxy group,
  (l) a $(C_1$-$C_6)$alkylthio group,
  (m) a $(C_1$-$C_6)$alkylsulfonyl group,
  (n) a halo$(C_1$-$C_6)$alkylthio group,
  (o) a phenyl$(C_2$-$C_6)$alkynyl group,
  (p) a phenoxy group,
  (q) a pyridyloxy group having, on the ring, the same or different 1 to 4 substituents selected from
    (i) a halogen atom, and
    (ii) a halo$(C_1$-$C_6)$alkyl group,
  (r) a hydroxyl group,
  (s) a phenyl group, and
  (t) a halo$(C_1$-$C_6)$alkylsulfonylamino group,
(e3) a naphthyl group,
(e5) a pyridyl group,
(e6) a pyridyl group having, on the ring, the same or different 1 to 4 substituents selected from
  (a) a halogen atom,
  (b) a $(C_1$-$C_6)$alkyl group,
  (c) a halo$(C_1$-$C_6)$alkyl group,
  (d) a $(C_1$-$C_6)$alkylthio group,
  (e) a $(C_1$-$C_6)$alkylsulfonyl group,
  (f) a halo$(C_1$-$C_6)$alkylthio group, and
  (g) a $(C_1$-$C_6)$alkoxy group, or
(e8) a pyrazolyl group having, on the ring, the same or different 1 to 3 substituents selected from
  (a) a halogen atom,
  (b) a $(C_1$-$C_6)$alkyl group,
  (c) a halo$(C_1$-$C_6)$alkyl group,
  (d) a $(C_1$-$C_6)$alkylthio group,
  (e) a $(C_1$-$C_6)$alkylsulfonyl group,
  (f) a $(C_1$-$C_6)$alkoxycarbonyl group,
  (g) a $(C_1$-$C_6)$alkoxy group,
  (h) a halo$(C_1$-$C_6)$alkoxy group,
  (i) a $(C_1$-$C_6)$alkoxy$(C_1$-$C_6)$alkoxy group,
  (j) a cyclo$(C_3$-$C_6)$alkyl group,
  (k) a phenoxy group, and
  (l) a phenyl group, or
(e9) a heterocyclic group selected from following Q-1 to Q-17,

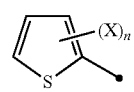
Q-1

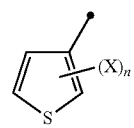
Q-2

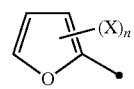
Q-3

Q-4 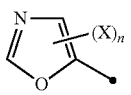

Q-5 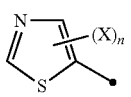

Q-6 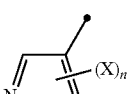

Q-7 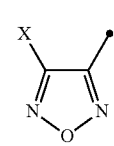

Q-8 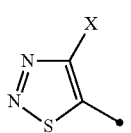

Q-9 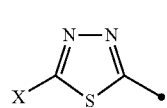

Q-10 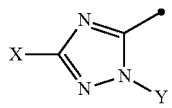

Q-11 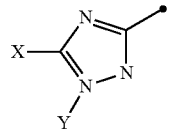

Q-12 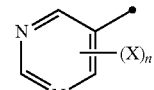

Q-13 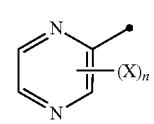

Q-14 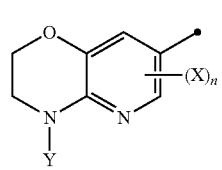

Q-15 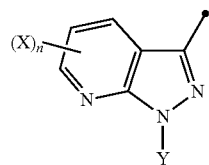

Q-16 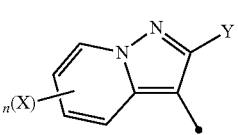

Q-17 wherein X and Y are the same or different and each is
(a) a halogen atom,
(b) a cyano group,
(c) a nitro group,
(d) a ($C_1$-$C_6$)alkyl group,
(e) a cyclo($C_3$-$C_6$)alkyl group,
(f) a halo($C_1$-$C_6$)alkyl group,
(g) a ($C_1$-$C_6$)alkoxy group,
(h) a halo($C_1$-$C_6$)alkoxy group,
(i) a ($C_1$-$C_6$)alkylthio group,
(j) a phenyl group,
(n) a phenyl group having, on the ring, the same or different 1 to 4 substituents selected from
  (i) a halogen atom,
  (ii) a ($C_1$-$C_6$)alkyl group,
  (iii) a halo($C_1$-$C_6$)alkyl group, and
  (iv) a ($C_1$-$C_6$)alkoxy group,
(m) a pyridyl group,
(o) a ($C_1$-$C_6$)alkylcarbonyl group,
(p) a ($C_1$-$C_6$)alkoxycarbonyl group,
(q) a mono($C_1$-$C_6$)alkylamino group,
(r) a ($C_1$-$C_6$)alkoxy($C_1$-$C_6$)alkylamino group,
(s) a di($C_1$-$C_6$)alkylamino group (the alkyl groups are the same or different),
(t) a ($C_1$-$C_6$)alkoxycarbonylamino group,
(u) a monophenylamino group,
(v) a morpholino group, or
(w) a piperidino group,
• is a binding position,
n is an integer of 0 to 3; and
W is —O—, —S—, —$SO_2$—, or —N($R^7$)— wherein $R^7$ is a ($C_1$-$C_6$)alkyl group.

Another preferable embodiment of the aminoacetonitrile compound represented by the formula (I), which is the active ingredient of the anticancer agent of the present invention, is a compound wherein m is 1.

Another preferable embodiment of the aminoacetonitrile compound represented by the formula (I), which is the active ingredient of the anticancer agent of the present invention, is a compound wherein
when m is 0, then
$Ar^1$ is
(e2) a phenyl group having, on the ring, the same or different 1 to 5 substituents selected from
(c) a nitro group,
(e') a halo($C_2$-$C_6$)alkyl group,
(f) a ($C_2$-$C_6$)alkenyl group,
(g) a ($C_2$-$C_6$)alkynyl group,
(i') a halo($C_2$-$C_6$)alkoxy group,
(j) a halo($C_2$-$C_6$)alkenyloxy group,
(k) a halo($C_2$-$C_6$)alkynyloxy group,
(l) a ($C_1$-$C_6$)alkylthio group,
(m) a ($C_1$-$C_6$)alkylsulfonyl group,
(n') a halo($C_2$-$C_6$)alkylthio group, (o) a phenyl(C$_2$-C$_6$)alkynyl group,
(p) a phenoxy group,
(q) a pyridyloxy group having, on the ring, the same or different 1 to 4 substituents selected from
  (i) a halogen atom, and
  (ii) a halo(C$_1$-C$_6$)alkyl group,
(r) a hydroxyl group,
(s) a phenyl group, and
(t) a halo(C$_1$-C$_6$)alkylsulfonylamino group,
(e3) a naphthyl group,
(e4) a naphthyl group having, on the ring, the same or different 1 to 7 substituents selected from
  (a) a halogen atom,
  (b) a cyano group,
  (c) a nitro group,
  (d) a (C$_1$-C$_6$)alkyl group, and
  (e) a halo(C$_1$-C$_6$)alkyl group,
(e5) a pyridyl group,
(e6) a pyridyl group having, on the ring, the same or different 1 to 4 substituents selected from
  (a) a halogen atom,
  (b) a (C$_1$-C$_6$)alkyl group,
  (c) a halo(C$_1$-C$_6$)alkyl group,
  (d) a (C$_1$-C$_6$)alkylthio group,
  (e) a (C$_1$-C$_6$)alkylsulfonyl group, and
  (f) a halo(C$_1$-C$_6$)alkylthio group,
(e7) a pyrazolyl group, or
(e8) a pyrazolyl group having, on the ring, the same or different 1 to 3 substituents selected from
  (a) a halogen atom,
  (b) a (C$_1$-C$_6$)alkyl group,
  (c) a halo(C$_1$-C$_6$)alkyl group,
  (d) a (C$_1$-C$_6$)alkylthio group,
  (e) a (C$_1$-C$_6$)alkylsulfonyl group, and
  (f) a (C$_1$-C$_6$)alkoxycarbonyl group.

Another preferable embodiment of the aminoacetonitrile compound represented by the formula (I), which is the active ingredient of the anticancer agent of the present invention, is a compound wherein
when m is 0, then
R is
(d2) a phenyl group having, on the ring, the same or different 1 to 5 substituents selected from
  (c) a nitro group,
  (e') a halo(C$_2$-C$_6$)alkyl group,
  (f) a (C$_2$-C$_6$)alkenyl group,
  (g) a (C$_2$-C$_6$)alkynyl group,
  (h) a (C$_1$-C$_6$)alkoxy group,
  (i) a halo(C$_1$-C$_6$)alkoxy group,
  (j) a halo(C$_2$-C$_6$)alkenyloxy group,
  (k) a halo(C$_2$-C$_6$)alkynyloxy group,
  (l) a (C$_1$-C$_6$)alkylthio group,
  (m) a (C$_1$-C$_6$)alkylsulfonyl group,
  (n) a halo(C$_1$-C$_5$)alkylthio group,
  (o) a phenyl(C$_2$-C$_6$)alkynyl group,
  (p) a phenoxy group, and
  (q) a pyridyloxy group having, on the ring, the same or different 1 to 4 substituents selected from
    (i) a halogen atom, and
    (ii) a halo(C$_1$-C$_6$)alkyl group,
(d3) a naphthyl group,
(d4) a naphthyl group having, on the ring, the same or different 1 to 7 substituents selected from
  (a) a halogen atom,
  (b) a cyano group,
  (c) a nitro group,
  (d) a (C$_1$-C$_6$)alkyl group, and
  (e) a halo(C$_1$-C$_6$)alkyl group, or
(d5) a (C$_1$-C$_{12}$)alkyl group.

Another preferable embodiment of the aminoacetonitrile compound represented by the formula (I), which is the active ingredient of the anticancer agent of the present invention, is a compound wherein
when m is 0, then
R$^1$ is
(a2) a (C$_1$-C$_6$)alkyl group,
(a3) a (C$_2$-C$_6$)alkenyl group,
(a4) a (C$_2$-C$_6$)alkynyl group, or
(a5) a (C$_3$-C$_6$)cycloalkyl group.

Another preferable embodiment of the aminoacetonitrile compound represented by the formula (I), which is the active ingredient of the anticancer agent of the present invention, is a compound wherein
when m is 0, then
R$^3$ is
(b2) a (C$_1$-C$_6$)alkyl group, or
(b3) a (C$_3$-C$_6$)cycloalkyl group, or
(b4) R$^2$ and R$^3$ are bonded to form a (C$_1$-C$_6$)alkylene group.

A further preferable embodiment of the aminoacetonitrile compound represented by the formula (I), which is the active ingredient of the anticancer agent of the present invention, is a compound wherein
R$^1$ is
(a1) a hydrogen atom, or
(a4) a (C$_2$-C$_6$)alkynyl group;
R$^2$, R$^3$ and R$^4$ are the same or different and each is
(b1) a hydrogen atom, or
(b2) a (C$_1$-C$_6$)alkyl group, or
(b4) R$^2$ and R$^3$ are optionally bonded to form a (C$_1$-C$_6$) alkylene group;
R$^5$ and R$^6$ are the same or different and each is
(c1) a hydrogen atom, or
(c6) R$^5$ and R$^6$ are optionally bonded to form a (C$_1$-C$_6$) alkylene group;
R is
(d1) a phenyl group,
(d2) a phenyl group having, on the ring, the same or different 1 to 5 substituents selected from
  (a) a halogen atom,
  (b) a cyano group,
  (c) a nitro group,
  (d) a (C$_1$-C$_6$)alkyl group,
  (e) a halo(C$_1$-C$_6$)alkyl group,
  (g) a (C$_2$-C$_6$)alkynyl group,
  (i) a halo(C$_1$-C$_6$)alkoxy group,
  (j) a halo(C$_2$-C$_6$)alkenyloxy group,
  (l) a (C$_1$-C$_6$)alkylthio group,
  (m) a (C$_1$-C$_6$)alkylsulfonyl group,
  (n) a halo(C$_1$-C$_6$)alkylthio group,
  (o) a phenyl(C$_2$-C$_6$)alkynyl group,
  (p) a phenoxy group, and
  (q) a pyridyloxy group having, on the ring, the same or different 1 to 4 substituents selected from
    (i) a halogen atom, and
    (ii) a halo(C$_1$-C$_6$)alkyl group,
(d3) a naphthyl group, or
(d5) a (C$_1$-C$_{12}$)alkyl group;
Ar$^1$ is
(e1) a phenyl group,
(e2) a phenyl group having, on the ring, the same or different 1 to 5 substituents selected from
  (a) a halogen atom,
  (b) a cyano group,
  (c) a nitro group, (d) a $(C_1-C_6)$alkyl group,
(e) a halo$(C_1-C_6)$alkyl group,
(h) a $(C_1-C_6)$alkoxy group,
(i) a halo$(C_1-C_6)$alkoxy group,
(n) a halo$(C_1-C_6)$alkylthio group,
(q) a pyridyloxy group having, on the ring, the same or different 1 to 4 substituents selected from
  (i) a halogen atom, and
  (ii) a halo$(C_1-C_6)$alkyl group,
(r) a hydroxyl group,
(s) a phenyl group, and
(t) a halo$(C_1-C_6)$alkylsulfonylamino group,
(e3) a naphthyl group,
(e5) a pyridyl group,
(e6) a pyridyl group having, on the ring, the same or different 1 to 4 substituents selected from
  (a) a halogen atom,
  (b) a $(C_1-C_6)$alkyl group,
  (c) a halo$(C_1-C_6)$alkyl group,
  (d) a $(C_1-C_6)$alkylthio group,
  (e) a $(C_1-C_6)$alkylsulfonyl group, and
  (f) a halo$(C_1-C_6)$alkylthio group, or
(e8) a pyrazolyl group having, on the ring, the same or different 1 to 3 substituents selected from
  (a) a halogen atom,
  (b) a $(C_1-C_6)$alkyl group,
  (c) a halo$(C_1-C_6)$alkyl group,
  (d) a $(C_1-C_6)$alkylthio group,
  (e) a $(C_1-C_6)$alkylsulfonyl group, and
  (f) a $(C_1-C_6)$alkoxycarbonyl group; and
W is —O—.

The production method of the aminoacetonitrile compound represented by the formula (I) of the present invention is explained below.

Production Method

The aminoacetonitrile compound represented by the formula (I) of the present invention can be produced according to the method described in patent document 1 (JP-A-2000-026392), and an example thereof is shown below.

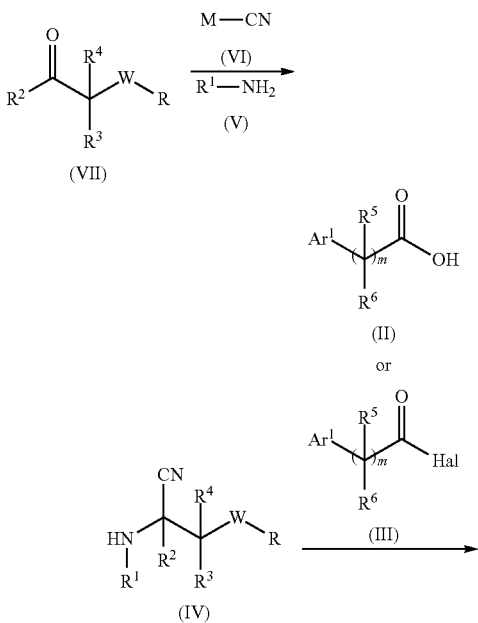

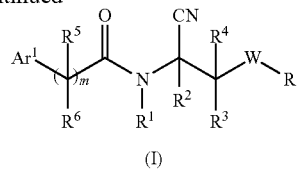

wherein R, $R^1$, $R^2$, $R^3$, $R^4$, $R^5$, $R^6$, $Ar^1$, W and m are as defined above, M is an alkali metal atom, and Hal is a halogen atom.

1. Production of Formula (IV)→Formula (I)

The aminoacetonitrile compound represented by the formula (I) can be produced by reacting the aminoacetonitriles represented by the formula (IV) with the acid halides represented by the formula (III) in the presence of a base (for example, triethylamine, pyridine, etc.). Alternatively, the compound can also be produced by condensing the aminoacetonitriles represented by the formula (IV) with the carboxylic acids represented by the formula (II) using a condensing agent (e.g., dicyclohexylcarbodiimide, 2-chloro-1-methylpyridinium iodide etc.).

2. Production Method of Formula (VII)→Formula (IV)

The aminoacetonitriles represented by the formula (IV) can be produced according to a method known as the Strecker reaction (e.g., Formation of C—C Bonds Vol. 1 Georg Thieme Publishers 1973, Organic Synthesis Coll. Vol. 3.88, etc.). For example, they can be produced by reacting the carbonyl compounds represented by the formula (VII) with the metal cyanide represented by the formula (VI) (e.g., sodium cyanide, potassium cyanide, etc.), and the amines represented by the formula (V). As a cyanogen source, organic cyanides such as trimethylsilyl nitrile, acetone cyanohydrin and the like can also be used.

The intermediates and object compounds in each of the above-mentioned production methods can be isolated and purified by subjecting them to purification methods conventionally used in the organic synthetic chemistry, for example, neutralization, filtration, extraction, washing, drying, concentration, recrystallization, various chromatographies and the like. In addition, the intermediates can also be subjected to the next reaction without particular purification.

The carboxylic acids represented by the formula (II), the acid halides represented by the formula (III), the amines represented by the formula (V) and the carbonyl compounds represented by the formula (VII), which are used as starting materials in the above-mentioned production methods, can be produced by a method known per se, and commercially available products can also be used.

The aminoacetonitrile compound represented by the formula (I) of the present invention has at least one asymmetric carbon, and can be present as a stereoisomer (optical isomer, diastereomer). When a double bond and the like are present, it can be present as a geometric isomer. The aminoacetonitrile compound represented by the formula (I) of the present invention can use all these possible isomers and a mixture thereof (racemate, diastereomer mixture etc.) as an active ingredient of an anticancer agent.

When a salt of the aminoacetonitrile compound represented by the formula (I) of the present invention is to be obtained and compound (I) is obtained in the form of a salt, it can be directly purified. When it is obtained in a free form, a salt can be formed by dissolving or suspending the free form in a suitable organic solvent, and adding an acid or a base according to a general method.

While the aminoacetonitrile compound represented by the formula (I) of the present invention and a pharmacologically acceptable salt thereof are sometimes present in the form of a hydrate or a solvate with various solvents, these hydrates and solvates can also be used as the active ingredient of the anticancer agent of the present invention.

Representative examples of the aminoacetonitrile compound represented by the formula (I) of the present invention are exemplified in Table 1, Table 2, Table 4, Table 5 and Table 6 below; however, the present invention is not limited thereto.

In the Tables, "Me" is a methyl group, "Et" is an ethyl group, "Pr" is a propyl group, "Bu" is a butyl group, "Octyl" is an octyl group, "Ph" is a phenyl group, "n-" is normal, "i-" is iso, "c-" is cyclo, "s-" is secondary, "t-" is tertiary, and "Py-" is a pyridyl group, "Pyra-" is a pyrazolyl group, "Naph-" is a naphthyl group, "Pym" is a pyrimidyl group, "Pyz" is a pyrazinyl group, "Thz" is a thiazolyl group, "Iox" is an isoxazolyl group, "Ox" is an oxazolyl group, "Thienyl" is a thienyl group, "Furyl" is a furyl group, "morpholino" is a morpholino group, "piperidino" is a piperidino group. The "substitutable position" in each structural formula shows a substitutable position, and the property shows melting point (° C.) or refractive index $n_D$ (measurement temperature; ° C.), or $^1$H-NMR data are shown in Table 3.

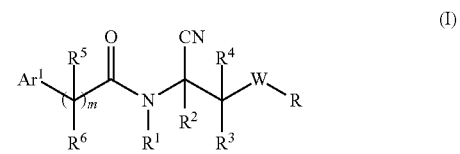

(I)

TABLE 1

| Comp. No. | Ar$^1$ | R | R$^1$ | R$^2$ | R$^3$ | W | property |
|---|---|---|---|---|---|---|---|
| 1-1 | 4-Cl—Ph | Ph | H | Me | H | O | 135-140 |
| 1-2 | 4-Cl—Ph | Ph | H | Me | H | S | 125-126 |
| 1-3 | 4-Cl—Ph | Ph | H | Me | H | SO$_2$ | 160-162 |
| 1-4 | 4-CF$_3$—Ph | 4-Cl—Ph | H | Et | H | O | 118-119 |
| 1-5 | 4-CF$_3$—Ph | 4-Cl—Ph | H | H | H | O | 134-139 |
| 1-6 | 4-CF$_3$—Ph | 4-Cl—Ph | H | t-Bu | H | O | 126-135 |
| 1-7 | 4-CF$_3$—Ph | 4-Cl—Ph | H | (CH$_2$)$_4$ | | O | NMR |
| 1-8 | 2-CF$_3$—Ph | 4-CF$_3$—Ph | H | Me | H | O | 128-130 |
| 1-9 | 3-CF$_3$—Ph | 4-CF$_3$—Ph | H | Me | H | O | 115 |
| 1-10 | 4-C$_2$F$_5$—Ph | 4-CF$_3$—Ph | H | Me | H | O | 127-129 |
| 1-11 | 4-CF$_3$—Ph | 4-CF$_3$O—Ph | H | Me | H | O | 127-128 |
| 1-12 | 2-Cl—Ph | 4-CF$_3$—Ph | H | Me | H | O | 122-123 |
| 1-13 | 3-Cl—Ph | 4-CF$_3$—Ph | H | Me | H | O | 149-153 |
| 1-14 | 4-Cl—Ph | 4-CF$_3$—Ph | H | Me | H | O | 143-145 |
| 1-15 | 2-Cl-4-NO$_2$—Ph | 4-CF$_3$—Ph | H | Me | H | O | 205-208 |
| 1-16 | 4-MeO—Ph | 4-CF$_3$—Ph | H | Me | H | O | 162-166 |
| 1-17 | 3,5-(t-Bu)$_2$-4-OH—Ph | 4-CF$_3$—Ph | H | Me | H | O | 192-193 |
| 1-18 | 3,4-Cl$_2$—Ph | 4-CF$_3$—Ph | H | Me | H | O | 146-148 |
| 1-19 | 2-Cl-4-F—Ph | 4-CF$_3$—Ph | H | Me | H | O | 130-132 |
| 1-20 | 4-CF$_3$—Ph | 4-Cl—Ph | Me | Me | H | O | 98-100 |
| 1-21 | 1-Me-3-CF$_3$-4-Pyra | 4-CF$_3$—Ph | H | Me | H | O | 118-120 |
| 1-22 | 2,5-Cl$_2$—Ph | 4-CF$_3$—Ph | H | Me | H | O | 118-120 |
| 1-23 | 4-CF$_3$S—Ph | 4-CF$_3$—Ph | H | Me | H | O | 140-141 |
| 1-24 | 2-Me—Ph | 4-CF$_3$—Ph | H | Me | H | O | 137-140 |
| 1-25 | 4-CF$_3$—Ph | 4-Ph—C≡C—Ph | H | Me | H | O | 195-197 |
| 1-26 | 4-CF$_3$—Ph | 4-t-Bu—C≡C—Ph | H | Me | H | O | 216-217 |
| 1-27 | 3,5-Me$_2$—Ph | 4-Cl—Ph | H | Me | H | O | 120-130 |
| 1-28 | 4-CF$_3$O—Ph | 4-CF$_3$—Ph | H | Me | H | O | 132-136 |
| 1-29 | 3-CF$_3$O—Ph | 4-CF$_3$—Ph | H | Me | H | O | 92 |
| 1-30 | 4-F—Ph | 4-CF$_3$—Ph | H | Me | H | O | 135-137 |
| 1-31 | 2,4-Cl$_2$—Ph | 4-CF$_3$—Ph | H | Me | H | O | 120-122 |
| 1-32 | 4-I—Ph | 4-CF$_3$—Ph | H | Me | H | O | 155-160 |
| 1-33 | 4-NO$_2$—Ph | 4-CF$_3$—Ph | H | Me | H | O | 96-97 |
| 1-34 | 2-Naph | 4-CF$_3$—Ph | H | Me | H | O | 219-222 |
| 1-35 | 3-Me—Ph | 4-CF$_3$—Ph | H | Me | H | O | 166-168 |
| 1-36 | 4-Me—Ph | 4-CF$_3$—Ph | H | Me | H | O | 188-190 |
| 1-37 | 2-MeO—Ph | 4-CF$_3$—Ph | H | Me | H | O | 85-87 |
| 1-38 | 2,4-F$_2$—Ph | 4-CF$_3$—Ph | H | Me | H | O | 127-128 |
| 1-39 | 1-Me-3-CF$_3$-5-Pyra | 4-Cl—Ph | H | Me | H | O | amorphous |
| 1-40 | 1-Me-3-CF$_3$-5-Pyra | 4-CF$_3$—Ph | H | Me | H | O | 137-139 |
| 1-41 | 5,6-Cl$_2$-3-Py | 4-Cl—Ph | H | Me | H | O | 171-173 |
| 1-42 | 5,6-Cl$_2$-3-Py | 4-CF$_3$—Ph | H | Me | H | O | 158-159 |
| 1-43 | 2-Cl-3-Py | 4-CF$_3$—Ph | H | Me | H | O | 150-154 |
| 1-44 | 6-Cl-3-Py | 4-CF$_3$—Ph | H | Me | H | O | 137-140 |
| 1-45 | 3-Py | 4-CF$_3$—Ph | H | Me | H | O | 133-134 |
| 1-46 | 2-Cl-6-Me-3-Py | 4-CF$_3$—Ph | H | Me | H | O | NMR |
| 1-47 | 2,6-Cl$_2$-4-Py | 4-CF$_3$—Ph | H | Me | H | O | 119-123 |
| 1-48 | 1-Me-3-CF$_3$-4-Cl-5-Pyra | 4-CF$_3$—Ph | H | Me | H | O | 100-103 |

TABLE 1-continued

| Comp. No. | Ar¹ | R | R¹ | R² | R³ | W | property |
|---|---|---|---|---|---|---|---|
| 1-49 | 4-n-Bu—Ph | 4-CF₃—Ph | H | Me | H | O | 184-186 |
| 1-50 | 2-CHF₂S-3-Py | 4-CF₃—Ph | H | Me | H | O | NMR |
| 1-51 | 5-CF₃-3-Pyra | 4-CF₃—Ph | H | Me | H | O | 198-199 |
| 1-52 | 1-Me-3-CF₃-4-COOEt-5-Pyra | 4-CF₃—Ph | H | Me | H | O | amorphous |
| 1-53 | 1-CHF₂-3-CF₃-5-Pyra | 4-CF₃—Ph | H | Me | H | O | amorphous |
| 1-54 | 4-CF₃-2-F—Ph | 4-CF₃—Ph | H | Me | H | O | 118-119 |
| 1-55 | 4-(5-CF₃-3-Cl-2-PyO)—Ph | 4-CF₃—Ph | H | Me | H | O | 133-138 |
| 1-56 | 2,4-Cl₂-Ph | 4-CF₃—Ph | H | t-Bu | H | O | 148-150 |
| 1-57 | 4-CN—Ph | 4-CF₃—Ph | H | Me | Me | O | 206-208 |
| 1-58 | 2-Py | 4-CF₃—Ph | H | Me | H | O | 90-91 |
| 1-59 | 2-MeS-3-Py | 4-CF₃—Ph | H | Me | H | O | 137-140 |
| 1-60 | 2-MeSO₂-3-Py | 4-CF₃—Ph | H | Me | H | O | 132 |
| 1-61 | 3,5-Cl₂-2-Py | 4-CF₃—Ph | H | Me | H | O | NMR |
| 1-62 | 5-CF₃-3-Cl-2-Py | 4-CF₃—Ph | H | Me | H | O | NMR |
| 1-63 | 4-CN—Ph | 4-CF₃—Ph | Me | Me | H | O | 137-141 |
| 1-64 | 1-Naph | 4-CF₃—Ph | H | Me | H | O | 138-140 |
| 1-65 | 4-CF₃SO₂NH—Ph | 4-CF₃—Ph | H | Me | H | O | 200-202 |
| 1-66 | 4-Me-1,2,3-thiadiazol-5-yl | 2-CF₃-5-CN—Ph | H | Me | H | O | 1.5185(21.0) |
| 1-67 | 4-Me-5-Thz | 2-CF₃-5-CN—Ph | H | Me | H | O | 1.5187(21.1) |
| 1-68 | 4-CF₃-5-Thz | 2-CF₃-5-CN—Ph | H | Me | H | O | 203-205 |
| 1-69 | 5-CF₃-1,3,4-thiadiazol-2-yl | 2-CF₃-5-CN—Ph | H | Me | H | O | 70-75 |
| 1-70 | 4-CF₃—Ph | 2-Cl—Ph | H | Me | H | O | 128-130 |
| 1-71 | 4-CF₃—Ph | 3-Cl—Ph | H | Me | H | O | 105-108 |
| 1-72 | 4-CF₃—Ph | 4-Cl—Ph | H | Me | H | O | 125-129 |
| 1-73 | 4-CF₃—Ph | 4-Ph—Ph | H | Me | H | O | 177-179 |
| 1-74 | 4-CF₃—Ph | 2-PhO—Ph | H | Me | H | O | 132-133 |
| 1-75 | 4-CF₃—Ph | 4-Cl—Ph | H | Me | H | O | NMR |
| 1-76 | 4-CF₃—Ph | 4-Cl—Ph | H | Me | H | O | NMR |
| 1-77 | 3-CF₃-2-Pyz | 2-CF₃-5-CN—Ph | H | Me | H | S | 1.5263(22.2) |
| 1-78 | 3-CF₃-2-Pyz | 2-CF₃—Ph | H | Me | H | O | 1.5004(22.1) |
| 1-79 | 3-CF₃-2-Pyz | 2-CF₃-5-CN—Ph | H | Me | H | O | NMR |
| 1-80 | 3-CF₃-2-Pyz | 2-CN—Ph | H | Me | H | O | 140-144 |
| 1-81 | 3-CF₃-2-Pyz | 2-Cl-5-NO₂—Ph | H | Me | H | O | NMR |
| 1-82 | 3-CF₃-2-Pyz | 3-CF₃—Ph | H | Me | H | O | 1.4280(22.4) |
| 1-83 | 3-CF₃-2-Pyz | 3-CN—Ph | H | Me | H | O | 65-66 |
| 1-84 | 3-CF₃-2-Pyz | 4-MeS—Ph | Me | Me | H | O | 1.5437(22.3) |
| 1-85 | 3-CF₃-2-Pyz | 4-MeSO—Ph | H | Me | H | O | 84-89 |
| 1-86 | 3-CF₃-2-Pyz | 4-MeSO₂—Ph | H | Me | H | O | 1.4203(22.3) |
| 1-87 | 3-CF₃-2-Pyz | 2-SCF₃—Ph | H | Me | H | O | 1.5114(19.3) |
| 1-88 | 3-CF₃-2-Pyz | 2-SOCF₃—Ph | H | Me | H | O | 1.4064(19.6) |
| 1-89 | 3-CF₃-2-Pyz | 2-SO₂CF₃—Ph | H | Me | H | O | 50-53 |
| 1-90 | 3-CF₃-2-Pyz | 3-SCF₃—Ph | H | Me | H | O | 1.5100(20.9) |
| 1-91 | 3-CF₃-2-Pyz | 3-SOCF₃—Ph | H | Me | H | O | 1.5056(21.0) |
| 1-92 | 3-CF₃-2-Pyz | 3-SO₂CF₃—Ph | H | Me | H | O | 1.4320(20.5) |
| 1-93 | 4-CF₃S—Ph | 4-Ph—C≡C—Ph | H | Me | H | O | 170-173 |
| 1-94 | 4-Cl—Ph | 4-t-Bu—C≡C—Ph | H | Me | H | O | 175-176 |

TABLE 1-continued

| Comp. No. | Ar¹ | R | R¹ | R² | R³ | W | property |
|---|---|---|---|---|---|---|---|
| 1-95 | 4-Cl—Ph | 4-t-Bu—C≡C—Ph | H | Me | H | O | 201-203 |
| 1-96 | 4-CF₃S—Ph | 4-t-Bu—C≡C—Ph | H | Me | H | O | 190-192 | m = 0,
R⁴ = H.

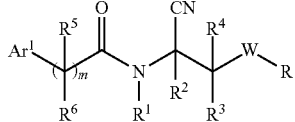

(I)

TABLE 2

| Comp. No. | Ar¹ | R | R¹ | R² | R³ | C(R⁵)R⁶ | W | property |
|---|---|---|---|---|---|---|---|---|
| 2-1 | Ph | 4-Cl—Ph | H | Me | H | —CH₂— | O | 152 |
| 2-2 | 2-F—Ph | 4-Cl—Ph | H | Me | H | —CH₂— | O | 132-133 |
| 2-3 | 3-Cl—Ph | 4-Cl—Ph | H | Me | H | —CH₂— | O | 103-104 |
| 2-4 | 2,6-F₂—Ph | 4-Cl—Ph | H | Me | H | —CH₂— | O | 130-131 |
| 2-5 | 4-Cl—Ph | 4-t-Bu—Ph | H | Me | H | —CH₂— | O | 162 |
| 2-6 | 4-MeO—Ph | 4-Cl—Ph | H | Me | H | —CH₂— | O | 115 |
| 2-7 | 4-Ph—Ph | 4-Cl—Ph | H | Me | H | —CH₂— | O | 131-132 |
| 2-8 | 2,4,6-Me₃—Ph | 4-Cl—Ph | H | Me | H | —CH₂— | O | 136 |
| 2-9 | Ph | Ph | H | Me | H | cyclopropylidene | O | 101 |
| 2-10 | Ph | 4-Cl—Ph | H | Me | H | cyclopropylidene | O | 121 |
| 2-11 | 4-Cl—Ph | 4-Cl—Ph | H | Me | H | —CH₂— | S | 95 |
| 2-12 | 4-Cl—Ph | 4-Cl—Ph | H | Me | H | —CH₂— | SO₂ | 153 |
| 2-13 | 4-CF₃—Ph | 4-Cl—Ph | H | Me | H | —CH₂— | O | 119 |
| 2-14 | 4-Cl—Ph | 4-CF₃O—Ph | H | Me | H | —CH₂— | O | 130 |
| 2-15 | 4-Cl—Ph | 3-Cl—Ph | H | Me | H | —CH₂— | O | 126-127 |
| 2-16 | 4-Cl—Ph | 4-CF₃—Ph | H | Me | H | —CH₂— | O | 120-121 |
| 2-17 | 4-Br—Ph | 4-Cl—Ph | H | Me | H | —CH₂— | O | 146 |
| 2-18 | 2,6-Cl₂—Ph | 4-Cl—Ph | H | Me | H | —CH₂— | O | 141 |
| 2-19 | 4-Cl—Ph | 4-Cl—Ph | H | Me | H | —CH₂— | O | 152 |
| 2-20 | 4-Cl—Ph | Ph | H | Me | H | —CH₂— | S | 142 |
| 2-21 | 4-Cl—Ph | Ph | H | Me | H | —CH₂— | SO₂ | 169 |
| 2-22 | 2,3,4,5,6-F₅—Ph | 4-F—Ph | H | Me | H | —CH₂— | O | 87 |
| 2-23 | 2-Naph | 4-Cl—Ph | H | Me | H | —CH₂— | O | 138 |
| 2-24 | 4-Cl—Ph | 4-Cl—Ph | H | (CH₂)₄ | | —CH₂— | 0 | 78-83 |
| 2-25 | 4-MeO—Ph | 4-Cl—Ph | H | i-Pr | H | —CH₂— | O | 114-117 |
| 2-26 | 2-Cl—Ph | 4-Cl—Ph | H | i-Pr | H | —CH₂— | O | 124-126 |
| 2-27 | 3-Cl—Ph | 4-Cl—Ph | H | i-Pr | H | —CH₂— | O | 121-122 |
| 2-28 | 2-Cl—Ph | 4-Cl—Ph | H | c-Pr | H | —CH₂— | O | 124-126 |
| 2-29 | 3-Cl—Ph | 4-Cl—Ph | H | c-Pr | H | —CH₂— | O | 121-124 |
| 2-30 | 4-MeO—Ph | 4-Cl—Ph | H | c-Pr | H | —CH₂— | O | 118-122 |
| 2-31 | 4-Cl—Ph | 3-CF₃—Ph | H | Me | H | —CH₂— | O | 132-133 |
| 2-32 | 4-Cl—Ph | 3-CF₃-4-NO₂—Ph | H | Me | H | —CH₂— | O | 141-142 |
| 2-33 | 4-Cl—Ph | 3,4-Cl₂—Ph | H | Me | H | —CH₂— | O | 125-126 |
| 2-34 | 4-Cl—Ph | 3,5-Me₂—Ph | H | Me | H | —CH₂— | O | 175-176 |
| 2-35 | 2-Cl—Ph | 4-Cl—Ph | H | Me | H | —CH₂— | O | 138-139 |
| 2-36 | 4-Cl—Ph | 4-Cl—Ph | H | H | H | —CH₂— | O | 122-127 |
| 2-37 | 2-Cl—Ph | 4-Cl—Ph | H | H | H | —CH₂— | O | 127-133 |
| 2-38 | 4-Me—Ph | 3,5-Me₂—Ph | H | Me | H | —CH₂— | O | 110-112 |
| 2-39 | 4-MeO—Ph | 3,5-Me₂—Ph | H | Me | H | —CH₂— | O | 126-127 |
| 2-40 | 3-Me—Ph | 3,5-Me₂—Ph | H | Me | H | —CH₂— | O | 117-118 |
| 2-41 | 2-Me—Ph | 3,5-Me₂—Ph | H | Me | H | —CH₂— | O | 123-124 |
| 2-42 | 2-Cl—Ph | 4-Cl—Ph | Et | Me | H | —CH₂— | O | 110-112 |
| 2-43 | 4-Cl—Ph | 4-F—Ph | H | Me | H | —CH₂— | O | 127-130 |
| 2-44 | 4-CF₃—Ph | 4-F—Ph | H | Me | H | —CH₂— | O | 128-130 |
| 2-45 | 4-CF₃—Ph | 4-CF₃O—Ph | H | Me | H | —CH₂— | O | 85-87 |
| 2-46 | 4-Cl—Ph | 2-Cl—Ph | H | Me | H | —CH₂— | O | 126-127 |

TABLE 2-continued

| Comp. No. | Ar¹ | R | R¹ | R² | R³ | C(R⁵)R⁶ | W | property |
|---|---|---|---|---|---|---|---|---|
| 2-47 | 4-CF₃—Ph | 2-Cl—Ph | H | Me | H | —CH₂— | O | 130 |
| 2-48 | 3,4-F₂—Ph | 4-CF₃—Ph | H | Me | H | —CH₂— | O | 85 |
| 2-49 | 2,6-F₂—Ph | 4-CF₃—Ph | H | Me | H | —CH₂— | O | 154-155 |
| 2-50 | 2,4-Cl₂—Ph | 4-CF₃—Ph | H | Me | H | —CH₂— | O | 123-124 |
| 2-51 | 4-CF₃—Ph | 4-PhO—Ph | H | Me | H | —CH₂— | O | 135-136 |
| 2-52 | 4-F—Ph | 4-Cl—Ph | H | Me | H | —CH₂— | O | 159-160 |
| 2-53 | 4-F—Ph | 4-CF₃O—Ph | H | Me | H | —CH₂— | O | 107-109 |
| 2-54 | 3,5-(CF₃)₂—Ph | 4-CF₃—Ph | H | Me | H | —CH₂— | O | 104-106 |
| 2-55 | 4-CF₃—Ph | 2,4-F₂—Ph | H | Me | H | —CH₂— | O | 88-90 |
| 2-56 | 4-CF₃—Ph | 2,6-F₂—Ph | H | Me | H | —CH₂— | O | 112-113 |
| 2-57 | 4-Cl—Ph | 4-Cl—Ph | H | Me | Me | —CH₂— | O | 124-141 |
| 2-58 | 4-MeO—Ph | 4-Cl—Ph | H | Me | Me | —CH₂— | O | 129-131 |
| 2-59 | 4-Cl—Ph | 2-Naph | H | Me | H | —CH₂— | O | 146-147 |
| 2-60 | 4-Cl—Ph | 4-(5-CF₃-2-PyO)Ph | H | Me | H | —CH₂— | O | 160-161 |
| 2-61 | 4-Cl—Ph | 4-Cl—Ph | H | Me | H | cyclopropylidene | O | 145-146 |
| 2-62 | 4-Cl—Ph | 4-CF₃—Ph | H | Me | H | cyclopropylidene | O | 114-115 |
| 2-63 | 4-F—Ph | 4-i-Pr—Ph | H | Me | H | —CH₂— | O | 137-139 |
| 2-64 | 3-Cl—Ph | 4-Cl—Ph | H | Me | H | cyclopropylidene | O | 113-114 |
| 2-65 | 2-F—Ph | 4-Cl—Ph | H | Me | H | cyclopropylidene | O | 116-117 |
| 2-66 | 4-Cl—Ph | 4-Cl—Ph | H | Me | H | cyclobutylidene | O | 123 |
| 2-67 | 1,3-Me₂-5-MeS-4-Pyra | 4-Cl—Ph | H | Me | H | —CH₂— | O | 147-148 |
| 2-68 | 4-Cl—Ph | 4-Cl—Ph | H | Et | H | —CH₂— | O | 126-127 |
| 2-69 | 4-MeO—Ph | 4-Cl—Ph | H | Et | H | —CH₂— | O | 104-106 |
| 2-70 | 1,3-Me₂-5-MeSO₂-4-Pyra | 4-Cl—Ph | H | Me | H | —CH₂— | O | 142-143 |
| 2-71 | 4-F—Ph | 4-Cl—Ph | H | Me | H | —CH₂— | NMe | 156-157 |
| 2-72 | 2-Cl—Ph | 4-Cl—Ph | H | t-Bu | H | —CH₂— | O | NMR |
| 2-73 | 3-Cl—Ph | 4-Cl—Ph | H | t-Bu | H | —CH₂— | O | NMR |
| 2-74 | 4-MeO—Ph | 4-Cl—Ph | H | t-Bu | H | —CH₂— | O | NMR |
| 2-75 | 2-Cl—Ph | 4-Cl—Ph | H | n-Pr | H | —CH₂— | O | 107-110 |
| 2-76 | 3-Cl—Ph | 4-Cl—Ph | H | n-Pr | H | —CH₂— | O | 96-99 |
| 2-77 | 4-MeO—Ph | 4-Cl—Ph | H | n-Pr | H | —CH₂— | O | NMR |
| 2-78 | 4-F—Ph | 4-CN—Ph | H | Me | H | —CH₂— | O | 138-140 |
| 2-79 | 4-F—Ph | 4-NO₂—Ph | H | Me | H | —CH₂— | O | 108-110 |
| 2-80 | 4-F—Ph | 4-F—Ph | H | Me | H | —CH₂— | O | 128-129 |
| 2-81 | 4-Cl—Ph | 3-Cl-4-F—Ph | H | Me | H | —CH₂— | O | 93-94 |
| 2-82 | 4-F—Ph | 3-Cl-4-F—Ph | H | Me | H | —CH₂— | O | 128-129 |
| 2-83 | 2-Cl—Ph | 4-Cl—Ph | H | Et | H | —CH₂— | O | 130-131 |
| 2-84 | 4-Cl—Ph | 4-Cl—Ph | H | n-Pr | H | —CH₂— | O | 103-105 |
| 2-85 | 4-F—Ph | 2,3,4,5,6-F₅—Ph | H | Me | H | —CH₂— | O | 108-110 |
| 2-86 | 3,4-F₂—Ph | 4-F—Ph | H | Me | H | —CH₂— | O | 94 |
| 2-87 | 4-Cl—Ph | 4-Cl—Ph | H | (CH₂)₄ | | —CH₂— | O | NMR |
| 2-88 | 4-MeO—Ph | 4-Cl—Ph | H | (CH₂)₄ | | —CH₂— | O | NMR |
| 2-89 | 3-Cl—Ph | 4-Cl—Ph | H | (CH₂)₄ | | —CH₂— | O | NMR |
| 2-90 | 4-Cl—Ph | 4-Cl—Ph | H | i-Pr | H | —CH₂— | O | 140 |
| 2-91 | 4-Cl—Ph | 4-Cl—Ph | H | c-Pr | H | —CH₂— | O | 142 |
| 2-92 | 4-Cl—Ph | 4-MeS—Ph | H | Me | H | —CH₂— | O | 85-86 |
| 2-93 | 4-Cl—Ph | 4-MeSO₂—Ph | H | Me | H | —CH₂— | O | NMR |
| 2-94 | 4-CF₃O—Ph | 4-CF₃—Ph | H | Me | H | —CH₂— | O | 121-125 |
| 2-95 | 2-F-4-Cl—Ph | 4-CF₃—Ph | H | Me | H | —CH₂— | O | 104-106 |
| 2-96 | 2-Cl-4-F—Ph | 4-CF₃—Ph | H | Me | H | —CH₂— | O | 140-142 |
| 2-97 | 4-Cl—Ph | 4-I—Ph | H | Me | H | —CH₂— | O | 160-161 |
| 2-98 | 4-Cl—Ph | 4-C₂F₅—Ph | H | Me | H | —CH₂— | O | 96-100 |
| 2-99 | 2-Cl—Ph | 4-Cl—Ph | n-Bu | Me | H | —CH₂— | O | 118-120 |
| 2-100 | 2-Cl—Ph | 4-Cl—Ph | HC≡CCH₂ | Me | H | —CH₂— | O | 72-74 |
| 2-101 | 4-Cl—Ph | 4-Cl—Ph | HC≡CCH₂ | Me | H | —CH₂— | O | 114-117 |

TABLE 2-continued

| Comp. No. | Ar¹ | R | R¹ | R² | R³ | C(R⁵)R⁶ | W | property |
|---|---|---|---|---|---|---|---|---|
| 2-102 | 4-Cl—Ph | 4-Cl₂C=CHCH₂O—Ph | H | Me | H | —CH₂— | O | 88-89 |
| 2-103 | 4-CF₃—Ph | 4-Cl₂C=CHCH₂O—Ph | H | Me | H | —CH₂— | O | 87-88 |
| 2-104 | 4-Cl—Ph | 4-C₃F₇S—Ph | H | Me | H | —CH₂— | O | 91-92 |
| 2-105 | 4-Cl—Ph | 4-n-C₆F₁₃S—Ph | H | Me | H | —CH₂— | O | 102-104 |
| 2-106 | 4-CF₃—Ph | 4-n-C₆F₁₃S—Ph | H | Me | H | —CH₂— | O | 90-91 |
| 2-107 | 4-Cl—Ph | 4-Cl₂C=CHCH₂O—Ph | H | Me | H | —CH₂— | O | 87-89 |
| 2-108 | 4-Cl—Ph | 4-Cl—Ph | H | Me | H | —CH₂— | O | 96-97 |
| 2-109 | 4-n-C₃F₇—Ph | 4-CF₃—Ph | H | Me | H | —CH₂— | O | 86-88 |
| 2-110 | 4-Cl—Ph | 4-n-C₃F₇—Ph | H | Me | H | —CH₂— | O | 126-127 |
| 2-111 | 4-I—Ph | 4-CF₃—Ph | H | Me | H | —CH₂— | O | 98-99 |
| 2-112 | 4-CF₃—Ph | 4-n-C₃F₇—Ph | H | Me | H | —CH₂— | O | 83-85 |
| 2-113 | 4-n-C₃F₇—Ph | 4-Cl—Ph | H | Me | H | —CH₂— | O | 88-89 |
| 2-114 | 4-n-C₃F₇S—Ph | 4-Cl—Ph | H | Me | H | —CH₂— | O | 86-88 |
| 2-115 | 4-C₂F₅—Ph | 4-CF₃—Ph | H | Me | H | —CH₂— | O | 133-137 |
| 2-116 | 4-Cl—Ph | 4-Ph—C≡C—Ph | H | Me | H | —CH₂— | O | 155-157 |
| 2-117 | 4-I—Ph | 4-I—Ph | H | Me | H | —CH₂— | O | 142-143 |
| 2-118 | 4-F—Ph | 4-I—Ph | H | Me | H | —CH₂— | O | 144 |
| 2-119 | 4-Cl—Ph | 4-t-Bu—C≡C—Ph | H | Me | H | —CH₂— | O | 159-162 |
| 2-120 | 4-CF₃—Ph | 4-t-Bu—C≡C—Ph | H | Me | H | —CH₂— | O | 159-160 |
| 2-121 | 4-CF₃—Ph | 2-Me-4-I—Ph | H | Me | H | —CH₂— | O | 108-109 |
| 2-122 | 2-I—Ph | 4-CF₃—Ph | H | Me | H | —CH₂— | O | 146-147 |
| 2-123 | 2,4-F₂—Ph | 4-CF₃—Ph | H | Me | H | —CH₂— | O | 145-120 |
| 2-124 | 2-Py | 2-CF₃-5-CN—Ph | H | Me | H | —CH₂— | O | 1.4426(20.5) |
| 2-125 | 3-Py | 2-CF₃-5-CN—Ph | H | Me | H | —CH₂— | O | 177-178 |
| 2-126 | 4-Py | 2-CF₃-5-CN—Ph | H | Me | H | —CH₂— | O | 1.4246(20.8) |
| 2-127 | 5-CF₃-2-Py | 2-CF₃-5-CN—Ph | H | Me | H | —CH₂— | O | 124.6-127.2 |
| 2-128 | 5-CF₃-3-Cl-2-Py | 2-CF₃-5-CN—Ph | H | Me | H | —CH₂— | O | 189.2-191.9 |
| 2-129 | 4-CF₃—Ph | 2-CF₃-5-CN—Ph | H | Me | H | —CH₂— | O | 79.9-82.0 |
| 2-130 | 4-CF₃—Ph | 2-CF₃-5-CN—Ph | H | Me | H | —CH(OMe)— | O | 135.8-136.4 |
| 2-131 | 3-CF₃-2-Pyz | 2-CF₃-5-CN—Ph | H | Me | H | —CH₂— | O | 46-52 |
| 2-132 | 4-CF₃S—Ph | 2-CF₃-5-NO₂—Ph | H | Me | H | —CH₂— | O | 165-170 |
| 2-133 | 4-CF₃S—Ph | 2-CF₃—Ph | H | Me | H | —CH₂— | O | 109-110 |
| 2-134 | 4-CF₃S—Ph | 3-CN—Ph | H | Me | H | —CH₂— | O | 1.4586(22.1) |
| 2-135 | 4-CF₃S—Ph | 4-Ph—Ph | H | Me | H | —CH₂— | O | 134-135 |
| 2-136 | 4-CF₃S—Ph | 2-Ph—Ph | H | Me | H | —CH₂— | O | 41-44 |
| 2-137 | 4-CF₃S—Ph | 2-CF₃-5-Ph—Ph | H | Me | H | —CH₂— | O | 68-70 |
| 2-138 | 4-CF₃S—Ph | 1-Me-3-CF₃-4-Cl-5-Pyra | H | Me | H | —CH₂— | O | 1.5049(19.7) |
| 2-139 | 4-CF₃S—Ph | 2-Ph-5-CN—Ph | H | Me | H | —CH₂— | O | 155.7-157.0 |
| 2-140 | 4-CF₃S—Ph | 3-CF₃S—Ph | H | Me | H | —CH₂— | O | 102-108.6 |
| 2-141 | 4-CF₃S—Ph | 3-CF₃SO—Ph | H | Me | H | —CH₂— | O | 105.5-107.1 |
| 2-142 | 4-CF₃S—Ph | 3-CF₃SO₂—Ph | H | Me | H | —CH₂— | O | 42-47 |
| 2-143 | 4-CF₃S—Ph | 3-CF₃S—Ph | H | Me | H | —CH₂— | O | 1.5228(20.3) |
| 2-144 | 4-CF₃S—Ph | 3-CF₃SO—Ph | H | Me | H | —CH₂— | O | 1.5236(20.3) |
| 2-145 | 4-CF₃S—Ph | 3-CF₃SO₂—Ph | H | Me | H | —CH₂— | O | 50-53 |
| 2-146 | 4-CF₃S—Ph | 4-Ph—C≡C—Ph | H | Me | H | —CH₂— | O | 189-191 | m = 1,
R⁴ = H.

TABLE 3

| Comp. No. | ¹H-NMR data |
|---|---|
| 1-7 | 1.40-2.30 (m, 8H), 4.62/4.99 (brs, 1H), 6.38/6.62 (brs, 1H), 6.99-6.97 (m, 2H), 7.16-7.30 (m, 2H), 7.62-7.82 (m, 4H) |
| 1-46 | 1.99 (s, 3H), 2.50 (s, 3H), 4.41 (d, 1H), 4.49 (d, 1H), 7.03 (d, 2H), 7.25 (d, 2H), 7.30 (brs, 3H), 7.59 (d, 2H), 8.18 (d, 1H) |
| 1-50 | 1.97 (s, 3H), 4.40 (d, 1H), 4.47 (d, 1H), 6.65 (brs, 1H), 7.03 (d, 2H), 7.19-7.23 (m, 1H), 7.59 (d, 2H), 7.62 (t, 1H), 7.80-7.91 (m, 1H), 8.55-8.57 (m, 1H) |
| 1-61 | 1.99 (s, 3H), 4.43 (s, 3H), 4.49 (s, 2H), 7.04 (m, 4H), 7.57 (d, 2H), 7.89 (d, 1H), 8.25 (brs, 1H), 8.41 (d, 1H) |
| 1-62 | 1.99 (s, 3H), 2.61 (s, 3H), 4.46 (s, 2H), 7.02-7.09 (m, 4H), 7.58 (d, 2H), 7.92-7.96 (m, 1H), 8.53-8.55 (m, 1H) |
| 1-75 | 1.94 (s, 3H), 4.31 (d, J = 9.2 Hz, 1H), 4.35 (d, J = 9.2 Hz, 1H), 6.24 (br-s, 1H), 6.85-6.91 (m, 2H), 7.25-7.30 (m, 2H), 7.55-7.66 (m, 3H), 7.72 (d, J = 7.9 Hz, 1H) |
| 1-76 | 1.98 (s, 3H), 4.34 (d, J = 9.3 Hz, 1H), 4.42 (d, J = 9.4 Hz, 1H), 6.50 (br-s, 1H), 6.87-6.93 (m, 2H), 7.25-7.30 (m, 2H), 7.61 (t, J = 7.8 Hz, 1H), 7.82 (d, J = 7.7 Hz, 1H), 7.96 (d, J = 7.8 Hz, 1H), 8.02 (s, 1H), |
| 1-79 | 2.03 (s, 3H), 4.54 (d, J = 8.9 Hz, 1H), 4.69 (d, J = 8.9 Hz, 1H), 7.30 (s, 1H), 7.42 (d, J = 8.0 Hz, 1H), 7.71 (d, J = 8.0 Hz, 1H), 7.99 (br-s, 1H), 8.76 (d, J = 2.3 Hz, 1H), 8.89 (d, J = 2.3 Hz, 1H), |

TABLE 3-continued

| Comp. No. | $^1$H-NMR data |
|---|---|
| 1-81 | 2.08 (s, 3H), 4.59 (d, J = 9.1 Hz, 1H), 4.63 (d, J = 9.1 Hz, 1H), 7.56 (d, J = 8.7 Hz, 1H), 7.85 (d, J = 2.4 Hz, 1H), 7.90 (dd, J = 8.7, 2.4 Hz, 1H), 8.07 (br-s, 1H), 8.77 (d, J = 2.3 Hz, 1H), 8.90 (d, J = 2.3 Hz, 1H), |
| 2-72 | 1.08 (s, 9H), 3.68-3.82 (m, 2H), 4.36-4.47 (m, 2H), 5.69 (br, 1H), 6.75 (d, 2H), 7.18-7.46 (m, 6H) |
| 2-73 | 1.07 (s, 9H), 3.52-3.66 (m, 2H), 4.33-4.52 (m, 2H), 5.55 (br, 1H), 6.78 (d, 2H), 7.10-7.33 (m, 6H) |
| 2-74 | 1.03 (s, 9H), 3.49-3.64 (m, 2H), 3.81 (s, 3H), 4.32-4.50 (m, 2H), 5.58 (br, 1H), 6.77 (d, 2H), 6.91 (d, 2H), 7.13 (d, 2H), 7.24 (d, 2H) |
| 2-77 | 0.95 (t, 3H), 1.35-1.55 (m, 2H), 1.95-2.05 (m, 2H), 3.53 (s, 2H), 3.80 (s, 3H), 4.19-4.33 (m, 2H), 5.63 (br, 1H), 6.74 (d, 2H), 6.87 (d, 2H), 7.11 (d, 2H), 7.23 (d, 2H) |
| 2-87 | 1.20-2.10 (m, 8H), 3.48 (s)/3.50 (s) (2H), 4.32 (br)/4.84 (br) (1H), 5.60 (br)/5.90 (br) (1H), 6.67-6.75 (m, 2H), 7.00-7.30 (m, 6H) |
| 2-88 | 1.20-2.10 (m, 8H), 3.43-3.55 (m, 2H), 3.73 (s)/3.87 (s) (3H), 4.26 (br)/4.80 (br) (1H), 5.61 (br)/5.86 (br) (1H), 6.65-7.25 (m, 8H) |
| 2-89 | 1.20-2.00 (m, 8H), 3.49 (s)/3.52 (s) (2H), 4.35 (br)/4.85 (br) (1H), 5.62 (br)/ 5.95 (br) (1H), 6.70-6.80 (m, 2H), 7.00-7.30 (m, 6H) |
| 2-93 | 1.80 (s, 3H), 3.03 (s, 3H), 3.58 (s, 2H), 4.32 (dd, 2H), 5.88 (br, 1H), 6.96 (d, 2H), 7.18 (s, 2H), 7.32 (d, 2H), 7.86 (d, 2H) |

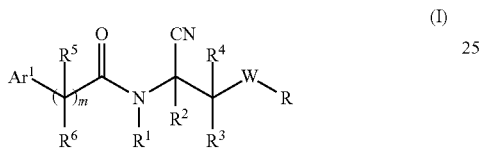

(I)

TABLE 4

$R^4$ = H, m = 0 or 1

| Comp. No. | $Ar^1$ | R | $R^1$ | $R^2$ | $R^3$ | W | $C(R^5)R^6$ | property |
|---|---|---|---|---|---|---|---|---|
| 4-1 | 4-$CF_3$—Ph | n-Octyl | H | Me | H | O | $CH_2$ | 79-81 |
| 4-2 | 4-$OCF_3$—Ph | n-Bu | H | Me | H | O | — | 126-128 |
| 4-3 | 4-$CF_3$—Ph | n-Octyl | H | Me | H | O | — | 103-105 |

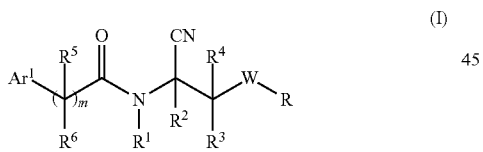

(I)

TABLE 5

$R^1$, $R^3$, $R^4$ = H, $R^2$ = Me, m = 0 or 1

| No. | Ar | R | $C(R^5)R^6$ | W | property |
|---|---|---|---|---|---|
| 5-1 | 4-$CF_3$-3-Py | 2-$CF_3$-5-CN—Ph | — | O | 173.6-173.6 |
| 5-2 | 4-$CF_3$-3-Py | 2-Cl—Ph | — | O | 1.4991 (38.2) |
| 5-3 | 4-$CF_3$-3-Py | 4-$SCF_3$—Ph | — | O | 1.5040 (38.0) |
| 5-4 | 2-Me-3-Py | 2-$CF_3$-5-CN—Ph | — | O | 186.9-188.0 |
| 5-5 | 2-Me-3-Py | 2-Cl—Ph | — | O | 1.4848 (38.0) |
| 5-6 | 2-Me-3-Py | 4-$SCF_3$—Ph | — | O | 93.0-96.7 |
| 5-7 | 2-EtO-3-Py | 2-$CF_3$-5-CN—Ph | — | O | 155.3-157.2 |
| 5-8 | 2-EtO-3-Py | 2-Cl—Ph | — | O | 1.5562 (29.2) |
| 5-9 | 2-EtO-3-Py | 4-$SCF_3$—Ph | — | O | 1.5340 (29.4) |
| 5-10 | 2-MeS-3-Py | 2-$CF_3$-5-CN—Ph | — | O | 86.1-90.3 |
| 5-11 | 2-MeS-3-Py | 2-Cl—Ph | — | O | 51.9-58.7 |
| 5-12 | 2-MeS-3-Py | 4-$SCF_3$—Ph | — | O | 1.4138 (38.0) |
| 5-13 | 6-Me-3-Py | 2-$CF_3$-5-CN—Ph | — | O | 67.4-73.1 |

TABLE 5-continued $R^1, R^3, R^4 = H, R^2 = Me, m = 0$ or $1$

| No. | Ar | R | C(R$^5$)R$^6$ | W | property |
|---|---|---|---|---|---|
| 5-14 | 6-Me-3-Py | 2-Cl—Ph | — | O | 135.5-136.8 |
| 5-15 | 6-Me-3-Py | 4-SCF$_3$—Ph | — | O | 124.2 |
| 5-16 | 6-CF$_3$-3-Py | 2-CF$_3$-5-CN—Ph | — | O | 215.5-216.9 |
| 5-17 | 6-CF$_3$-3-Py | 2-Cl—Ph | — | O | 99.7-100.7 |
| 5-18 | 6-CF$_3$-3-Py | 4-SCF$_3$—Ph | — | O | 1.3800 (37.5) |
| 5-19 | 2-Cl-6-MeO-4-Py | 2-CF$_3$-5-CN—Ph | — | O | 80.9-90.4 |
| 5-20 | 2-Cl-6-MeO-4-Py | 2-Cl—Ph | — | O | 85.9-97.5 |
| 5-21 | 2-Cl-6-MeO-4-Py | 4-SCF$_3$—Ph | — | O | 111.1-119.1 |
| 5-22 | 1-Me-4-Pyra | 2-CF$_3$-5-CN—Ph | — | O | 236.7-240.5 |
| 5-23 | 1-Me-4-Pyra | 2-Cl—Ph | — | O | 142.8-147.8 |
| 5-24 | 1-Me-4-Pyra | 4-SCF$_3$—Ph | — | O | 177.3-177.9 |
| 5-25 | 1,3-Me$_2$-4-Pyra | 2-CF$_3$-5-CN—Ph | — | O | 144.7-149.7 |
| 5-26 | 1,3-Me$_2$-4-Pyra | 2-Cl—Ph | — | O | 68.3-73.3 |
| 5-27 | 1,3-Me$_2$-4-Pyra | 4-SCF$_3$—Ph | — | O | 94.6-99.6 |
| 5-28 | 1-Me-3-CF$_3$-4-Pyra | 2-CF$_3$-5-CN—Ph | — | O | 202.6-202.9 |
| 5-29 | 1-Me-3-CF$_3$-4-Pyra | 2-Cl—Ph | — | O | 169.0-171.4 |
| 5-30 | 1-Me-3-CF$_3$-4-Pyra | 4-SCF$_3$—Ph | — | O | 149.5-154.4 |
| 5-31 | 1-Me-5-CF$_3$-4-Pyra | 2-CF$_3$-5-CN—Ph | — | O | 197.7-199.0 |
| 5-32 | 1-Me-5-CF$_3$-4-Pyra | 2-Cl—Ph | — | O | 167.9-170.0 |
| 5-33 | 1-Me-5-CF$_3$-4-Pyra | 4-SCF$_3$—Ph | — | O | 150.9-156.9 |
| 5-34 | 1,5-Me$_2$-3-CF$_3$-4-Pyra | 2-CF$_3$-5-CN—Ph | — | O | 162.4-172.9 |
| 5-35 | 1,5-Me$_2$-3-CF$_3$-4-Pyra | 2-Cl—Ph | — | O | 129.0-132.4 |
| 5-36 | 1,5-Me$_2$-3-CF$_3$-4-Pyra | 4-SCF$_3$—Ph | — | O | 112.1-113.2 |
| 5-37 | 1-Me-3-OCH$_2$OMe-5-PhO-4-Pyra | 2-CF$_3$-5-CN—Ph | — | O | 124.1-128.7 |
| 5-38 | 1-Me-3-OCH$_2$OMe-5-PhO-4-Pyra | 2-Cl—Ph | — | O | 1.4310 (35.5) |
| 5-39 | 1-Me-3-OCH$_2$OMe-5-PhO-4-Pyra | 4-SCF$_3$—Ph | — | O | 1.4320 (35.8) |
| 5-40 | 1-Me-5-i-PrO-4-Pyra | 2-CF$_3$-5-CN—Ph | — | O | 59.5-65.8 |
| 5-41 | 1-Me-5-i-PrO-4-Pyra | 2-Cl—Ph | — | O | 1.5387 (34.0) |
| 5-42 | 1-Me-5-i-PrO-4-Pyra | 4-SCF$_3$—Ph | — | O | 1.5179 (34.2) |
| 5-43 | 1,3-Me$_2$-5-PhO-4-Pyra | 2-CF$_3$-5-CN—Ph | — | O | 61.7-77.2 |
| 5-44 | 1,3-Me$_2$-5-PhO-4-Pyra | 2-Cl—Ph | — | O | 1.4908 (34.5) |
| 5-45 | 1,3-Me$_2$-5-PhO-4-Pyra | 4-SCF$_3$—Ph | — | O | 1.5489 (37.0) |
| 5-46 | 1-Me-3-CF$_3$-5-PhO-4-Pyra | 2-CF$_3$-5-CN—Ph | — | O | 177.5 |
| 5-47 | 1-Me-3-CF$_3$-5-PhO-4-Pyra | 2-Cl—Ph | — | O | 1.5311 (34.0) |
| 5-48 | 1-Me-3-CF$_3$-5-PhO-4-Pyra | 4-SCF$_3$—Ph | — | O | 58.2-60.4 |
| 5-49 | 1,3-Me$_2$-5-Cl-4-Pyra | 2-CF$_3$-5-CN—Ph | — | O | 55.2-58.2 |
| 5-50 | 1,3-Me$_2$-5-Cl-4-Pyra | 2-Cl—Ph | — | O | 105.6-110.5 |
| 5-51 | 1,3-Me$_2$-5-Cl-4-Pyra | 4-SCF$_3$—Ph | — | O | 14589 (38.1) |
| 5-52 | 1,3-Me$_2$-4-Cl-5-Pyra | 2-CF$_3$-5-CN—Ph | — | O | 106.3-106.9 |
| 5-53 | 1,3-Me$_2$-4-Cl-5-Pyra | 2-Cl—Ph | — | O | 121.9-123.2 |
| 5-54 | 1,3-Me$_2$-4-Cl-5-Pyra | 4-SCF$_3$—Ph | — | O | 1.4803 (35.1) |
| 5-55 | 1,3-Me$_2$-5-Pyra | 2-CF$_3$-5-CN—Ph | — | O | 59.6-64.6 |
| 5-56 | 1,3-Me$_2$-5-Pyra | 2-Cl—Ph | — | O | 125.8-127.5 |
| 5-57 | 1,3-Me$_2$-5-Pyra | 4-SCF$_3$—Ph | — | O | 122.1-122.8 |
| 5-58 | 1,3,4-Me$_3$-5-Pyra | 2-CF$_3$-5-CN—Ph | — | O | 93.8-98.8 |
| 5-59 | 1,3,4-Me$_3$-5-Pyra | 2-Cl—Ph | — | O | 1.5431 (36.2) |
| 5-60 | 1,3,4-Me$_3$-5-Pyra | 4-SCF$_3$—Ph | — | O | 95.3-97.7 |
| 5-61 | 1-Me-3-i-Pr-5-Pyra | 2-CF$_3$-5-CN—Ph | — | O | 171.5-171.7 |
| 5-62 | 1-Me-3-i-Pr-5-Pyra | 2-Cl—Ph | — | O | 118.4-123.9 |
| 5-63 | 1-Me-3-i-Pr-5-Pyra | 4-SCF$_3$—Ph | — | O | 140.1-140.3 |
| 5-64 | 1-Me-3-c-Pr-5-Pyra | 2-CF$_3$-5-CN—Ph | — | O | 65.0-70.0 |
| 5-65 | 1-Me-3-i-Pr-5-Pyra | 2-Cl—Ph | — | O | 1.5541 (38.0) |
| 5-66 | 1-Me-3-i-Pr-5-Pyra | 4-SCF$_3$—Ph | — | O | 133.3 |
| 5-67 | 1-Me-3-Ph-5-Pyra | 2-CF$_3$-5-CN—Ph | — | O | 94.0-99.0 |
| 5-68 | 1-Me-3-Ph-5-Pyra | 2-Cl—Ph | — | O | 147.8-149.0 |
| 5-69 | 1-Me-3-Ph-5-Pyra | 4-SCF$_3$—Ph | — | O | 59.9-64.9 |
| 5-70 | 1-Me-3-MeO-5-Pyra | 2-CF$_3$-5-CN—Ph | — | O | 61.4-66.4 |
| 5-71 | 1-Me-3-MeO-5-Pyra | 2-Cl—Ph | — | O | 1.5478 (38.0) |
| 5-72 | 1-Me-3-MeO-5-Pyra | 4-SCF$_3$—Ph | — | O | 1.5292 (38.0) |
| 5-73 | 1-Me-3-CHF$_2$O-5-Pyra | 2-CF$_3$-5-CN—Ph | — | O | 73.6-75.4 |
| 5-74 | 1-Me-3-CHF$_2$O-5-Pyra | 2-Cl—Ph | — | O | 1.5302 (35.1) |
| 5-75 | 1-Me-3-CHF$_2$O-5-Pyra | 4-SCF$_3$—Ph | — | O | 111.9-112.8 |
| 5-76 | 1,3-Me$_2$-4-MeO-5-Pyra | 2-CF$_3$-5-CN—Ph | — | O | 59.5-64.5 |
| 5-77 | 1,3-Me$_2$-4-MeO-5-Pyra | 2-Cl—Ph | — | O | 128.7-130.4 |
| 5-78 | 1,3-Me$_2$-4-MeO-5-Pyra | 4-SCF$_3$—Ph | — | O | 90.7-92.6 |
| 5-79 | 1-Me-3-CF$_3$-4-CO$_2$Et-5-Pyra | 2-CF$_3$-5-CN—Ph | — | O | 198.2-198.4 |
| 5-80 | 1-Me-3-CF$_3$-4-CO$_2$Et-5-Pyra | 2-Cl—Ph | — | O | 113.5-116.6 |
| 5-81 | 1-Me-3-CF$_3$-4-CO$_2$Et-5-Pyra | 4-SCF$_3$—Ph | — | O | 1.4943 (36.0) |
| 5-82 | 3-Me-1-Ph-5-Pyra | 2-CF$_3$-5-CN—Ph | — | O | 74.2-84.8 |
| 5-83 | 3-Me-1-Ph-5-Pyra | 2-Cl—Ph | — | O | 59.7-64.7 |
| 5-84 | 3-Me-1-Ph-5-Pyra | 4-SCF$_3$—Ph | — | O | 162.2-164.2 |
| 5-85 | 1,5-Me$_2$-4-Cl-3-Pyra | 2-CF$_3$-5-CN—Ph | — | O | 75.4-80.4 |
| 5-86 | 1,5-Me$_2$-4-Cl-3-Pyra | 2-Cl—Ph | — | O | 140 |
| 5-87 | 1,5-Me$_2$-4-Cl-3-Pyra | 4-SCF$_3$—Ph | — | O | 59.4-62.4 |
| 5-88 | 1,5-Me$_2$-3-Pyra | 2-CF$_3$-5-CN—Ph | — | O | 62.3-67.3 |
| 5-89 | 1,5-Me$_2$-3-Pyra | 2-Cl—Ph | — | O | 1.5150 (31.0) |

TABLE 5-continued

R$^1$, R$^3$, R$^4$ = H, R$^2$ = Me, m = 0 or 1

| No. | Ar | R | C(R$^5$)R$^6$ | W | property |
|---|---|---|---|---|---|
| 5-90 | 1,5-Me$_2$-3-Pyra | 4-SCF$_3$—Ph | — | O | 101.6-108.9 |
| 5-91 | 1-Me-5-c-Pr-3-Pyra | 2-CF$_3$-5-CN—Ph | — | O | 68.8-73.8 |
| 5-92 | 1-Me-5-c-Pr-3-Pyra | 2-Cl—Ph | — | O | 155.7-156.3 |
| 5-93 | 1-Me-5-c-Pr-3-Pyra | 4-SCF$_3$—Ph | — | O | 114.2-115.9 |
| 5-94 | 1-Me-5-MeO-3-Pyra | 2-CF$_3$-5-CN—Ph | — | O | 169.8-170.4 |
| 5-95 | 1-Me-5-MeO-3-Pyra | 2-Cl—Ph | — | O | 178.1 |
| 5-96 | 1-Me-5-MeO-3-Pyra | 4-SCF$_3$—Ph | — | O | 76.9-81.0 |
| 5-97 | 1-Ph-3-Pyra | 2-CF$_3$-5-CN—Ph | — | O | 84.5-89.5 |
| 5-98 | 1-Ph-3-Pyra | 2-Cl—Ph | — | O | 92.9-97.2 |
| 5-99 | 1-Ph-3-Pyra | 4-SCF$_3$—Ph | — | O | 98.9-101.1 |
| 5-100 | 5-Me-1-Ph-3-Pyra | 2-CF$_3$-5-CN—Ph | — | O | 69.8-98.3 |
| 5-101 | 5-Me-1-Ph-3-Pyra | 2-Cl—Ph | — | O | 60.8-65.8 |
| 5-102 | 5-Me-1-Ph-3-Pyra | 4-SCF$_3$—Ph | — | O | 163.2-163.8 |
| 5-103 | 4-Me-5-MeO-1-Ph-3-Pyra | 2-CF$_3$-5-CN—Ph | — | O | 71.6-76.6 |
| 5-104 | 4-Me-5-MeO-1-Ph-3-Pyra | 2-Cl—Ph | — | O | 111.5-140.8 |
| 5-105 | 4-Me-5-MeO-1-Ph-3-Pyra | 4-SCF$_3$—Ph | — | O | 140.5 |
| 5-106 | 5-Br-2-Py | 2-CF$_3$-5-CN—Ph | CF$_2$ | O | 61.5-71.6 |
| 5-107 | 5-Br-2-Py | 2-Cl—Ph | CF$_2$ | O | 104.8-109.8 |
| 5-108 | 5-Br-2-Py | 4-SCF$_3$—Ph | CF$_2$ | O | 93.8-99.4 |
| 5-109 | 2-Py | 2-CF$_3$-5-CN—Ph | CF$_2$ | O | 1.5096 (36.7) |
| 5-110 | 2-Py | 2-Cl—Ph | CF$_2$ | O | 1.5339 (29.5) |
| 5-111 | 2-Py | 4-SCF$_3$—Ph | CF$_2$ | O | 1.5100 (29.4) |
| 5-112 | 4-CF$_3$S—Ph | 2-F—Ph | — | O | 107.5-112.5 |
| 5-113 | 4-CF$_3$S—Ph | 2-F—Ph | CH$_2$ | O | 112.5 |
| 5-114 | 4-CF$_3$S—Ph | 3-F—Ph | — | O | 89.0-94.0 |
| 5-115 | 4-CF$_3$S—Ph | 3-F—Ph | CH$_2$ | O | 87.9 |
| 5-116 | 4-CF$_3$S—Ph | 4-F—Ph | — | O | 138.5-139.5 |
| 5-117 | 4-CF$_3$S—Ph | 4-F—Ph | CH$_2$ | O | 141.7 |
| 5-118 | 4-CF$_3$S—Ph | 2-MeO—Ph | — | O | 72.9-77.9 |
| 5-119 | 4-CF$_3$S—Ph | 2-MeO—Ph | CH$_2$ | O | 78.2-82.1 |
| 5-120 | 4-CF$_3$S—Ph | 3-MeO—Ph | — | O | 107.4-112.4 |
| 5-121 | 4-CF$_3$S—Ph | 3-MeO—Ph | CH$_2$ | O | 96.0-100.2 |
| 5-122 | 4-CF$_3$S—Ph | 4-CN—Ph | — | O | 157.0-157.9 |
| 5-123 | 4-CF$_3$S—Ph | 4-MeO—Ph | CH$_2$ | O | 106.7-111.9 |
| 5-124 | 4-CF$_3$S—Ph | 4-CN—Ph | — | O | 62.7-67.7 |
| 5-125 | 4-CF$_3$S—Ph | 4-CN—Ph | CH$_2$ | O | 71.5-76.5 |
| 5-126 | 4-CF$_3$S—Ph | 4-NMe$_2$—Ph | — | O | 177.5 |
| 5-127 | 4-CF$_3$S—Ph | 4-NMe$_2$—Ph | CH$_2$ | O | 137 |
| 5-128 | 4-CF$_3$S—Ph | 4-NHAc—Ph | — | O | 120.4-125.4 |
| 5-129 | 4-CF$_3$S—Ph | 4-NHAc—Ph | CH$_2$ | O | 194.4 |
| 5-130 | 4-CF$_3$S—Ph | 4-NHCO$_2$Me—Ph | — | O | 132.4-132.7 |
| 5-131 | 4-CF$_3$S—Ph | 4-NHCO$_2$Me—Ph | CH$_2$ | O | 120.0-122.4 |
| 5-132 | 4-CF$_3$S—Ph | 4-NHCONHMe—Ph | — | O | 102.4-103.6 |
| 5-133 | 4-CF$_3$S—Ph | 4-NHCONHMe—Ph | CH$_2$ | O | 183.8-185.4 |
| 5-134 | 4-CF$_3$S—Ph | 4-Ac—Ph | — | O | 144.0-145.7 |
| 5-135 | 4-CF$_3$S—Ph | 4-Ac—Ph | CH$_2$ | O | 1.5431 (36.0) |
| 5-136 | 4-CF$_3$S—Ph | 4-CO$_2$Me—Ph | — | O | 135.1-138.9 |
| 5-137 | 4-CF$_3$S—Ph | 4-CO$_2$Me—Ph | CH$_2$ | O | 110.3-112.7 |
| 5-138 | 4-CF$_3$S—Ph | 4-CONH$_2$—Ph | — | O | 168.1-173.1 |
| 5-139 | 4-CF$_3$S—Ph | 4-CONH$_2$—Ph | CH$_2$ | O | 195.2-195.5 |
| 5-140 | 2-CF$_3$S—Ph | 2-CF$_3$-5-CN—Ph | — | O | 167.2-168.9 |
| 5-141 | 3-CF$_3$S—Ph | 2-CF$_3$-5-CN—Ph | — | O | 118.0-128.2 |
| 5-142 | 2-CF$_3$—Ph | 2-CF$_3$-5-CN—Ph | — | O | 200.3-203.4 |
| 5-143 | 3-CF$_3$—Ph | 2-CF$_3$-5-CN—Ph | — | O | 63.5-68.5 |
| 5-144 | 4-CF$_3$—Ph | 2-CF$_3$-5-CN—Ph | — | O | 155.0-165.1 |
| 5-145 | 4-CF$_3$S—Ph | 4-(2-Py-C≡C—)Ph | — | O | 1.5898 (38.1) |
| 5-146 | 4-CF$_3$S—Ph | 4-(3-Py-C≡C—)Ph | — | O | 136.6-140.0 |
| 5-147 | 4-CF$_3$S—Ph | 4-(4-Py-C≡C—)Ph | — | O | 184.4-185.6 |
| 5-148 | 4-CF$_3$S—Ph | 4-(2-Py-C≡C—)Ph | CH$_2$ | O | 194.4-195.7 |
| 5-149 | 4-CF$_3$S—Ph | 4-(3-Py-C≡C—)Ph | CH$_2$ | O | 188.3-193.5 |
| 5-150 | 4-CF$_3$S—Ph | 4-(4-Py-C≡C—)Ph | CH$_2$ | O | 178.7-180.0 |
| 5-151 | 4-CF$_3$S—Ph | 3-Cl-5-CF$_3$-2-Py | — | O | |
| 5-152 | 4-CF$_3$S—Ph | 5-Cl-2-Py | — | O | 100.8-110.2 |
| 5-153 | 4-CF$_3$S—Ph | 3,5-Cl$_2$-2-Py | — | O | 81 |
| 5-154 | 4-CF$_3$S—Ph | 2-Cl-5-Py | — | O | 160.4-164.2 |
| 5-155 | 4-CF$_3$S—Ph | 4-Cl-2-Thz | — | O | 122.0-127.6 |
| 5-156 | 4-CF$_3$S—Ph | 4-Cl—Ph | — | S | 117.8-121.2 |
| 5-157 | 4-CF$_3$S—Ph | 4-F—Ph | — | S | 90.0-92.9 |
| 5-158 | 4-CF$_3$S—Ph | 4-Cl—Ph | — | NMe | 132.1-133.3 |
| 5-159 | 4-CF$_3$S—Ph | 4-F—Ph | — | NMe | 123.4 |
| 5-160 | 4-CF$_3$S—Ph | 4-CF$_3$—Ph | — | NMe | 129.0-131.2 |
| 5-161 | 4-CF$_3$S—Ph | 2-Py | CH$_2$ | O | 135.8-136.8 |

TABLE 5-continued

| | R$^1$, R$^3$, R$^4$ = H, R$^2$ = Me, m = 0 or 1 | | | | |
|---|---|---|---|---|---|
| No. | Ar | R | C(R$^5$)R$^6$ | W | property |
| 5-162 | 4-CF$_3$S—Ph | 5-CF$_3$-2-Py | CH$_2$ | O | 133.7-134.7 |
| 5-163 | 4-CF$_3$S—Ph | 3-CF$_3$-2-Pyz | CH$_2$ | O | 134.8-136.8 |

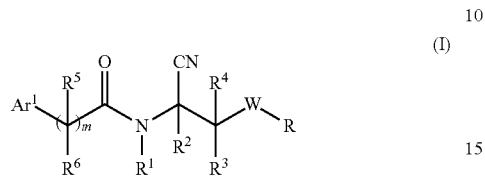

(I)

TABLE 6

| | R$^1$, R$^3$, R$^4$ = H, R$^2$ = Me, W = O, m = 0 or 1 | | | |
|---|---|---|---|---|
| No. | Ar$^1$ | R | C(R$^5$)R$^6$ | property |
| 6-1 | 4-c-Pr-5-Pym | 2-CF$_3$-5-CN—Ph | — | 90.0-100.0 |
| 6-2 | 4-c-Pr-5-Pym | 2-Cl—Ph | — | 58.9-62.2 |
| 6-3 | 3-c-Pr-5-Pym | 4-SCF$_3$—Ph | — | 155.9-163.3 |
| 6-4 | 3-MeS-2-Pyz | 2-CF$_3$-5-CN—Ph | — | 85.5-87.5 |
| 6-5 | 3-MeS-2-Pyz | 2-Cl—Ph | — | 136.7-139.8 |
| 6-6 | 3-MeS-2-Pyz | 4-SCF$_3$—Ph | — | 56.4-59.4 |
| 6-7 | 2-Ph-5-Pym | 2-CF$_3$-5-CN—Ph | — | 224.0-226.8 |
| 6-8 | 2-Ph-5-Pym | 2-Cl—Ph | — | 211.7-218.8 |
| 6-9 | 2-Ph-5-Pym | 4-SCF$_3$—Ph | — | 216.6-218.0 |
| 6-10 | 2-(4-Py)-5-Pym | 2-CF$_3$-5-CN—Ph | — | 263.7-265.9 |
| 6-11 | 2-(4-Py)-5-Pym | 2-Cl—Ph | — | 245.1-247.5 |
| 6-12 | 2-(4-Py)-5-Pym | 4-SCF$_3$—Ph | — | 234.5-236.6 |
| 6-13 | 2-PhNH-5-Pym | 2-CF$_3$-5-CN—Ph | — | 236.6-238.5 |
| 6-14 | 2-PhNH-5-Pym | 2-Cl—Ph | — | 180.7-186.6 |
| 6-15 | 2-PhNH-5-Pym | 4-SCF$_3$—Ph | — | 211.9-212.8 |
| 6-16 | 2,4-Me$_2$-5-Thz | 2-CF$_3$-5-CN—Ph | — | 161.4-162.7 |
| 6-17 | 2,4-Me$_2$-5-Thz | 2-Cl—Ph | — | 1.5260 (36.0) |
| 6-18 | 2,4-Me$_2$-5-Thz | 4-SCF$_3$—Ph | — | 130.2-131.5 |
| 6-19 | 2-Me-4-CF$_3$-5-Thz | 2-CF$_3$-5-CN—Ph | — | 63.4-79.0 |
| 6-20 | 2-Me-4-CF$_3$-5-Thz | 2-Cl—Ph | — | 1.4934 (29.8) |
| 6-21 | 2-Me-4-CF$_3$-5-Thz | 4-SCF$_3$—Ph | — | 1.4428 (29.6) |
| 6-22 | 4-Me-2-Ph-5-Thz | 2-CF$_3$-5-CN—Ph | — | 67.6-72.7 |
| 6-23 | 4-Me-2-Ph-5-Thz | 2-Cl—Ph | — | 152.4-155.5 |
| 6-24 | 4-Me-2-Ph-5-Thz | 4-SCF$_3$—Ph | — | 130.1-134.6 |
| 6-25 | 4-Me-2-(4-Me—Ph)-5-Thz | 2-CF$_3$-5-CN—Ph | — | 219.0-220.7 |
| 6-26 | 4-Me-2-(4-Me—Ph)-5-Thz | 2-Cl—Ph | — | 180.7-181.0 |
| 6-27 | 4-Me-2-(4-Me—Ph)-5-Thz | 4-SCF$_3$—Ph | — | 142.1-153.4 |
| 6-28 | 4-Me-2-(4-Cl—Ph)-5-Thz | 2-CF$_3$-5-CN—Ph | — | 214.0-216.0 |
| 6-29 | 4-Me-2-(4-Cl—Ph)-5-Thz | 2-Cl—Ph | — | 170.8-171.1 |
| 6-30 | 4-Me-2-(4-Cl—Ph)-5-Thz | 4-SCF$_3$—Ph | — | 71.5-77.3 |
| 6-31 | 2-CO$_2$Et-4-Ph-5-Thz | 2-CF$_3$-5-CN—Ph | — | 91.4-93.9 |
| 6-32 | 2-CO$_2$Et-4-Ph-5-Thz | 2-Cl—Ph | — | 166.7-167.2 |
| 6-33 | 2-CO$_2$Et-4-Ph-5-Thz | 4-SCF$_3$—Ph | — | 158.9-160.0 |
| 6-34 | 2-NHMe-4-Me-5-Thz | 2-CF$_3$-5-CN—Ph | — | |
| 6-35 | 2-NHMe-4-Me-5-Thz | 2-Cl—Ph | — | |
| 6-36 | 2-NHMe-4-Me-5-Thz | 4-SCF$_3$—Ph | — | |
| 6-37 | 2-NHEt-4-Me-5-Thz | 2-CF$_3$-5-CN—Ph | — | |
| 6-38 | 2-NHEt-4-Me-5-Thz | 2-Cl—Ph | — | |
| 6-39 | 2-NHEt-4-Me-5-Thz | 4-SCF$_3$—Ph | — | |
| 6-40 | 2-NMe$_2$-4-Et-5-Thz | 2-CF$_3$-5-CN—Ph | — | 69.6-74.6 |
| 6-41 | 2-NMe$_2$-4-Et-5-Thz | 2-Cl—Ph | — | 56.1-59.0 |
| 6-42 | 2-NMe$_2$-4-Et-5-Thz | 4-SCF$_3$—Ph | — | 105.9-118.5 |
| 6-43 | 2-NMe$_2$-4-c-Pr-5-Thz | 2-CF$_3$-5-CN—Ph | — | |
| 6-44 | 2-NMe$_2$-4-c-Pr-5-Thz | 2-Cl—Ph | — | |
| 6-45 | 2-NMe$_2$-4-c-Pr-5-Thz | 4-SCF$_3$—Ph | — | |
| 6-46 | 2-NMe$_2$-4-Ph-5-Thz | 2-CF$_3$-5-CN—Ph | — | |
| 6-47 | 2-NMe$_2$-4-Ph-5-Thz | 2-Cl—Ph | — | |
| 6-48 | 2-NMe$_2$-4-Ph-5-Thz | 4-SCF$_3$—Ph | — | |
| 6-49 | 2-NHCO$_2$-t-Bu-4-Me-5-Thz | 2-CF$_3$-5-CN—Ph | — | 189.1-193.6 |
| 6-50 | 2-NHCO$_2$-t-Bu-4-Me-5-Thz | 2-Cl—Ph | — | 174.6-179.8 |
| 6-51 | 2-NH-CO$_2$-t-Bu-4-Me-5-Thz | 4-SCF$_3$—Ph | — | 110.8-115.8 |
| 6-52 | 2-NMe$_2$-4-i-Pr-5-Thz | 2-CF$_3$-5-CN—Ph | — | |
| 6-53 | 2-NMe$_2$-4-i-Pr-5-Thz | 2-Cl—Ph | — | 73.4-78.4 |

TABLE 6-continued $R^1, R^3, R^4 = H, R^2 = Me, W = O, m = 0$ or 1

| No. | Ar$^1$ | R | C(R$^5$)R$^6$ | property |
|---|---|---|---|---|
| 6-54 | 2-NMe$_2$-4-i-Pr-5-Thz | 4-SCF$_3$—Ph | — | 62.6 |
| 6-55 | 2-piperidino-4-Me-5-Thz | 2-CF$_3$-5-CN—Ph | — | |
| 6-56 | 2-piperidino-4-Me-5-Thz | 2-Cl—Ph | — | |
| 6-57 | 2-piperidino-4-Me-5-Thz | 4-SCF$_3$—Ph | — | |
| 6-58 | 2-NHC$_2$H$_4$OMe-4-CF$_3$-5-Thz | 2-CF$_3$-5-CN—Ph | — | 66.5-71.5 |
| 6-59 | 2-NHC$_2$H$_4$OMe-4-CF$_3$-5-Thz | 2-Cl—Ph | — | 1.4490 (33.3) |
| 6-60 | 2-NHC$_2$H$_4$OMe-4-CF$_3$-5-Thz | 4-SCF$_3$—Ph | — | 1.4367 (33.5) |
| 6-61 | 3,5-Me$_2$-4-Iox | 2-CF$_3$-5-CN—Ph | — | 175.6-178.0 |
| 6-62 | 3,5-Me$_2$-4-Iox | 2-Cl—Ph | — | 1.4145 (36.0) |
| 6-63 | 3,5-Me$_2$-4-Iox | 4-SCF$_3$—Ph | — | 110.0-114.8 |
| 6-64 | 3-Cl-5-Me-4-Iox | 2-CF$_3$-5-CN—Ph | — | 132.6-136.1 |
| 6-65 | 3-Cl-5-Me-4-Iox | 2-Cl—Ph | — | 125.6-125.9 |
| 6-66 | 3-Cl-5-Me-4-Iox | 4-SCF$_3$—Ph | — | 1.5240 (36.0) |
| 6-67 | 4-Me-5-Ox | 2-CF$_3$-5-CN—Ph | — | 174.0-175.6 |
| 6-68 | 4-Me-5-Ox | 2-Cl—Ph | — | 153.1-157.9 |
| 6-69 | 4-Me-5-Ox | 4-SCF$_3$—Ph | — | 136.1-139.9 |
| 6-70 | 2-furyl | 2-CF$_3$-5-CN—Ph | — | 63.0-68.0 |
| 6-71 | 2-furyl | 2-Cl—Ph | — | 1.5590 (33.9) |
| 6-72 | 2-furyl | 4-SCF$_3$—Ph | — | 1.5331 (36.3) |
| 6-73 | 4-methyl-furazan-3-yl | 2-CF$_3$-5-CN—Ph | — | 58.4-62.2 |
| 6-74 | 4-methyl-furazan-3-yl | 2-Cl—Ph | — | 1.3521 (36.0) |
| 6-75 | 4-methyl-furazan-3-yl | 4-SCF$_3$—Ph | — | 1.5115 (33.2) |
| 6-76 | 4-methyl-3,4-dihydro-2H-pyrido[3,2-b][1,4]oxazin-7-yl | 2-CF$_3$-5-CN—Ph | — | 57.3-60.8 |
| 6-77 | 4-methyl-3,4-dihydro-2H-pyrido[3,2-b][1,4]oxazin-7-yl | 2-Cl—Ph | — | 172.9-174.2 |
| 6-78 | 4-methyl-3,4-dihydro-2H-pyrido[3,2-b][1,4]oxazin-7-yl | 4-SCF$_3$—Ph | — | 217.9-233.7 |
| 6-79 | 1-(4-methoxyphenyl)-1H-1,2,4-triazol-3-yl | 2-CF$_3$-5-CN—Ph | — | 80.2-85.2 |

TABLE 6-continued

R¹, R³, R⁴ = H, R² = Me, W = O, m = 0 or 1

| No. | Ar¹ | R | C(R⁵)R⁶ | property |
|---|---|---|---|---|
| 6-80 | 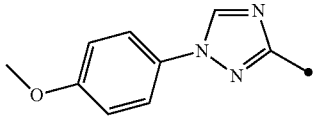 | 2-Cl—Ph | — | 59.6-67.3 |
| 6-81 | 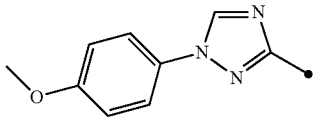 | 4-SCF₃—Ph | — | 62.9-67.3 |
| 6-82 | 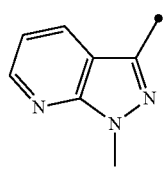 | 2-CF₃-5-CN—Ph | — | 181.8-182.7 |
| 6-83 | 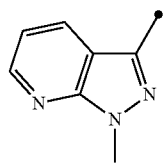 | 2-Cl—Ph | — | 60.2-65.2 |
| 6-84 | 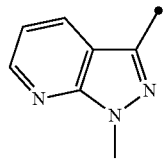 | 4-SCF₃—Ph | — | 131.0-136.0 |
| 6-85 | 3-thienyl | 2-CF₃-5-CN—Ph | — | 60.9-65.9 |
| 6-86 | 3-thienyl | 2-Cl—Ph | — | 152.7-154.0 |
| 6-87 | 3-thienyl | 4-SCF₃—Ph | — | 160.5-160.8 |
| 6-88 | 3-Me-2-thienyl | 2-CF₃-5-CN—Ph | — | 65.2-70.2 |
| 6-89 | 3-Me-2-thienyl | 2-Cl—Ph | — | 1.5743 (32.0) |
| 6-90 | 3-Me-2-thienyl | 4-SCF₃—Ph | — | 1.4972 (36.2) |
| 6-91 | 3-MeO-2-thienyl | 2-CF₃-5-CN—Ph | — | 228.7-231.5 |
| 6-92 | 3-MeO-2-thienyl | 2-Cl—Ph | — | 148.3-153.3 |
| 6-93 | 3-MeO-2-thienyl | 4-SCF₃—Ph | — | 1.5482 (35.4) |
| 6-94 | 5-Me-2-thienyl | 2-CF₃-5-CN—Ph | — | 76.3-81.3 |
| 6-95 | 5-Me-2-thienyl | 2-Cl—Ph | — | 148.3 |
| 6-96 | 5-Me-2-thienyl | 4-SCF₃—Ph | — | 152.2-155.0 |
| 6-97 | 5-MeO-2-thienyl | 2-CF₃-5-CN—Ph | — | 72.2-77.2 |
| 6-98 | 5-MeO-2-thienyl | 2-Cl—Ph | — | 101.5-106.5 |
| 6-99 | 5-MeO-2-thienyl | 4-SCF₃—Ph | — | 118.5-123.5 |
| 6-100 | 5-morpholino-2-thienyl | 2-CF₃-5-CN—Ph | — | 191.0-196.0 |
| 6-101 | 5-morpholino-2-thienyl | 2-Cl—Ph | — | 204.8-205.7 |
| 6-102 | 5-morpholino-2-thienyl | 4-SCF₃—Ph | — | 198.4-200.2 |
| 6-103 | 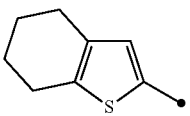 | 2-CF₃-5-CN—Ph | — | 89.9-94.7 |
| 6-104 | 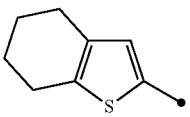 | 2-Cl—Ph | — | 200.2 |

TABLE 6-continued $R^1, R^3, R^4 = H, R^2 = Me, W = O, m = 0$ or 1

| No. | Ar$^1$ | R | C(R$^5$)R$^6$ | property |
|---|---|---|---|---|
| 6-105 | 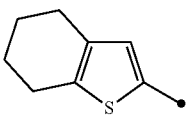 | 4-SCF$_3$—Ph | — | 200.3-205.3 |
| 6-106 | 4-MeO-3-thienyl | 2-CF$_3$-5-CN—Ph | — | 173.2 |
| 6-107 | 4-MeO-3-thienyl | 2-Cl—Ph | — | 99.9-103.4 |
| 6-108 | 4-MeO-3-thienyl | 4-SCF$_3$—Ph | — | 1.5350 (36.2) |
| 6-109 | 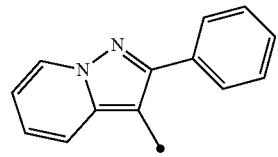 | 2-CF$_3$-5-CN—Ph | — | 175.0-176.7 |
| 6-110 | 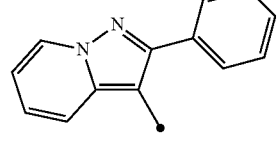 | 2-Cl—Ph | — | 66.3-71.3 |
| 6-111 | 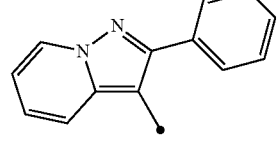 | 4-SCF$_3$—Ph | — | 67.8-72.8 |
| 6-112 | 2-CO$_2$Et-4-(4-F—Ph)-5-Thz | 2-CF$_3$-5-CN—Ph | CH$_2$ | 100.2-105.2 |
| 6-113 | 2-CO$_2$Et-4-(4-F—Ph)-5-Thz | 2-Cl—Ph | CH$_2$ | 168.1 |
| 6-114 | 2-CO$_2$Et-4-(4-F—Ph)-5-Thz | 4-SCF$_3$—Ph | CH$_2$ | 177.0-182.0 |
| 6-115 | 2-CO$_2$Me-4-Ph-5-Thz | 2-CF$_3$-5-CN—Ph | CH$_2$ | 104.5-109.5 |
| 6-116 | 2-CO$_2$Me-4-Ph-5-Thz | 2-Cl—Ph | CH$_2$ | 195.2-195.5 |
| 6-117 | 2-CO$_2$Me-4-Ph-5-Thz | 4-SCF$_3$—Ph | CH$_2$ | 185.3-190.3 |
| 6-118 | 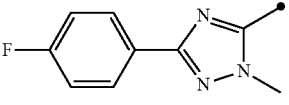 | 2-CF$_3$-5-CN—Ph | CH$_2$ | 138.1 |
| 6-119 | 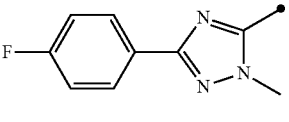 | 2-Cl—Ph | CH$_2$ | 148.0-153.0 |
| 6-120 | 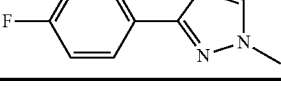 | 4-SCF$_3$—Ph | CH$_2$ | 159.3-160.0 |

While the aminoacetonitrile compound represented by the formula (I) of the present invention or a pharmacologically acceptable salt thereof can be directly administered singly, generally, it is desirably formulated into various pharmaceutical preparations. The pharmaceutical preparations can be produced by a conventional method for pharmaceutical drug formulation by mixing the active ingredient with one or more kinds of pharmacologically acceptable carriers.

A pharmacologically acceptable salt of the aminoacetonitrile compound represented by the formula (I) of the present invention includes an acid addition salt, a metal salt, an ammonium salt, an organic amine addition salt, an amino acid addition salt and the like, each of which is pharmacologically acceptable. The pharmacologically acceptable acid addition salt includes respective inorganic acid salts with hydrochloric acid, hydrobromic acid, sulfuric acid, nitric acid, phosphoric acid, boric acid and the like, and organic acid salts with carboxylic acids including formic acid, acetic acid, propionic acid, fumaric acid, malonic acid, succinic acid, maleic acid, tartaric acid, citric acid, benzoic acid and the like, sulfonic acids including methanesulfonic acid, p-toluenesulfonic acid and the like, or amino acids including glutamic acid, aspartic acid and the like. The pharmacologically acceptable metal salt includes respective alkali metal salts with lithium, sodium, potassium and the like, respective alkaline earth metal salts with magnesium, calcium and the like, and respective metal salts with aluminum, zinc and the like. The pharmacologically acceptable ammonium salt includes respective salts with ammonium, tetramethylammonium and the like. The pharmacologically acceptable organic amine salt includes respective salts with triethylamine, piperidine, morpholine, toluidine and the like. The pharmacologically acceptable amino acid addition salt includes addition salts with lysine, glycine, phenylalanine and the like.

The aminoacetonitrile compound represented by the formula (I) of the present invention may be used as a prodrug. A prodrug of the compound (I) means a compound which is converted to the compound (I) with a reaction due to an enzyme, a gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc.

Examples of the prodrug of compound (I) include
(1) a compound obtained by subjecting an amino group in compound (I) to an acylation, alkylation, or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, ethoxycarbonylation, tert-butoxycarbonylation, acetylation, cyclopropylcarbonylation, etc.);
(2) a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.);
(3) a compound obtained by subjecting a carboxyl group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.); and the like. These compounds can be produced from compound (I) by a method known per se.

A prodrug of compound (I) may be a compound which is converted to compound (I) under physiological conditions as described in Development of Pharmaceutical Products, vol. 7, Molecule Design, 163-198, Hirokawa Shoten (1990).

The aminoacetonitrile compound represented by the formula (I) of the present invention is considered to show a cell growth inhibitory activity by acting on a cyclin-dependent kinase, specifically, cyclin-dependent kinase 2 ($Cdk_2$), cyclin-dependent kinase 4 ($Cdk_4$) and the like to discontinue cell cycle, and is effective as a cell growth inhibitor.

An anticancer agent containing the aminoacetonitrile compound represented by the formula (I) or a pharmacologically acceptable salt thereof as an active ingredient can be used as a therapeutic agent for various carcinomas, for example, colon cancer (e.g., familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer), stomach cancer (e.g., papillary adenocarcinoma, mucinous adenocarcinoma, adenosquamous carcinoma), breast cancer (e.g., infiltrating duct carcinoma, ductal carcinoma in situ, inflammatory breast carcinoma), ovarian cancer (e.g., ovarian epithelial carcinoma, extragonadal germ cell tumor, ovarian germ cell tumor, ovarian low malignant potential tumor), prostate cancer (e.g., hormone-dependent prostate cancer, non-hormone dependent prostate cancer), liver cancer (e.g., primary liver cancer, extrahepatic bile duct cancer), thyroid cancer (e.g., medullary thyroid carcinoma), renal cancer (e.g., renal cell carcinoma, transitional cell cancer of the renal pelvis and ureter), uterine cancer, brain tumor (e.g., pineal astrocytoma, pilocytic astrocytoma, diffuse astrocytoma, anaplastic astrocytoma), melanoma (melanoma), sarcoma (e.g., fibrosarcoma, malignant fibrous histiocytoma, dermatofibrosarcoma, liposarcoma, rhabdomyosarcoma, Kaposi's sarcoma, synovial sarcoma etc.), urinary bladder cancer, blood cancer (e.g., multiple myeloma, leukemia, acute lymphatic leukemia, acute myeloid leukemia, chronic myeloid leukemia, B-cell lymphoma, T-cell lymphoma, Hodgkin's lymphoma, non-Hodgkin's lymphoma, hairy cell lymphoma, mantle cell lymphoma, Burkett's lymphoma), head and neck cancer, cervix cancer, esophageal cancer, gallbladder cancer, splenic cancer, testicular cancer, peripheral nerve cancer (e.g., malignant neurinoma (schwannoma), neuroblastoma, glioma), skin cancer (e.g., squamous cell carcinoma), and the like in mammals (e.g., mouse, rat, hamster, rabbit, cat, dog, bovine, sheep, monkey, human etc.), and can be particularly preferably used for the treatment of brain tumor, peripheral nerve cancer, ovarian cancer and the like.

It is also useful as a therapeutic drug for, though not limited to, sarcoma such as malignant melanoma, malignant neurinoma and the like in addition to carcinoma such as prostate cancer, metastatic lung cancer, breast adenocarcinoma and the like.

The aminoacetonitrile compound represented by the formula (I) of the present invention or a pharmacologically acceptable salt thereof is usually used in the form of a common pharmaceutical preparation (such as a method as defined in the Japanese Pharmacopoeia Twelfth Edition). The pharmaceutical preparation is prepared by using a commonly used diluent or excipient such as a bulking agent, an extender, a binding agent, a moisture-imparting agent, a disintegrator, a surfactant or a lubricant. As the pharmaceutical preparation, various forms may be selected depending upon the purpose of treatment, and a tablet, a pill, a powder, a dust, a granule, a capsule, a suppository, a solution, a suspension, an emulsion, an injection (such as a solution or a suspension), a spray, an aerosol, a cream, an ointment, a lotion or a transdermal agent (a patch, a matrix or a tape) may be mentioned as examples.

To form the medicine into a tablet, carriers which have conventionally been known in this field can be used widely, and they may, for example, be excipients such as lactose, sucrose, sodium chloride, glucose, urea, starch, calcium carbonate, kaolin, crystalline cellulose and silicic acid; binding agents such as water, ethanol, propanol, simple syrup, a glucose solution, a starch solution, a gelatin solution, carboxymethyl cellulose, Shellac, methyl cellulose, potassium phosphate and polyvinyl pyrrolidone; disintegrators such as dried starch, sodium alginate, an agar powder, a laminaran powder, sodium hydrogen carbonate, calcium carbonate, polyoxyethylene sorbitan fatty acid esters, sodium lauryl sulfate, monoglyceryl stearate, starch and lactose; disintegration inhibitors such as sucrose, stearin, cacao butter and hydrogenated oil; absorption enhancers such as a quaternary ammonium base and sodium lauryl sulfate, humectants such as glycerin and starch, adsorbents such as starch, lactose, kaolin, bentonite and colloidal silicate, and lubricants such as purified talc, a stearate, a boric acid powder and polyethylene glycol. Further, a tablet may be a tablet having a common coating applied thereto as the case requires, such as a sugar-coated tablet, a gelatin-coated tablet, an enteric-coated tablet or a film-coated tablet, or a double tablet or a multilayer tablet.

To form the medicine into a pill, carriers which have conventionally been known in this field can be used widely, and they may, for example, be excipients such as glucose, lactose, starch, cacao butter, hydrogenated vegetable oil, kaolin and talc; binding agents such as powdered acacia, powdered tragacanth, gelatin and ethanol and disintegrators such as laminaran agar.

To form the medicine into a suppository, conventionally known carriers can be used widely, and they may, for example, be polyethylene glycol, cacao butter, higher alcohols, higher alcohol esters, gelatin and semi-synthetic glyceride.

To prepare an injection, a solution, an emulsion or a suspension is sterilized, and is preferably isotonic with the blood, and to form the medicine into a solution, an emulsion or a suspension, all the diluents which are commonly used in this field can be used, and they may, for example, be water, a lactic acid aqueous solution, ethyl alcohol, propylene glycol, ethoxylated isostearyl alcohol, polyoxylated isostearyl alcohol and polyoxyethylene sorbitan fatty acid esters. In this case, sodium chloride salt, glucose or glycerin in an amount adequate to prepare an isotonic solution may be incorporated in the pharmaceutical preparation, and a common solubilizing agent, buffer, soothing agent or the like may be added thereto. Further, as the case requires, a colorant, a preservative, a fragrant material, a flavoring agent, a sweetening agent or another pharmaceutical agent may be incorporated in the pharmaceutical preparation.

The administration method of the aminoacetonitrile compound represented by the formula (I) of the present invention or a pharmacologically acceptable salt thereof is not particularly limited, and they are orally or parenterally administered by a method depending upon the form of the preparation, the age, the sex or other conditions of the patient and the degree of the disease. For example, for oral administration, a tablet, a pill, a solution, a suspension, an emulsion, a granule or a capsule may, for example, be mentioned as a preferred form. For parenteral administration, the medicine may be administered in the form of e.g. a topical agent, an injection, a transdermal agent, nasal drops, an inhalant or a suppository. In the case of an injection, it is preferred that the medicine is intravenously administered by itself or as mixed with a conventional fluid replacement such as glucose or amino acids, or as the case requires, it is intramuscularly, intracutaneously, subcutaneously or intraperitoneally administered by itself. Further, in the case of a suppository, it is preferred that the medicine is administered in rectum.

The dose of the aminoacetonitrile compound represented by the formula (I) of the present invention or a pharmacologically acceptable salt thereof is appropriately selected depending upon e.g. the direction for use, the age, the sex or other conditions of the patient and the degree of disease, etc.

While the effective amount and administration frequency of the aminoacetonitrile compound represented by the formula (I) of the present invention or a pharmacologically acceptable salt thereof vary depending on the administration form, and age, body weight, symptom and the like of the patient, 0.001 mg to 5 g, preferably 0.1 mg to 1 g, more preferably 1 to 500 mg, is generally administered to an adult per day in one to several portions.

EXAMPLES

While the present invention is more specifically explained now by way of Formulation Examples, Production Examples, Examples and the like, the technical scope of the present invention is not limited to such examples.

Formulation Example 1

1. Injection, Drip Infusion

The compound of the present invention (10 mg) is added to powder glucose (5 g), and the mixture is aseptically dispensed to a vial. The vial is tightly sealed, an inert gas such as nitrogen, helium and the like is inserted and the vial is preserved in a dark and cold place. Before use, it is dissolved in ethanol, 0.85% physiological brine (100 mL) is added to give an intravenous injection, and 10 to 100 mL/day is administered by intravenous injection or drip according to the symptoms.

Formulation Example 2

2. Granule

The compound of the present invention (1 g), lactose (98 g) and hydroxypropylcellulose (1 g) are mixed well, and formed into particles according to a conventional method. The particles are sufficiently dried and sieved, and granules suitable for a bottle, heat sealing packing and the like are produced. 100 to 1000 mg/day is orally administered according to the symptoms.

Representative Production Examples of the aminoacetonitrile compound represented by the formula (I) of the present invention are described below.

Production Example 1: Production of Compound No. 2-36

4-Chlorophenol (2.56 g), bromoacetoaldehyde dimethylacetal (3.4 g), anhydrous potassium carbonate (2.76 g) and a catalytic amount of sodium iodide were added to dimethylformamide (DMF, 20 ml), and the mixture was heated under reflux for 3 hr. After completion of the reaction, water was added to the reaction mixture, and the object product was extracted with ethyl acetate and dried over anhydrous sodium sulfate. The solvent was evaporated and the residue was purified by silica gel column chromatography (ethyl acetate-hexane) to give 4-chlorophenoxyacetoaldehyde dimethylacetal (2.37 g).

4-Chlorophenoxyacetoaldehyde dimethylacetal (1.0 g) was dissolved in acetone (10 ml), 2N hydrochloric acid (1.0 g) was added, and the mixture was heated under reflux for 8 hr. After completion of the reaction, the reaction mixture was concentrated, water was added, and the object product was extracted with ethyl acetate and dried over anhydrous sodium sulfate. The solvent was evaporated to give 4-chlorophenoxyacetoaldehyde as a crude product.

Crude 4-chlorophenoxyacetoaldehyde (0.5 g), sodium cyanide (0.17 g) and ammonium chloride (0.27 g) were added to 28% aqueous ammonia (20 ml) and the mixture was stirred for 2 days. After completion of the reaction, ethyl acetate was added to the reaction mixture, water was added for washing with water and the mixture was dried over anhydrous sodium sulfate. The solvent was evaporated and the obtained oily substance was dissolved in tetrahydrofuran (THF, 5 mL). 4-Chlorophenylacetyl chloride (0.38 g) and triethylamine (0.22 g) were added and the mixture was stirred at room temperature for 6 hr. After completion of the reaction, water was added to the reaction mixture and the object product was extracted with ethyl acetate and dried over anhydrous sodium sulfate, and the solvent was evaporated. The obtained residue was purified by silica gel column chromatography (ethyl acetate-hexane) to give the object compound (0.21 g; yield 24%; m.p. 122-127° C.).

Production Example 2

Production of Compound No. 2-19

4-Chlorophenol (10 g), chloroacetone (10.8 g), anhydrous potassium carbonate (12.9 g) and potassium iodide (1.3 g) were added to acetone (100 ml), and the mixture was heated under reflux for 6 hr. After completion of the reaction, the reaction mixture was filtered, and the filtrate was concentrated to give 4-chlorophenoxyacetone (14 g).

The obtained 4-chlorophenoxyacetone (6.0 g), sodium cyanide (1.1 g) and ammonium chloride (2.6 g) were added to 28% aqueous ammonia (20 ml), and the mixture was vigorously stirred for one day. After completion of the reaction, ethyl acetate was added to the reaction mixture, water was added for washing with water and the mixture was dried over anhydrous sodium sulfate. The solvent was evaporated to give 2-amino-2-methyl-3-(4-chlorophenoxy)propanenitrile (6.5 g). 4-Chlorophenylacetic acid (0.4 g) was added to thionyl chloride (1 mL) and the mixture was heated under reflux for 1 hr. Excess thionyl chloride was evaporated under reduced pressure. The obtained acid chloride was added to a solution (5 mL) of 2-amino-2-methyl-3-(4-chlorophenoxy)propanenitrile (0.49 g) and triethylamine (0.26 g) in THF under ice-cooling, and the mixture was stirred at room temperature for 3 hr. After completion of the reaction, water was added to the reaction mixture and the object product was extracted with ethyl acetate, and dried over anhydrous sodium sulfate. The solvent was evaporated and the obtained solid residue was washed with hexane-ether to give the object compound (0.56 g; yield 66%; m.p. 152° C.)

An experiment was performed according to the method described in Ahmed S A et al., 1994. Journal of Immunological Methods 170: 211-224, or Boyed M R et al., 1989.

Example 1: OVCAR-3 Cell Growth Inhibitory Activity Test

A cell suspension of human oophoroma cell line (OVCAR-3) prepared to $2.5 \times 10^3$/well was added to a well microplate, a given amount of a test substance (30 µM) or a control solvent was added to the culture medium, and the mixture was cultured for 72 hr. Thereafter, 9% Alamaer Blue was added to each well, and the mixture was further cultured for 6 hr. Then, the absorbance at 530 nm (reference wavelength 590 nm) was measured by a microplate reader and the cell growth inhibition ratio was calculated from the following formula.

inhibition ratio (%)={1−(absorbance of test substance/absorbance of control solvent)}×100

Example 2: SK-N-MC Cell Growth Inhibitory Activity Test

A test was performed in the same manner as in Example 1 except that the cell number of human neuroepithelioma cell line (SK-N-MC) at the start of preculture was changed to $5 \times 10^3$/well.

Example 3: U-87 Cell Growth Inhibitory Activity Test

A test was performed in the same manner as in Example 1 except that the cell number of human brain glioblastoma cell line (U-87) at the start of preculture was changed to $1.5 \times 10^3$/well.

As a result, the compounds Nos. 1-4, 1-5, 1-6, 1-9, 1-10, 1-17, 1-18, 1-23, 1-25, 1-41, 1-42, 1-50, 1-55, 1-56, 1-93, 1-94, 2-3, 2-26, 2-27, 2-36, 2-37, 2-51, 2-54, 2-60, 2-63, 2-66, 2-72, 2-73, 2-75, 2-76, 2-84, 2-94, 2-98, 2-101, 2-102, 2-103, 2-104, 2-105, 2-106, 2-109, 2-110, 2-112, 2-113, 2-114, 2-115, 2-116, 2-120, 2-128, 2-129, 2-130, 2-132, 2-135, 2-136, 2-137, 2-138, 2-139, 2-141, 2-142, 2-143, 2-145, 2-146, 4-1, 5-7, 5-21, 5-28, 5-31, 5-33, 5-42, 5-48, 5-52, 5-53, 5-54, 5-55, 5-58, 5-60, 5-61, 5-74, 5-75, 5-76, 5-130, 5-131, 5-140, 5-141, 5-144, 5-145, 5-146, 5-148, 5-149, 5-150, 5-157, 5-158, 5-159, 5-160, 6-12, 6-15, 6-16, 6-19, 6-24, 6-27, 6-28, 6-30, 6-50, 6-76, 6-77, 6-79, 6-81, 6-82, 6-87, 6-107, and 6-108 showed a cell growth inhibitory effect of not less than 50% at 30 µM against OVCAR-3.

The compounds Nos. 1-4, 1-5, 1-6, 1-9, 1-10, 1-18, 1-25, 1-29, 1-33, 1-39, 1-40, 1-41, 1-42, 1-47, 1-50, 1-51, 1-54, 1-55, 1-56, 1-67, 1-69, 1-73, 1-74, 1-76, 1-87, 1-90, 1-93, 1-94, 1-95, 2-36, 2-37, 2-51, 2-54, 2-60, 2-63, 2-66, 2-72, 2-73, 2-76, 2-84, 2-87, 2-94, 2-98, 2-103, 2-109, 2-110, 2-112, 2-113, 2-114, 2-115, 2-116, 2-120, 2-129, 2-130, 2-132, 2-135, 2-136, 2-137, 2-138, 2-139, 2-141, 2-142, 2-143, 2-144, 2-145, 2-146, 4-1, 5-8, 5-9, 5-21, 5-28, 5-31, 5-45, 5-51, 5-52, 5-53, 5-54, 5-55, 5-56, 5-57, 5-59, 5-60, 5-61, 5-62, 5-63, 5-64, 5-65, 5-66, 5-67, 5-69, 5-71, 5-74, 5-75, 5-77, 5-78, 5-90, 5-130, 5-131, 5-141, 5-143, 5-144, 5-146, 5-147, 5-149, 5-150, 5-156, 5-158, 5-159, 5-160, 6-12, 6-13, 6-14, 6-16, 6-18, 6-27, 6-29, 6-30, 6-77, 6-79, 6-82, 6-87, 6-94, 6-99, 6-106, 6-107, and 6-108 showed a cell growth inhibitory effect of not less than 50% at 30 µM against SK-N-MC.

The compounds Nos. 1-5, 1-6, 1-25, 1-41, 1-42, 1-74, 1-76, 1-93, 1-94, 2-54, 2-76, 2-84, 2-109, 2-110, 2-112, 2-113, 2-114, 2-116, 2-120, 2-136, 2-137, 2-143, 2-145, 2-146, 4-1, 5-18, 5-19, 5-21, 5-33, 5-45, 5-63, 5-66, 5-69, 5-75, 5-81, 5-115, 5-136, 5-147, 5-152, 5-153, 5-156, 5-158, 5-159, 5-160, 6-12, 6-14, 6-24, 6-27, 6-29, 6-30, 6-66, 6-87, 6-99, 6-114, and 6-116 showed a cell growth inhibitory effect of not less than 50% at 30 µM against U-87.

Example 4: Test for Cell Growth Inhibitory Activity Against A2780 (Epithelial Ovarian Cancer)

A cell suspension of oophoroma cell line (A2780) prepared to 2 to $3 \times 10^3$/well was added to a well microplate, a given amount of a test substance (0, 1.25, 2.5, 5, 10, 12.5, 20, 25, 50, 100 µM) was added to the culture medium, and the mixture was cultured for 72 hr. Thereafter, 0.4% sulforhodamine B was added to each well, and the absorbance at 570 nm was measured by a microplate reader. The cell growth inhibition ratio was calculated from the above-mentioned formula, and IC$_{50}$ value was determined from the data. The same test was performed using HOSE cell (normal ovary cell line) as a comparison target instead of A2780 cell, and IC$_{50}$ value was determined. The results are shown in Table 7.

TABLE 7

| Compound No. | IC$_{50}$ (μM) | |
|---|---|---|
| | A2780 | HOSE |
| 1-10 | 10.28 | 49.42 |
| 1-25 | 4.53 | 15.28 |
| 1-29 | 13.35 | — |
| 1-39 | 6.97 | — |
| 1-56 | 11.4 | — |
| 2-27 | 8.814 | 15.83 |
| 2-109 | 3.765 | — |
| 2-114 | 3.533 | 19.93 |
| 2-120 | 6.2 | 10.37 |
| 4-1 | 7.22 | — |

From the above results, it was clarified that the aminoacetonitrile compound of the present invention shows a superior anticancer activity, and mild toxicity for normal cells.

INDUSTRIAL APPLICABILITY

The aminoacetonitrile compound of the present invention or a pharmacologically acceptable salt thereof is useful as a cell growth inhibitor or anticancer agent.

This application is based on Japanese patent application No. 2013-190509 (Filing Date: Sep. 13, 2013), and the contents of which are encompassed in full herein.

The invention claimed is:

1. An anticancer agent comprising, as an active ingredient, an aminoacetonitrile compound represented by the formula (I)

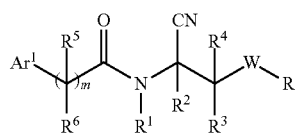

wherein
R$^1$ is
(a1) a hydrogen atom,
(a2) a (C$_1$-C$_6$)alkyl group,
(a3) a (C$_2$-C$_6$)alkenyl group,
(a4) a (C$_2$-C$_6$)alkynyl group, or
(a5) a (C$_3$-C$_6$)cycloalkyl group;
R$^2$, R$^3$, and R$^4$ are the same or different and each is
(b1) a hydrogen atom,
(b2) a (C$_1$-C$_6$)alkyl group, or
(b3) a (C$_3$-C$_6$)cycloalkyl group, or
(b4) R$^2$ and R$^3$ are optionally bonded to form a (C$_1$-C$_6$) alkylene group wherein the (C$_1$-C$_6$)alkylene group optionally has the same or different one or more substituents selected from a halogen atom, a (C$_1$-C$_6$)alkyl group, and a (C$_1$-C$_6$)alkoxy group on the chain;
R$^5$ and R$^6$ are the same or different and each is
(c1) a hydrogen atom,
(c2) a halogen atom,
(c3) a (C$_1$-C$_6$)alkyl group,
(c4) a (C$_3$-C$_6$)cycloalkyl group, or
(c5) a (C$_1$-C$_6$)alkoxy group, or
(c6) R$^5$ and R$^6$ are optionally bonded to form a (C$_1$-C$_6$) alkylene group;
m is 0 or 1;
R is
(d1) a phenyl group,
(d2) a phenyl group having, on the ring, the same or different 1 to 5 substituents selected from
(a) a halogen atom,
(b) a cyano group,
(c) a nitro group,
(d) a (C$_1$-C$_6$)alkyl group,
(e) a halo(C$_1$-C$_6$)alkyl group,
(f) a (C$_2$-C$_6$)alkenyl group,
(g) a (C$_2$-C$_6$)alkynyl group,
(h) a (C$_1$-C$_6$)alkoxy group,
(i) a halo(C$_1$-C$_6$)alkoxy group,
(j) a halo(C$_2$-C$_6$)alkenyloxy group,
(k) a halo(C$_2$-C$_6$)alkynyloxy group,
(l) a (C$_1$-C$_6$)alkylthio group,
(l1) a (C$_1$-C$_6$)alkylsulfinyl group,
(m) a (C$_1$-C$_6$)alkylsulfonyl group,
(n) a halo(C$_1$-C$_6$)alkylthio group,
(n1) a halo(C$_1$-C$_6$)alkylsulfinyl group,
(n2) a halo(C$_1$-C$_6$)alkylsulfonyl group,
(o) a phenyl(C$_2$-C$_6$)alkynyl group,
(o1) a phenyl group,
(o2) a phenyl group having, on the ring, the same or different 1 to 5 substituents selected from
(i) a halogen atom,
(ii) a cyano group,
(iii) a nitro group,
(iv) a (C$_1$-C$_6$)alkyl group, and
(v) a halo(C$_1$-C$_6$)alkyl group;
(p) a phenoxy group,
(q) a pyridyloxy group having, on the ring, the same or different 1 to 4 substituents selected from
(i) a halogen atom, and
(ii) a halo(C$_1$-C$_6$)alkyl group;
(r) a pyridyl(C$_2$-C$_6$)alkynyl group,
(s) a (C$_1$-C$_6$)alkylcarbonyl group,
(t) a (C$_1$-C$_6$)alkoxycarbonyl group,
(u) an aminocarbonyl group,
(v) a (C$_1$-C$_6$)alkylcarbonylamino group,
(w) a (C$_1$-C$_6$)alkoxycarbonylamino group,
(x) a di(C$_1$-C$_6$)alkylamino group (the alkyl groups are the same or different), and
(y) a (C$_1$-C$_6$)alkylaminocarbonylamino group,
(d3) a naphthyl group,
(d4) a naphthyl group having, on the ring, the same or different 1 to 7 substituents selected from
(a) a halogen atom,
(b) a cyano group,
(c) a nitro group,
(d) a (C$_1$-C$_6$)alkyl group, and
(e) a halo(C$_1$-C$_6$)alkyl group,
(d5) a (C$_1$-C$_{12}$)alkyl group,
(d6) a pyridyl group,
(d7) a pyridyl group having, on the ring, the same or different 1 to 4 substituents selected from
(a) a halogen atom,
(b) a cyano group,
(c) a nitro group,
(d) a (C$_1$-C$_6$)alkyl group, and
(e) a halo(C$_1$-C$_6$)alkyl group, (d8) a pyrazinyl group,
(d9) a pyrazinyl group having, on the ring, the same or different 1 to 3 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group,
(d10) a thiazolyl group,
(d11) a thiazolyl group having, on the ring, the same or different 1 to 2 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group,
(d12) a pyrazolyl group, or
(d13) a pyrazolyl group having, on the ring, the same or different 1 to 3 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group;
$Ar^1$ is
(e1) a phenyl group,
(e2) a phenyl group having, on the ring, the same or different 1 to 5 substituents selected from
  (a) a halogen atom,
  (b) a cyano group,
  (c) a nitro group,
  (d) a $(C_1\text{-}C_6)$alkyl group,
  (e) a halo$(C_1\text{-}C_6)$alkyl group,
  (f) a $(C_2\text{-}C_6)$alkenyl group,
  (g) a $(C_2\text{-}C_6)$alkynyl group,
  (h) a $(C_1\text{-}C_6)$alkoxy group,
  (i) a halo$(C_1\text{-}C_6)$alkoxy group,
  (j) a halo$(C_2\text{-}C_6)$alkenyloxy group,
  (k) a halo$(C_2\text{-}C_6)$alkynyloxy group,
  (l) a $(C_1\text{-}C_6)$alkylthio group,
  (m) a $(C_1\text{-}C_6)$alkylsulfonyl group that is optionally substituted by one or more halogen atoms,
  (n) a halo$(C_1\text{-}C_6)$alkylthio group,
  (o) a phenyl$(C_2\text{-}C_6)$alkynyl group,
  (p) a phenoxy group,
  (q) a pyridyloxy group having, on the ring, the same or different 1 to 4 substituents selected from
    (i) a halogen atom, and
    (ii) a halo$(C_1\text{-}C_6)$alkyl group,
  (r) a hydroxyl group,
  (s) a phenyl group, and
  (t) a halo$(C_1\text{-}C_6)$alkylsulfonylamino group,
(e3) a naphthyl group,
(e4) a naphthyl group having, on the ring, the same or different 1 to 7 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group,
(e5) a pyridyl group,
(e6) a pyridyl group having, on the ring, the same or different 1 to 4 substituents selected from
  (a) a halogen atom,
  (b) a $(C_1\text{-}C_6)$alkyl group,
  (c) a halo$(C_1\text{-}C_6)$alkyl group,
  (d) a $(C_1\text{-}C_6)$alkylthio group,
  (e) a $(C_1\text{-}C_6)$alkylsulfonyl group,
  (f) a halo$(C_1\text{-}C_6)$alkylthio group, and
  (g) a $(C_1\text{-}C_6)$alkoxy group,
(e7) a pyrazolyl group, or
(e8) a pyrazolyl group having, on the ring, the same or different 1 to 3 substituents selected from
  (a) a halogen atom,
  (b) a $(C_1\text{-}C_6)$alkyl group,
  (c) a halo$(C_1\text{-}C_6)$alkyl group,
  (d) a $(C_1\text{-}C_6)$alkylthio group,
  (e) a $(C_1\text{-}C_6)$alkylsulfonyl group,
  (f) a $(C_1\text{-}C_6)$alkoxycarbonyl group,
  (g) a $(C_1\text{-}C_6)$alkoxy group,
  (h) a halo$(C_1\text{-}C_6)$alkoxy group,
  (i) a $(C_1\text{-}C_6)$alkoxy$(C_1\text{-}C_6)$alkoxy group,
  (j) a cyclo$(C_3\text{-}C_6)$alkyl group,
  (k) a phenoxy group, and
  (l) a phenyl group, or
(e9) a heterocyclic group selected from following Q-1 to Q-17,

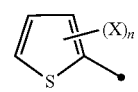

Q-1

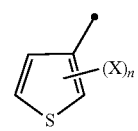

Q-2

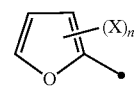

Q-3

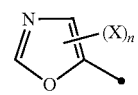

Q-4

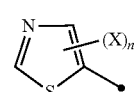

Q-5

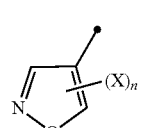

Q-6

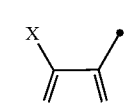

Q-7

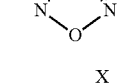

Q-8

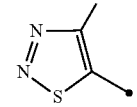

Q-9

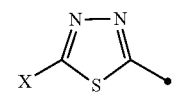

-continued

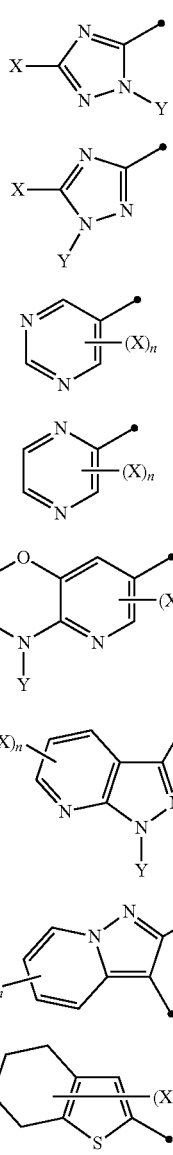

wherein X and Y are the same or different and each is
(a) a halogen atom,
(b) a cyano group,
(c) a nitro group,
(d) a $(C_1-C_6)$alkyl group,
(e) a cyclo$(C_3-C_6)$alkyl group,
(f) a halo$(C_1-C_6)$alkyl group,
(g) a $(C_1-C_6)$alkoxy group,
(h) a halo$(C_1-C_6)$alkoxy group,
(i) a $(C_1-C_6)$alkylthio group,
(j) a phenyl group,
(n) a phenyl group having, on the ring, the same or different 1 to 4 substituents selected from
  (i) a halogen atom,
  (ii) a $(C_1-C_6)$alkyl group,
  (iii) a halo$(C_1-C_6)$alkyl group, and
  (iv) a $(C_1-C_6)$alkoxy group,
(m) a pyridyl group,
(o) a $(C_1-C_6)$alkylcarbonyl group,
(p) a $(C_1-C_6)$alkoxycarbonyl group,
(q) a mono$(C_1-C_6)$alkylamino group,
(r) a $(C_1-C_6)$alkoxy$(C_1-C_6)$alkylamino group,
(s) a di$(C_1-C_6)$alkylamino group (the alkyl groups are the same or different),
(t) a $(C_1-C_6)$alkoxycarbonylamino group,
(u) a monophenylamino group,
(v) a morpholino group, or
(w) a piperidino group,
• is a binding position,
n is an integer of 0 to 3; and
W is —O—, —S—, —SO$_2$—, or —N(R$^7$)— wherein R$^7$ is a hydrogen atom, a $(C_1-C_6)$alkyl group or a $(C_3-C_6)$cycloalkyl group; and
wherein
(i) Ar$^1$ is a phenyl group substituted with a single substituent selected from halo$(C_1-C_6)$alkylthio and halo$(C_1-C_6)$alkylsulfonyl, except that when AO is a phenyl group substituted with a single halo$(C_1-C_6)$alkylthio group, R is not a phenyl group substituted with one or more (d2)(a) or (d2)(e) groups; or
(ii) R is a phenyl group substituted with a single substituent selected from halo$(C_1-C_6)$alkylthio, halo$(C_1-C_6)$alkylsulfinyl group, and halo$(C_1-C_6)$alkylsulfonyl group;
(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide,
N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide,
N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide,
N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide),
or a pharmacologically acceptable salt thereof.

2. An anticancer agent comprising, as an active ingredient, an aminoacetonitrile compound represented by the formula (I)

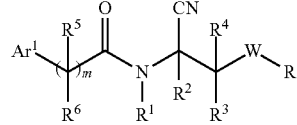

wherein
R$^1$ is
(a1) a hydrogen atom,
(a2) a $(C_1-C_6)$alkyl group,
(a3) a $(C_2-C_6)$alkenyl group,
(a4) a $(C_2-C_6)$alkynyl group, or
(a5) a $(C_3-C_6)$cycloalkyl group;

$R^2$, $R^3$, and $R^4$ are the same or different and each is
(b1) a hydrogen atom,
(b2) a $(C_1\text{-}C_6)$alkyl group, or
(b3) a $(C_3\text{-}C_6)$cycloalkyl group, or
(b4) $R^2$ and $R^3$ are optionally bonded to form a $(C_1\text{-}C_6)$ alkylene group wherein the $(C_1\text{-}C_6)$alkylene group optionally has the same or different one or more substituents selected from a halogen atom, a $(C_1\text{-}C_6)$alkyl group, and a $(C_1\text{-}C_6)$alkoxy group on the chain;
$R^5$ and $R^6$ are the same or different and each is
(c1) a hydrogen atom,
(c2) a halogen atom,
(c3) a $(C_1\text{-}C_6)$alkyl group, or
(c4) a $(C_3\text{-}C_6)$cycloalkyl group, or
(c6) $R^5$ and $R^6$ are optionally bonded to form a $(C_1\text{-}C_6)$ alkylene group;
m is 0 or 1;
R is
(d1) a phenyl group,
(d2) a phenyl group having, on the ring, the same or different 1 to 5 substituents selected from
  (a) a halogen atom,
  (b) a cyano group,
  (c) a nitro group,
  (d) a $(C_1\text{-}C_6)$alkyl group,
  (e) a halo$(C_1\text{-}C_6)$alkyl group,
  (f) a $(C_2\text{-}C_6)$alkenyl group,
  (g) a $(C_2\text{-}C_6)$alkynyl group,
  (h) a $(C_1\text{-}C_6)$alkoxy group,
  (i) a halo$(C_1\text{-}C_6)$alkoxy group,
  (j) a halo$(C_2\text{-}C_6)$alkenyloxy group,
  (k) a halo$(C_2\text{-}C_6)$alkynyloxy group,
  (l) a $(C_1\text{-}C_6)$alkylthio group,
  (m) a $(C_1\text{-}C_6)$alkylsulfonyl group,
  (n) a halo$(C_1\text{-}C_6)$alkylthio group,
  (o) a phenyl$(C_2\text{-}C_6)$alkynyl group,
  (p) a phenoxy group, and
  (q) a pyridyloxy group having, on the ring, the same or different 1 to 4 substituents selected from
    (i) a halogen atom, and
    (ii) a halo$(C_1\text{-}C_6)$alkyl group;
(d3) a naphthyl group,
(d4) a naphthyl group having, on the ring, the same or different 1 to 7 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group, or
(d5) a $(C_1\text{-}C_{12})$alkyl group;
$Ar^1$ is
(e1) a phenyl group,
(e2) a phenyl group having, on the ring, the same or different 1 to 5 substituents selected from
  (a) a halogen atom,
  (b) a cyano group,
  (c) a nitro group,
  (d) a $(C_1\text{-}C_6)$alkyl group,
  (e) a halo$(C_1\text{-}C_6)$alkyl group,
  (f) a $(C_2\text{-}C_6)$alkenyl group,
  (g) a $(C_2\text{-}C_6)$alkynyl group,
  (h) a $(C_1\text{-}C_6)$alkoxy group,
  (i) a halo$(C_1\text{-}C_6)$alkoxy group,
  (j) a halo$(C_2\text{-}C_6)$alkenyloxy group,
  (k) a halo$(C_2\text{-}C_6)$alkynyloxy group,
  (l) a $(C_1\text{-}C_6)$alkylthio group,
  (m) a $(C_1\text{-}C_6)$alkylsulfonyl group that is optionally substituted by one or more halogen atoms,
  (n) a halo$(C_1\text{-}C_6)$alkylthio group,
  (o) a phenyl$(C_2\text{-}C_6)$alkynyl group,
  (p) a phenoxy group,
  (q) a pyridyloxy group having, on the ring, the same or different 1 to 4 substituents selected from
    (i) a halogen atom, and
    (ii) a halo$(C_1\text{-}C_6)$alkyl group,
  (r) a hydroxyl group,
  (s) a phenyl group, and
  (t) a halo$(C_1\text{-}C_6)$alkylsulfonylamino group,
(e3) a naphthyl group,
(e4) a naphthyl group having, on the ring, the same or different 1 to 7 substituents selected from
  (a) a halogen atom,
  (b) a cyano group,
  (c) a nitro group,
  (d) a $(C_1\text{-}C_6)$alkyl group, and
  (e) a halo$(C_1\text{-}C_6)$alkyl group,
(e5) a pyridyl group,
(e6) a pyridyl group having, on the ring, the same or different 1 to 4 substituents selected from
  (a) a halogen atom,
  (b) a $(C_1\text{-}C_6)$alkyl group,
  (c) a halo$(C_1\text{-}C_6)$alkyl group,
  (d) a $(C_1\text{-}C_6)$alkylthio group,
  (e) a $(C_1\text{-}C_6)$alkylsulfonyl group, and
  (f) a halo$(C_1\text{-}C_6)$alkylthio group,
(e7) a pyrazolyl group, or
(e8) a pyrazolyl group having, on the ring, the same or different 1 to 3 substituents selected from
  (a) a halogen atom,
  (b) a $(C_1\text{-}C_6)$alkyl group,
  (c) a halo$(C_1\text{-}C_6)$alkyl group,
  (d) a $(C_1\text{-}C_6)$alkylthio group,
  (e) a $(C_1\text{-}C_6)$alkylsulfonyl group, and
  (f) a $(C_1\text{-}C_6)$alkoxycarbonyl group; and
W is —O—, —S—, —$SO_2$—, or —$N(R^7)$— wherein $R^7$ is a hydrogen atom, a $(C_1\text{-}C_6)$alkyl group or a $(C_3\text{-}C_6)$ cycloalkyl group; and
wherein
(i) $Ar^1$ is a phenyl group substituted with a single substituent selected from halo$(C_1\text{-}C_6)$alkylthio and halo $(C_1\text{-}C_6)$alkylsulfonyl, except that when AO is a phenyl group substituted with a single halo$(C_1\text{-}C_6)$alkylthio group, R is not a phenyl group substituted with one or more (d2)(a) or (d2)(e) groups; or
(ii) R is a phenyl group substituted with a single substituent selected from halo$(C_1\text{-}C_6)$alkylthio, halo$(C_1\text{-}C_6)$ alkylsulfinyl group, and halo$(C_1\text{-}C_6)$alkylsulfonyl group;
(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide,
N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide,
N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide, N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide),
or a pharmacologically acceptable salt thereof.

3. The anticancer agent according to claim 1, wherein $R^1$ is
(a1) a hydrogen atom,
(a2) a $(C_1$-$C_6)$alkyl group, or
(a4) a $(C_2$-$C_6)$alkynyl group;
$R^2$, $R^3$, and $R^4$ are the same or different and each is
(b1) a hydrogen atom;
(b2) a $(C_1$-$C_6)$alkyl group, or
(b3) a $(C_3$-$C_6)$cycloalkyl group, or
(b4) $R^2$ and $R^3$ are optionally bonded to form a $(C_1$-$C_6)$ alkylene group wherein the $(C_1$-$C_6)$alkylene group optionally has the same or different one or more substituents selected from a halogen atom, a $(C_1$-$C_6)$alkyl group, and a $(C_1$-$C_6)$alkoxy group on the chain;
$R^5$ and $R^6$ are the same or different and each is
(c1) a hydrogen atom,
(c2) a halogen atom, or
(c5) a $(C_1$-$C_6)$alkoxy group, or
(c6) $R^5$ and $R^6$ are optionally bonded to form a $(C_1$-$C_6)$ alkylene group;
R is
(d1) a phenyl group,
(d2) a phenyl group having, on the ring, the same or different 1 to 5 substituents selected from
  (a) a halogen atom,
  (b) a cyano group,
  (c) a nitro group,
  (d) a $(C_1$-$C_6)$alkyl group,
  (e) a halo$(C_1$-$C_6)$alkyl group,
  (g) a $(C_2$-$C_6)$alkynyl group,
  (h) a $(C_1$-$C_6)$alkoxy group,
  (i) a halo$(C_1$-$C_6)$alkoxy group,
  (j) a halo$(C_2$-$C_6)$alkenyloxy group,
  (l) a $(C_1$-$C_6)$alkylthio group,
  (l1) a $(C_1$-$C_6)$alkylsulfinyl group,
  (m) a $(C_1$-$C_6)$alkylsulfonyl group,
  (n) a halo$(C_1$-$C_6)$alkylthio group,
  (n1) a halo$(C_1$-$C_6)$alkylsulfinyl group,
  (n2) a halo$(C_1$-$C_6)$alkylsulfonyl group,
  (o) a phenyl$(C_2$-$C_6)$alkynyl group,
  (o1) a phenyl group,
  (o2) a phenyl group having, on the ring, the same or different 1 to 5 substituents selected from
    (i) a halogen atom,
    (ii) a cyano group,
    (iii) a nitro group,
    (iv) a $(C_1$-$C_6)$alkyl group, and
    (v) a halo$(C_1$-$C_6)$alkyl group,
  (p) a phenoxy group,
  (q) a pyridyloxy group having, on the ring, the same or different 1 to 4 substituents selected from
    (i) a halogen atom, and
    (ii) a halo$(C_1$-$C_6)$alkyl group,
  (r) a pyridyl$(C_2$-$C_6)$alkynyl group,
  (s) a $(C_1$-$C_6)$alkylcarbonyl group,
  (t) a $(C_1$-$C_6)$alkoxycarbonyl group,
  (u) an aminocarbonyl group,
  (v) a $(C_1$-$C_6)$alkylcarbonylamino group,
  (w) a $(C_1$-$C_6)$alkoxycarbonylamino group,
  (x) a di$(C_1$-$C_6)$alkylamino group (the alkyl groups are the same or different), and
  (y) a $(C_1$-$C_6)$alkylaminocarbonylamino group,
(d3) a naphthyl group,
(d6) a pyridyl group,
(d7) a pyridyl group having, on the ring, the same or different 1 to 4 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group;
(d9) a pyrazinyl group having, on the ring, the same or different 1 to 3 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group,
(d11) a thiazolyl group having, on the ring, the same or different 1 to 2 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group, or
(d13) a pyrazolyl group having, on the ring, the same or different 1 to 3 substituents selected from
  (a) a halogen atom,
  (b) a cyano group,
  (c) a nitro group,
  (d) a $(C_1$-$C_6)$alkyl group, and
  (e) a halo$(C_1$-$C_6)$alkyl group;
$Ar^1$ is
(e1) a phenyl group,
(e2) a phenyl group having, on the ring, the same or different 1 to 5 substituents selected from
  (a) a halogen atom,
  (b) a cyano group,
  (c) a nitro group,
  (d) a $(C_1$-$C_6)$alkyl group,
  (e) a halo$(C_1$-$C_6)$alkyl group,
  (f) a $(C_2$-$C_6)$alkenyl group,
  (g) a $(C_2$-$C_6)$alkynyl group,
  (h) a $(C_1$-$C_6)$alkoxy group,
  (i) a halo$(C_1$-$C_6)$alkoxy group,
  (j) a halo$(C_2$-$C_6)$alkenyloxy group,
  (k) a halo$(C_2$-$C_6)$alkynyloxy group,
  (l) a $(C_1$-$C_6)$alkylthio group,
  (m) a $(C_1$-$C_6)$alkylsulfonyl group that is optionally substituted by one or more halogen atoms,
  (n) a halo$(C_1$-$C_6)$alkylthio group,
  (o) a phenyl$(C_2$-$C_6)$alkynyl group,
  (p) a phenoxy group,
  (q) a pyridyloxy group having, on the ring, the same or different 1 to 4 substituents selected from
    (i) a halogen atom, and
    (ii) a halo$(C_1$-$C_6)$alkyl group,
  (r) a hydroxyl group,
  (s) a phenyl group, and
  (t) a halo$(C_1$-$C_6)$alkylsulfonylamino group,
(e3) a naphthyl group,
(e5) a pyridyl group,
(e6) a pyridyl group having, on the ring, the same or different 1 to 4 substituents selected from (a) a halogen atom,
(b) a $(C_1-C_6)$alkyl group,
(c) a halo$(C_1-C_6)$alkyl group,
(d) a $(C_1-C_6)$alkylthio group,
(e) a $(C_1-C_6)$alkylsulfonyl group,
(f) a halo$(C_1-C_6)$alkylthio group, and
(g) a $(C_1-C_6)$alkoxy group,
(e8) a pyrazolyl group having, on the ring, the same or different 1 to 3 substituents selected from
(a) a halogen atom,
(b) a $(C_1-C_6)$alkyl group,
(c) a halo$(C_1-C_6)$alkyl group,
(d) a $(C_1-C_6)$alkylthio group,
(e) a $(C_1-C_6)$alkylsulfonyl group,
(f) a $(C_1-C_6)$alkoxycarbonyl group
(g) a $(C_1-C_6)$alkoxy group,
(h) a halo$(C_1-C_6)$alkoxy group,
(i) a $(C_1-C_6)$alkoxy$(C_1-C_6)$alkoxy group,
(j) a cyclo$(C_3-C_6)$alkyl group,
(k) a phenoxy group, and
(l) a phenyl group, or
(e9) a heterocyclic group selected from following Q-1 to Q-17,

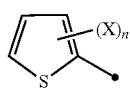
Q-1

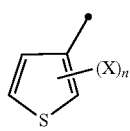
Q-2

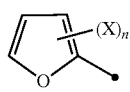
Q-3

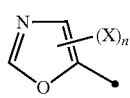
Q-4

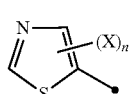
Q-5

Q-6

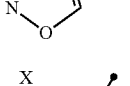
Q-7

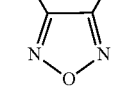
Q-8

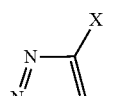
Q-9

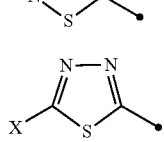

-continued

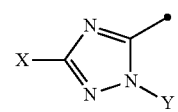
Q-10

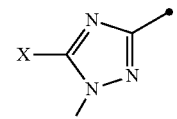
Q-11

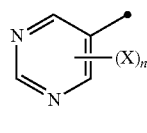
Q-12

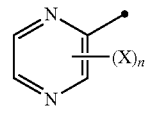
Q-13

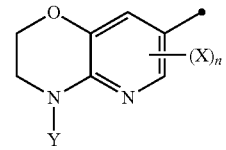
Q-14

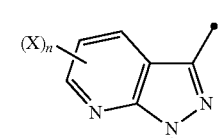
Q-15

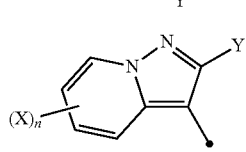
Q-16

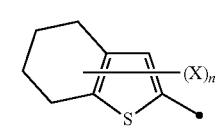
Q-17 wherein X and Y are the same or different and each is
(a) a halogen atom,
(b) a cyano group,
(c) a nitro group,
(d) a $(C_1-C_6)$alkyl group,
(e) a cyclo$(C_3-C_6)$alkyl group,
(f) a halo$(C_1-C_6)$alkyl group,
(g) a $(C_1-C_6)$alkoxy group,
(h) a halo$(C_1-C_6)$alkoxy group,
(i) a $(C_1-C_6)$alkylthio group,
(j) a phenyl group,
(n) a phenyl group having, on the ring, the same or different 1 to 4 substituents selected from
    (i) a halogen atom,
    (ii) a $(C_1-C_6)$alkyl group,
    (iii) a halo$(C_1-C_6)$alkyl group, and
    (iv) a $(C_1-C_6)$alkoxy group,
(m) a pyridyl group,
(o) a $(C_1-C_6)$alkylcarbonyl group,
(p) a $(C_1-C_6)$alkoxycarbonyl group,
(q) a mono$(C_1-C_6)$alkylamino group, (r) a $(C_1-C_6)$alkoxy$(C_1-C_6)$alkylamino group,
(s) a di$(C_1-C_6)$alkylamino group (the alkyl groups are the same or different),
(t) a $(C_1-C_6)$alkoxycarbonylamino group,
(u) a monophenylamino group,
(v) a morpholino group, or
(w) a piperidino group,
• is a binding position,
n is an integer of 0 to 3;
W is —O—, —S—, —SO2-, or —N($R^7$)—, wherein $R^7$ is a $(C_1-C_6)$alkyl group.

4. The anticancer agent according to claim 1, wherein m is 1.

5. The anticancer agent according to claim 1, wherein when m is 0, then $AR^1$ is
(e2) a phenyl group having, on the ring, the same or different 1 to 5 substituents selected from
  (c) a nitro group,
  (e') a halo$(C_2-C_6)$alkyl group,
  (f) a $(C_2-C_6)$alkenyl group,
  (g) a $(C_2-C_6)$alkynyl group,
  (i') a halo$(C_2-C_6)$alkoxy group,
  (j) a halo$(C_2-C_6)$alkenyloxy group,
  (k) a halo$(C_2-C_6)$alkynyloxy group,
  (l) a $(C_1-C_6)$alkylthio group,
  (m) a $(C_1-C_6)$alkylsulfonyl group,
  (n') a halo$(C_2-C_6)$alkylthio group,
  (o) a phenyl$(C_2-C_6)$alkynyl group,
  (p) a phenoxy group,
  (q) a pyridyloxy group having, on the ring, the same or different 1 to 4 substituents selected from
    (i) a halogen atom, and
    (ii) a halo$(C_1-C_6)$alkyl group,
  (r) a hydroxyl group,
  (s) a phenyl group, and
  (t) a halo$(C_1-C_6)$alkylsulfonylamino group,
(e3) a naphthyl group,
(e4) a naphthyl group having, on the ring, the same or different 1 to 7 substituents selected from
  (a) a halogen atom,
  (b) a cyano group,
  (c) a nitro group,
  (d) a $(C_1-C_6)$alkyl group, and
  (e) a halo$(C_1-C_6)$alkyl group,
(e5) a pyridyl group,
(e6) a pyridyl group having, on the ring, the same or different 1 to 4 substituents selected from
  (a) a halogen atom,
  (b) a $(C_1-C_6)$alkyl group,
  (c) a halo$(C_1-C_6)$alkyl group,
  (d) a $(C_1-C_6)$alkylthio group,
  (e) a $(C_1-C_6)$alkylsulfonyl group, and
  (f) a halo$(C_1-C_6)$alkylthio group,
(e7) a pyrazolyl group, or
(e8) a pyrazolyl group having, on the ring, the same or different 1 to 3 substituents selected from
  (a) a halogen atom,
  (b) a $(C_1-C_6)$alkyl group,
  (c) a halo$(C_1-C_6)$alkyl group,
  (d) a $(C_1-C_6)$alkylthio group,
  (e) a $(C_1-C_6)$alkylsulfonyl group, and
  (f) a $(C_1-C_6)$alkoxycarbonyl group.

6. The anticancer agent according to claim 1, wherein when m is 0, then R is
(d2) a phenyl group having, on the ring, the same or different 1 to 5 substituents selected from
  (c) a nitro group,
  (e') a halo$(C_2-C_6)$alkyl group,
  (f) a $(C_2-C_6)$alkenyl group,
  (g) a $(C_2-C_6)$alkynyl group,
  (h) a $(C_1-C_6)$alkoxy group,
  (i) a halo$(C_1-C_6)$alkoxy group,
  (j) a halo$(C_2-C_6)$alkenyloxy group,
  (k) a halo$(C_2-C_6)$alkynyloxy group,
  (l) a $(C_1-C_6)$alkylthio group,
  (m) a $(C_1-C_6)$alkylsulfonyl group,
  (n) a halo$(C_1-C_6)$alkylthio group,
  (o) a phenyl$(C_2-C_6)$alkynyl group,
  (p) a phenoxy group, and
  (q) a pyridyloxy group having, on the ring, the same or different 1 to 4 substituents selected from
    (i) a halogen atom, and
    (ii) a halo$(C_1-C_6)$alkyl group,
(d3) a naphthyl group,
(d4) a naphthyl group having, on the ring, the same or different 1 to 7 substituents selected from
  (a) a halogen atom,
  (b) a cyano group,
  (c) a nitro group,
  (d) a $(C_1-C_6)$alkyl group, and
  (e) a halo$(C_1-C_6)$alkyl group, or
(d5) a $(C_1-C_{12})$alkyl group.

7. The anticancer agent according to claim 1, wherein when m is 0, then $R^1$ is
(a2) a $(C_1-C_6)$alkyl group,
(a3) a $(C_2-C_6)$alkenyl group,
(a4) a $(C_2-C_6)$alkynyl group, or
(a5) a $(C_3-C_6)$cycloalkyl group.

8. The anticancer agent according to claim 1, wherein when m is 0, then $R^3$ is
(b2) a $(C_1-C_6)$alkyl group, or
(b3) a $(C_3-C_6)$cycloalkyl group, or
(b4) $R^2$ and $R^3$ are bonded to form a $(C_1-C_6)$alkylene group.

9. The anticancer agent according to claim 1, wherein $R^1$ is
(a1) a hydrogen atom, or
(a4) a $(C_2-C_6)$alkynyl group;
$R^2$, $R^3$, and $R^4$ are the same or different and each is
(b1) a hydrogen atom, or
(b2) a $(C_1-C_6)$alkyl group, or
(b4) $R^2$ and $R^3$ are optionally bonded to form a $(C_1-C_6)$ alkylene group;
$R^5$ and $R^6$ are the same or different and each is
(c1) a hydrogen atom, or
(c6) $R^5$ and $R^6$ are optionally bonded to form a $(C_1-C_6)$ alkylene group;
R is
(d1) a phenyl group,
(d2) a phenyl group having, on the ring, the same or different 1 to 5 substituents selected from
  (a) a halogen atom,
  (b) a cyano group,
  (c) a nitro group,
  (d) a $(C_1-C_6)$alkyl group,
  (e) a halo$(C_1-C_6)$alkyl group,
  (g) a $(C_2-C_6)$alkynyl group,
  (i) a halo$(C_1-C_6)$alkoxy group,
  (j) a halo$(C_2-C_6)$alkenyloxy group,
  (l) a $(C_1-C_6)$alkylthio group,
  (m) a $(C_1-C_6)$alkylsulfonyl group,
  (n) a halo$(C_1-C_6)$alkylthio group,
  (o) a phenyl$(C_2-C_6)$alkynyl group,
  (p) a phenoxy group, and (q) a pyridyloxy group having, on the ring, the same or different 1 to 4 substituents selected from
   (i) a halogen atom, and
   (ii) a halo($C_1$-$C_6$)alkyl group,
(d3) a naphthyl group, or
(d5) a ($C_1$-$C_{12}$)alkyl group;
$Ar^1$ is
(e1) a phenyl group,
(e2) a phenyl group having, on the ring, the same or different 1 to 5 substituents selected from
   (a) a halogen atom,
   (b) a cyano group,
   (c) a nitro group,
   (d) a ($C_1$-$C_6$)alkyl group,
   (e) a halo($C_1$-$C_6$)alkyl group,
   (h) a ($C_1$-$C_6$)alkoxy group,
   (i) a halo($C_1$-$C_6$)alkoxy group,
   (n) a halo($C_1$-$C_6$)alkylthio group,
   (q) a pyridyloxy group having, on the ring, the same or different 1 to 4 substituents selected from
      (i) a halogen atom, and
      (ii) a halo($C_1$-$C_6$)alkyl group,
   (r) a hydroxyl group,
   (s) a phenyl group, and
   (t) a halo($C_1$-$C_6$)alkylsulfonylamino group,
(e3) a naphthyl group,
(e5) a pyridyl group,
(e6) a pyridyl group having, on the ring, the same or different 1 to 4 substituents selected from
   (a) a halogen atom,
   (b) a ($C_1$-$C_6$)alkyl group,
   (c) a halo($C_1$-$C_6$)alkyl group,
   (d) a ($C_1$-$C_6$)alkylthio group,
   (e) a ($C_1$-$C_6$)alkylsulfonyl group, and
   (f) a halo($C_1$-$C_6$)alkylthio group, or
(e8) a pyrazolyl group having, on the ring, the same or different 1 to 3 substituents selected from
   (a) a halogen atom,
   (b) a ($C_1$-$C_6$)alkyl group,
   (c) a halo($C_1$-$C_6$)alkyl group,
   (d) a ($C_1$-$C_6$)alkylthio group,
   (e) a ($C_1$-$C_6$)alkylsulfonyl group, and
   (f) a ($C_1$-$C_6$)alkoxycarbonyl group; and
W is —O—.

10. The anticancer agent according to claim 1, wherein the cancer is selected from colon cancer, lung cancer, mesothelioma, pancreatic cancer, stomach cancer, breast cancer, ovarian cancer, prostate cancer, liver cancer, thyroid cancer, renal cancer, uterine cancer, brain tumor, melanoma, sarcoma, urinary bladder cancer, blood cancer, head and neck cancer, cervix cancer, esophageal cancer, gallbladder cancer, splenic cancer, testicular cancer, peripheral nerve cancer, and skin cancer.

11. The anticancer agent according to claim 1, wherein the cancer is selected from brain tumor, peripheral nerve cancer, and ovarian cancer.

12. The aminoacetonitrile compound represented by the formula (I) according to claim 1
(excluding
N-[(1S)-1-cyano-2-(5-cyano-2-trifluoromethylphenoxy)-1-methyl-ethyl]-4-trifluoromethylsulfanylbenzamide,
N-[(1R)-1-cyano-2-(5-cyano-2-trifluoromethylphenoxy)-1-methyl-ethyl]-4-trifluoromethylsulfanylbenzamide,
N-[1-cyano-2-(5-cyano-2-trifluoromethylphenoxy)-1-methyl-ethyl]-4-trifluoromethylsulfanylbenzamide,
N-[2-(2-chlorophenoxy)-1-cyano-1-methyl-ethyl]-4-trifluoromethylbenzamide,
N-[1-cyano-2-(2-trifluoromethylphenoxy)-1-methyl-ethyl]-4-trifluoromethylbenzamide,
N-[1-cyano-2-(2-trifluoromethylphenoxy)-1-methyl-ethyl]-4-trifluoromethoxybenzamide,
N-[1-cyano-2-(2,5-dichlorophenoxy)-1-methyl-ethyl]-4-trifluoromethoxybenzamide,
N-[2-(2-chloro-5-fluorophenoxy)-1-cyano-1-methyl-ethyl]-4-trifluoromethoxybenzamide,
N-[2-(2-chloro-4-fluorophenoxy)-1-cyano-1-methyl-ethyl]-4-trifluoromethoxybenzamide,
N-[2-(2-bromo-4,5-difluorophenoxy)-1-cyano-1-methyl-ethyl]-4-trifluoromethoxybenzamide, and
N-[1-cyano-2-(4,5-difluoro-2-trifluoromethylphenoxy)-1-methyl-ethyl]-4-trifluoromethoxybenzamide), or a pharmacologically acceptable salt thereof, for use in the treatment of cancer.

* * * * *